(12) United States Patent
Levine et al.

(10) Patent No.: US 12,343,535 B2
(45) Date of Patent: Jul. 1, 2025

(54) VAGUS NERVE STIMULATION TO TREAT NEURODEGENERATIVE DISORDERS

(71) Applicant: SETPOINT MEDICAL CORPORATION, Valencia, CA (US)

(72) Inventors: Jacob A. Levine, West Hempstead, NY (US); Nicole Hamlin, Centereach, NY (US); David Chernoff, Sausalito, CA (US); Manojkumar Gunasekaran, Valencia, CA (US)

(73) Assignee: SetPoint Medical Corporation, Valencia, CA (US)

( * ) Notice: Subject to any disclaimer, the term of this patent is extended or adjusted under 35 U.S.C. 154(b) by 542 days.

(21) Appl. No.: 17/599,594

(22) PCT Filed: Apr. 13, 2020

(86) PCT No.: PCT/US2020/027906
§ 371 (c)(1),
(2) Date: Sep. 29, 2021

(87) PCT Pub. No.: WO2020/210786
PCT Pub. Date: Oct. 15, 2020

(65) Prior Publication Data
US 2022/0193413 A1 Jun. 23, 2022

Related U.S. Application Data

(60) Provisional application No. 62/833,631, filed on Apr. 12, 2019.

(51) Int. Cl.
*A61N 1/36* (2006.01)
*A61N 1/05* (2006.01)

(52) U.S. Cl.
CPC ....... *A61N 1/36053* (2013.01); *A61N 1/3606* (2013.01); *A61N 1/36103* (2013.01);
(Continued)

(58) Field of Classification Search
CPC .............. A61N 1/36053; A61N 1/0556; A61N 1/3606; A61N 1/36135; A61N 1/36171;
(Continued)

(56) References Cited

U.S. PATENT DOCUMENTS 2,164,121 A  6/1939 Pescador
3,363,623 A  1/1968 Atwell
(Continued)

FOREIGN PATENT DOCUMENTS

CN  201230913 A  5/2009
CN  101528303 A  9/2009
(Continued)

OTHER PUBLICATIONS

US 6,184,239 B1, 02/2001, Puskas (withdrawn)
(Continued)

*Primary Examiner* — Pamela M. Bays
*Assistant Examiner* — Christine Sison
(74) *Attorney, Agent, or Firm* — Shay Glenn LLP

(57) ABSTRACT

Systems, devices, and methods for using vagus nerve stimulation to treat demyelination disorders and/or disorder of the blood brain barrier are described. The vagus nerve stimulation therapy described herein is configured to reduce or prevent demyelination and/or promote remyelination to treat various disorders related to demyelination, such as multiple sclerosis. A low duty cycle stimulation protocol with a relatively short on-time and a relatively long off-time can be used.

13 Claims, 18 Drawing Sheets

(52) U.S. Cl.
CPC ..... *A61N 1/36135* (2013.01); *A61N 1/36171* (2013.01); *A61N 1/0556* (2013.01); *A61N 1/36175* (2013.01)

(58) Field of Classification Search
CPC ............ A61N 1/36175; A61N 1/36103; A61N 1/37252
See application file for complete search history.

(56) References Cited

U.S. PATENT DOCUMENTS

| | | |
|---|---|---|
| 3,631,534 A | 12/1971 | Hirota et al. |
| 4,073,296 A | 2/1978 | McCall |
| 4,098,277 A | 7/1978 | Mendell |
| 4,305,402 A | 12/1981 | Katims |
| 4,503,863 A | 3/1985 | Katims |
| 4,573,481 A | 3/1986 | Bullara |
| 4,590,946 A | 5/1986 | Loeb |
| 4,632,095 A | 12/1986 | Libin |
| 4,649,936 A | 3/1987 | Ungar et al. |
| 4,702,254 A | 10/1987 | Zabara |
| 4,840,793 A | 6/1989 | Todd, III et al. |
| 4,867,164 A | 9/1989 | Zabara |
| 4,929,734 A | 5/1990 | Coughenour et al. |
| 4,930,516 A | 6/1990 | Alfano et al. |
| 4,935,234 A | 6/1990 | Todd, III et al. |
| 4,979,511 A | 12/1990 | Terry, Jr. |
| 4,991,578 A | 2/1991 | Cohen |
| 5,019,648 A | 5/1991 | Schlossman et al. |
| 5,025,807 A | 6/1991 | Zabara |
| 5,038,781 A | 8/1991 | Lynch |
| 5,049,659 A | 9/1991 | Cantor et al. |
| 5,073,560 A | 12/1991 | Wu et al. |
| 5,106,853 A | 4/1992 | Showell et al. |
| 5,111,815 A | 5/1992 | Mower |
| 5,154,172 A | 10/1992 | Terry, Jr. et al. |
| 5,175,166 A | 12/1992 | Dunbar et al. |
| 5,179,950 A | 1/1993 | Stanislaw |
| 5,186,170 A | 2/1993 | Varrichio et al. |
| 5,188,104 A | 2/1993 | Wernicke et al. |
| 5,203,326 A | 4/1993 | Collins |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker et al. |
| 5,251,634 A | 10/1993 | Weinberg |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,330,507 A | 7/1994 | Schwartz |
| 5,330,515 A | 7/1994 | Rutecki et al. |
| 5,335,657 A | 8/1994 | Terry, Jr. et al. |
| 5,344,438 A | 9/1994 | Testerman et al. |
| 5,351,394 A | 10/1994 | Weinberg |
| 5,403,845 A | 4/1995 | Dunbar et al. |
| 5,458,625 A | 10/1995 | Kendall |
| 5,472,841 A | 12/1995 | Jayasena et al. |
| 5,487,756 A | 1/1996 | Kallesoe et al. |
| 5,496,938 A | 3/1996 | Gold et al. |
| 5,503,978 A | 4/1996 | Schneider et al. |
| 5,531,778 A | 7/1996 | Maschino et al. |
| 5,540,730 A | 7/1996 | Terry, Jr. et al. |
| 5,540,734 A | 7/1996 | Zabara |
| 5,567,588 A | 10/1996 | Gold et al. |
| 5,567,724 A | 10/1996 | Kelleher et al. |
| 5,571,150 A | 11/1996 | Wernicke et al. |
| 5,580,737 A | 12/1996 | Polisky et al. |
| 5,582,981 A | 12/1996 | Toole et al. |
| 5,604,231 A | 2/1997 | Smith et al. |
| 5,607,459 A | 3/1997 | Paul et al. |
| 5,611,350 A | 3/1997 | John |
| 5,618,818 A | 4/1997 | Ojo et al. |
| 5,629,285 A | 5/1997 | Black et al. |
| 5,637,459 A | 6/1997 | Burke et al. |
| 5,651,378 A | 7/1997 | Matheny et al. |
| 5,654,151 A | 8/1997 | Allen et al. |
| 5,683,867 A | 11/1997 | Biesecker et al. |
| 5,690,681 A | 11/1997 | Geddes et al. |
| 5,690,693 A | 11/1997 | Wang et al. |
| 5,700,282 A | 12/1997 | Zabara |
| 5,705,337 A | 1/1998 | Gold et al. |
| 5,707,400 A | 1/1998 | Terry, Jr. et al. |
| 5,709,853 A | 1/1998 | Iino et al. |
| 5,712,375 A | 1/1998 | Jensen et al. |
| 5,718,912 A | 2/1998 | Thompson et al. |
| 5,726,017 A | 3/1998 | Lochrie et al. |
| 5,726,179 A | 3/1998 | Messer, Jr. et al. |
| 5,727,556 A | 3/1998 | Weth et al. |
| 5,733,255 A | 3/1998 | Dinh et al. |
| 5,741,802 A | 4/1998 | Kem et al. |
| 5,773,598 A | 6/1998 | Burke et al. |
| 5,786,462 A | 7/1998 | Schneider et al. |
| 5,788,656 A | 8/1998 | Mino |
| 5,792,210 A | 8/1998 | Wamubu et al. |
| 5,824,027 A | 10/1998 | Hoffer et al. |
| 5,853,005 A | 12/1998 | Scanlon |
| 5,854,289 A | 12/1998 | Bianchi et al. |
| 5,902,814 A | 5/1999 | Gordon et al. |
| 5,913,876 A | 6/1999 | Taylor et al. |
| 5,916,239 A | 6/1999 | Geddes et al. |
| 5,919,216 A | 7/1999 | Houben et al. |
| 5,928,272 A | 7/1999 | Adkins et al. |
| 5,964,794 A | 10/1999 | Bolz et al. |
| 5,977,144 A | 11/1999 | Meyer et al. |
| 5,994,330 A | 11/1999 | El Khoury |
| 6,002,964 A | 12/1999 | Feler et al. |
| 6,006,134 A | 12/1999 | Hill et al. |
| 6,017,891 A | 1/2000 | Eibl et al. |
| 6,028,186 A | 2/2000 | Tasset et al. |
| 6,051,017 A | 4/2000 | Loeb et al. |
| 6,083,696 A | 7/2000 | Biesecker et al. |
| 6,083,905 A | 7/2000 | Voorberg et al. |
| 6,096,728 A | 8/2000 | Collins et al. |
| 6,104,956 A | 8/2000 | Naritoku et al. |
| 6,110,900 A | 8/2000 | Gold et al. |
| 6,110,914 A | 8/2000 | Phillips et al. |
| 6,117,837 A | 9/2000 | Tracey et al. |
| 6,124,449 A | 9/2000 | Gold et al. |
| 6,127,119 A | 10/2000 | Stephens et al. |
| 6,140,490 A | 10/2000 | Biesecker et al. |
| 6,141,590 A | 10/2000 | Renirie et al. |
| 6,147,204 A | 11/2000 | Gold et al. |
| 6,159,145 A | 12/2000 | Satoh |
| 6,164,284 A | 12/2000 | Schulman et al. |
| 6,166,048 A | 12/2000 | Bencherif |
| 6,168,778 B1 | 1/2001 | Janjic et al. |
| 6,171,795 B1 | 1/2001 | Korman et al. |
| 6,205,359 B1 | 3/2001 | Boveja |
| 6,208,894 B1 | 3/2001 | Schulman et al. |
| 6,208,902 B1 | 3/2001 | Boveja |
| 6,210,321 B1 | 4/2001 | Di Mino et al. |
| 6,224,862 B1 | 5/2001 | Turecek et al. |
| 6,233,488 B1 | 5/2001 | Hess |
| 6,266,564 B1 | 7/2001 | Hill et al. |
| 6,269,270 B1 | 7/2001 | Boveja |
| 6,304,775 B1 | 10/2001 | Iasemidis et al. |
| 6,308,104 B1 | 10/2001 | Taylor et al. |
| 6,337,997 B1 | 1/2002 | Rise |
| 6,339,725 B1 | 1/2002 | Naritoku et al. |
| 6,341,236 B1 | 1/2002 | Osorio et al. |
| 6,356,787 B1 | 3/2002 | Rezai et al. |
| 6,356,788 B2 | 3/2002 | Boveja |
| 6,381,499 B1 | 4/2002 | Taylor et al. |
| 6,405,732 B1 | 6/2002 | Edwards et al. |
| 6,407,095 B1 | 6/2002 | Lochead et al. |
| 6,428,484 B1 | 8/2002 | Battmer et al. |
| 6,429,217 B1 | 8/2002 | Puskas |
| 6,447,443 B1 | 9/2002 | Keogh et al. |
| 6,449,507 B1 | 9/2002 | Hill et al. |
| 6,473,644 B1 | 10/2002 | Terry, Jr. et al. |

(56) References Cited

U.S. PATENT DOCUMENTS

| | | |
|---|---|---|
| 6,479,523 B1 | 11/2002 | Puskas |
| 6,487,446 B1 | 11/2002 | Hill et al. |
| 6,511,500 B1 | 1/2003 | Rahme |
| 6,528,529 B1 | 3/2003 | Brann et al. |
| 6,532,388 B1 | 3/2003 | Hill et al. |
| 6,542,774 B2 | 4/2003 | Hill et al. |
| 6,556,868 B2 | 4/2003 | Naritoku et al. |
| 6,564,102 B1 | 5/2003 | Boveja |
| 6,587,719 B1 | 7/2003 | Barrett et al. |
| 6,587,727 B2 | 7/2003 | Osorio et al. |
| 6,600,956 B2 | 7/2003 | Maschino et al. |
| 6,602,891 B2 | 8/2003 | Messer et al. |
| 6,609,025 B2 | 8/2003 | Barrett et al. |
| 6,610,713 B2 | 8/2003 | Tracey |
| 6,611,715 B1 | 8/2003 | Boveja |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,633,779 B1 | 10/2003 | Schuler et al. |
| 6,656,960 B2 | 12/2003 | Puskas |
| 6,668,191 B1 | 12/2003 | Boveja |
| 6,671,556 B2 | 12/2003 | Osorio et al. |
| 6,684,105 B2 | 1/2004 | Cohen et al. |
| 6,690,973 B2 | 2/2004 | Hill et al. |
| 6,718,208 B2 | 4/2004 | Hill et al. |
| 6,721,603 B2 | 4/2004 | Zabara et al. |
| 6,735,471 B2 | 5/2004 | Hill et al. |
| 6,735,474 B1 | 5/2004 | Loeb et al. |
| 6,735,475 B1 | 5/2004 | Whitehurst et al. |
| 6,760,626 B1 | 7/2004 | Boveja |
| 6,762,032 B1 | 7/2004 | Nelson et al. |
| 6,778,854 B2 | 8/2004 | Puskas |
| 6,804,558 B2 | 10/2004 | Haller et al. |
| RE38,654 E | 11/2004 | Hill et al. |
| 6,826,428 B1 | 11/2004 | Chen et al. |
| 6,832,114 B1 | 12/2004 | Whitehurst et al. |
| 6,838,471 B2 | 1/2005 | Tracey |
| RE38,705 E | 2/2005 | Hill et al. |
| 6,879,859 B1 | 4/2005 | Boveja |
| 6,885,888 B2 | 4/2005 | Rezai |
| 6,901,294 B1 | 5/2005 | Whitehurst et al. |
| 6,904,318 B2 | 6/2005 | Hill et al. |
| 6,920,357 B2 | 7/2005 | Osorio et al. |
| 6,928,320 B2 | 8/2005 | King |
| 6,934,583 B2 | 8/2005 | Weinberg et al. |
| 6,937,903 B2 | 8/2005 | Schuler et al. |
| 6,961,618 B2 | 11/2005 | Osorio et al. |
| 6,978,787 B1 | 12/2005 | Broniatowski |
| 7,011,638 B2 | 3/2006 | Schuler et al. |
| 7,054,686 B2 | 5/2006 | MacDonald |
| 7,054,692 B1 | 5/2006 | Whitehurst et al. |
| 7,058,447 B2 | 6/2006 | Hill et al. |
| 7,062,320 B2 | 6/2006 | Ehlinger, Jr. |
| 7,069,082 B2 | 6/2006 | Lindenthaler |
| 7,072,720 B2 | 7/2006 | Puskas |
| 7,076,307 B2 | 7/2006 | Boveja et al. |
| 7,142,910 B2 | 11/2006 | Puskas |
| 7,142,917 B2 | 11/2006 | Fukui |
| 7,149,574 B2 | 12/2006 | Yun et al. |
| 7,155,279 B2 | 12/2006 | Whitehurst et al. |
| 7,155,284 B1 | 12/2006 | Whitehurst et al. |
| 7,167,750 B2 | 1/2007 | Knudson et al. |
| 7,167,751 B1 | 1/2007 | Whitehurst et al. |
| 7,174,218 B1 | 2/2007 | Kuzma |
| 7,184,828 B2 | 2/2007 | Hill et al. |
| 7,184,829 B2 | 2/2007 | Hill et al. |
| 7,191,012 B2 | 3/2007 | Boveja et al. |
| 7,204,815 B2 | 4/2007 | Connor |
| 7,209,787 B2 | 4/2007 | DiLorenzo |
| 7,225,019 B2 | 5/2007 | Jahns et al. |
| 7,228,167 B2 | 6/2007 | Kara et al. |
| 7,238,715 B2 | 7/2007 | Tracey et al. |
| 7,242,984 B2 | 7/2007 | DiLorenzo |
| 7,269,457 B2 | 9/2007 | Shafer et al. |
| 7,345,178 B2 | 3/2008 | Nunes et al. |
| 7,373,204 B2 | 5/2008 | Gelfand et al. |
| 7,389,145 B2 | 6/2008 | Kilgore et al. |
| 7,454,245 B2 | 11/2008 | Armstrong et al. |
| 7,467,016 B2 | 12/2008 | Colbom |
| 7,544,497 B2 | 6/2009 | Sinclair et al. |
| 7,561,918 B2 | 7/2009 | Armstrong et al. |
| 7,634,315 B2 | 12/2009 | Cholette |
| 7,711,432 B2 | 5/2010 | Thimineur et al. |
| 7,729,760 B2 | 6/2010 | Patel et al. |
| 7,751,891 B2 | 7/2010 | Armstrong et al. |
| 7,776,326 B2 | 8/2010 | Milbrandt et al. |
| 7,797,058 B2 | 9/2010 | Mrva et al. |
| 7,819,883 B2 | 10/2010 | Westlund et al. |
| 7,822,486 B2 | 10/2010 | Foster et al. |
| 7,829,556 B2 | 11/2010 | Bemis et al. |
| 7,869,869 B1 | 1/2011 | Farazi |
| 7,869,885 B2 | 1/2011 | Begnaud et al. |
| 7,937,145 B2 | 5/2011 | Dobak |
| 7,962,220 B2 | 6/2011 | Kolafa et al. |
| 7,974,701 B2 | 7/2011 | Armstrong |
| 7,974,707 B2 | 7/2011 | Inman |
| 7,996,088 B2 | 8/2011 | Marrosu et al. |
| 7,996,092 B2 | 8/2011 | Mrva et al. |
| 8,019,419 B1 | 9/2011 | Panescu et al. |
| 8,060,208 B2 | 11/2011 | Kilgore et al. |
| 8,103,349 B2 | 1/2012 | Donders et al. |
| 8,165,668 B2 | 4/2012 | Dacey, Jr. et al. |
| 8,180,446 B2 | 5/2012 | Dacey, Jr. et al. |
| 8,180,447 B2 | 5/2012 | Dacey et al. |
| 8,195,287 B2 | 6/2012 | Dacey, Jr. et al. |
| 8,214,056 B2 | 7/2012 | Hoffer et al. |
| 8,233,982 B2 | 7/2012 | Libbus |
| 8,391,970 B2 | 3/2013 | Tracey et al. |
| 8,412,338 B2 | 4/2013 | Faltys |
| 8,504,161 B1 | 8/2013 | Komet et al. |
| 8,571,654 B2 | 10/2013 | Libbus et al. |
| 8,577,458 B1 | 11/2013 | Libbus et al. |
| 8,600,505 B2 | 12/2013 | Libbus et al. |
| 8,612,002 B2 | 12/2013 | Faltys et al. |
| 8,630,709 B2 | 1/2014 | Libbus et al. |
| 8,688,212 B2 | 4/2014 | Libbus et al. |
| 8,700,150 B2 | 4/2014 | Libbus et al. |
| 8,729,129 B2 | 5/2014 | Tracey et al. |
| 8,788,034 B2 | 7/2014 | Levine et al. |
| 8,843,210 B2 | 9/2014 | Simon et al. |
| 8,855,767 B2 | 10/2014 | Faltys et al. |
| 8,886,339 B2 | 11/2014 | Faltys et al. |
| 8,914,114 B2 | 12/2014 | Tracey et al. |
| 8,918,178 B2 | 12/2014 | Simon et al. |
| 8,918,191 B2 | 12/2014 | Libbus et al. |
| 8,923,964 B2 | 12/2014 | Libbus et al. |
| 8,983,628 B2 | 3/2015 | Simon et al. |
| 8,983,629 B2 | 3/2015 | Simon et al. |
| 8,996,116 B2 | 3/2015 | Faltys et al. |
| 9,114,262 B2 | 8/2015 | Libbus et al. |
| 9,162,064 B2 | 10/2015 | Faltys et al. |
| 9,174,041 B2 | 11/2015 | Faltys et al. |
| 9,211,409 B2 | 12/2015 | Tracey et al. |
| 9,211,410 B2 | 12/2015 | Levine et al. |
| 9,254,383 B2 | 2/2016 | Simon et al. |
| 9,272,143 B2 | 3/2016 | Libbus et al. |
| 9,358,381 B2 | 6/2016 | Simon et al. |
| 9,399,134 B2 | 7/2016 | Simon et al. |
| 9,403,001 B2 | 8/2016 | Simon et al. |
| 9,409,024 B2 | 8/2016 | KenKnight et al. |
| 9,415,224 B2 | 8/2016 | Libbus et al. |
| 9,452,290 B2 | 9/2016 | Libbus et al. |
| 9,504,832 B2 | 11/2016 | Libbus et al. |
| 9,511,228 B2 | 12/2016 | Amurthur et al. |
| 9,533,153 B2 | 1/2017 | Libbus et al. |
| 9,572,983 B2 | 2/2017 | Levine et al. |
| 9,662,490 B2 | 5/2017 | Tracey et al. |
| 9,700,716 B2 | 7/2017 | Faltys et al. |
| 9,833,621 B2 | 12/2017 | Levine |
| 9,849,286 B2 | 12/2017 | Levine et al. |
| 9,987,492 B2 | 6/2018 | Tracey et al. |

(56) References Cited

U.S. PATENT DOCUMENTS

| | | |
|---|---|---|
| 9,993,651 B2 | 6/2018 | Faltys et al. |
| 10,166,395 B2 | 1/2019 | Tracey et al. |
| 10,220,203 B2 | 3/2019 | Faltys et al. |
| 10,449,358 B2 | 10/2019 | Levine et al. |
| 10,561,846 B2 | 2/2020 | Tracey et al. |
| 10,583,304 B2 | 3/2020 | Faltys et al. |
| 10,596,367 B2 | 3/2020 | Faltys et al. |
| 10,695,569 B2 | 6/2020 | Levine et al. |
| 10,716,936 B2 | 7/2020 | Faltys et al. |
| 10,912,712 B2 | 2/2021 | Tracey et al. |
| 11,051,744 B2 | 7/2021 | Levine et al. |
| 11,110,287 B2 | 9/2021 | Faltys et al. |
| 11,173,307 B2 | 11/2021 | Levine et al. |
| 2001/0002441 A1 | 5/2001 | Boveja |
| 2001/0034542 A1 | 10/2001 | Mann |
| 2002/0026141 A1 | 2/2002 | Houben et al. |
| 2002/0040035 A1 | 4/2002 | Myers et al. |
| 2002/0077675 A1 | 6/2002 | Greenstein |
| 2002/0086871 A1 | 7/2002 | O'Neill et al. |
| 2002/0095139 A1 | 7/2002 | Keogh et al. |
| 2002/0099417 A1 | 7/2002 | Naritoku et al. |
| 2002/0138075 A1 | 9/2002 | Edwards et al. |
| 2002/0138109 A1 | 9/2002 | Keogh et al. |
| 2002/0193859 A1 | 12/2002 | Schulman et al. |
| 2002/0198570 A1 | 12/2002 | Puskas |
| 2003/0018367 A1 | 1/2003 | DiLorenzo |
| 2003/0032852 A1 | 2/2003 | Perreault et al. |
| 2003/0045909 A1 | 3/2003 | Gross et al. |
| 2003/0088301 A1 | 5/2003 | King |
| 2003/0191404 A1 | 10/2003 | Klein |
| 2003/0194752 A1 | 10/2003 | Anderson et al. |
| 2003/0195578 A1 | 10/2003 | Perron et al. |
| 2003/0212440 A1 | 11/2003 | Boveja |
| 2003/0229380 A1 | 12/2003 | Adams et al. |
| 2003/0236557 A1 | 12/2003 | Whitehurst et al. |
| 2003/0236558 A1 | 12/2003 | Whitehurst et al. |
| 2004/0002546 A1 | 1/2004 | Altschuler |
| 2004/0015202 A1 | 1/2004 | Chandler et al. |
| 2004/0015204 A1 | 1/2004 | Whitehurst et al. |
| 2004/0015205 A1 | 1/2004 | Whitehurst et al. |
| 2004/0024422 A1 | 2/2004 | Hill et al. |
| 2004/0024428 A1 | 2/2004 | Barrett et al. |
| 2004/0024439 A1 | 2/2004 | Riso |
| 2004/0030362 A1 | 2/2004 | Hill et al. |
| 2004/0039427 A1 | 2/2004 | Barrett et al. |
| 2004/0048795 A1 | 3/2004 | Ivanova et al. |
| 2004/0049121 A1 | 3/2004 | Yaron |
| 2004/0049240 A1 | 3/2004 | Gerber et al. |
| 2004/0059383 A1 | 3/2004 | Puskas |
| 2004/0111139 A1 | 6/2004 | McCreery et al. |
| 2004/0138517 A1 | 7/2004 | Osorio et al. |
| 2004/0138518 A1 | 7/2004 | Rise et al. |
| 2004/0138536 A1 | 7/2004 | Frei et al. |
| 2004/0146949 A1 | 7/2004 | Tan et al. |
| 2004/0153127 A1 | 8/2004 | Gordon et al. |
| 2004/0158119 A1 | 8/2004 | Osorio et al. |
| 2004/0162584 A1 | 8/2004 | Hill et al. |
| 2004/0172074 A1 | 9/2004 | Yoshihito |
| 2004/0172085 A1 | 9/2004 | Knudson et al. |
| 2004/0172086 A1 | 9/2004 | Knudson et al. |
| 2004/0172088 A1 | 9/2004 | Knudson et al. |
| 2004/0172094 A1 | 9/2004 | Cohen et al. |
| 2004/0176812 A1 | 9/2004 | Knudson et al. |
| 2004/0178706 A1 | 9/2004 | D'Orso |
| 2004/0193231 A1 | 9/2004 | David et al. |
| 2004/0199209 A1 | 10/2004 | Hill et al. |
| 2004/0199210 A1 | 10/2004 | Shelchuk |
| 2004/0204355 A1 | 10/2004 | Tracey et al. |
| 2004/0215272 A1 | 10/2004 | Haubrich et al. |
| 2004/0215287 A1 | 10/2004 | Swoyer et al. |
| 2004/0236381 A1 | 11/2004 | Dinsmoor et al. |
| 2004/0236382 A1 | 11/2004 | Dinsmoor et al. |
| 2004/0240691 A1 | 12/2004 | Grafenberg |
| 2004/0243182 A1 | 12/2004 | Cohen et al. |
| 2004/0243211 A1 | 12/2004 | Colliou et al. |
| 2004/0254612 A1 | 12/2004 | Ezra et al. |
| 2004/0267152 A1 | 12/2004 | Pineda |
| 2005/0021092 A1 | 1/2005 | Yun et al. |
| 2005/0021101 A1 | 1/2005 | Chen et al. |
| 2005/0027328 A1 | 2/2005 | Greenstein |
| 2005/0043774 A1 | 2/2005 | Devlin et al. |
| 2005/0049655 A1 | 3/2005 | Boveja et al. |
| 2005/0065553 A1 | 3/2005 | Ben Ezra et al. |
| 2005/0065573 A1 | 3/2005 | Rezai |
| 2005/0065575 A1 | 3/2005 | Dobak |
| 2005/0070970 A1 | 3/2005 | Knudson et al. |
| 2005/0070974 A1 | 3/2005 | Knudson et al. |
| 2005/0075694 A1 | 4/2005 | Schmeling et al. |
| 2005/0075698 A1 | 4/2005 | Phillips et al. |
| 2005/0075701 A1 | 4/2005 | Shafer |
| 2005/0075702 A1 | 4/2005 | Shafer |
| 2005/0095246 A1 | 5/2005 | Shafer |
| 2005/0096707 A1 | 5/2005 | Hill et al. |
| 2005/0103351 A1 | 5/2005 | Stomberg et al. |
| 2005/0113894 A1 | 5/2005 | Zilberman et al. |
| 2005/0131467 A1 | 6/2005 | Boveja |
| 2005/0131486 A1 | 6/2005 | Boveja et al. |
| 2005/0131487 A1 | 6/2005 | Boveja |
| 2005/0131493 A1 | 6/2005 | Boveja et al. |
| 2005/0137644 A1 | 6/2005 | Boveja et al. |
| 2005/0137645 A1 | 6/2005 | Voipio et al. |
| 2005/0143781 A1 | 6/2005 | Carbunaru et al. |
| 2005/0143787 A1 | 6/2005 | Boveja et al. |
| 2005/0149126 A1 | 7/2005 | Libbus |
| 2005/0149129 A1 | 7/2005 | Libbus et al. |
| 2005/0149131 A1 | 7/2005 | Libbus et al. |
| 2005/0153885 A1 | 7/2005 | Yun et al. |
| 2005/0154425 A1 | 7/2005 | Boveja et al. |
| 2005/0154426 A1 | 7/2005 | Boveja et al. |
| 2005/0165458 A1 | 7/2005 | Boveja et al. |
| 2005/0177200 A1 | 8/2005 | George et al. |
| 2005/0182288 A1 | 8/2005 | Zabara |
| 2005/0182467 A1 | 8/2005 | Hunter et al. |
| 2005/0187584 A1 | 8/2005 | Denker et al. |
| 2005/0187586 A1 | 8/2005 | David et al. |
| 2005/0187590 A1 | 8/2005 | Boveja et al. |
| 2005/0191661 A1 | 9/2005 | Gatanaga et al. |
| 2005/0192644 A1 | 9/2005 | Boveja et al. |
| 2005/0197600 A1 | 9/2005 | Schuler et al. |
| 2005/0197675 A1 | 9/2005 | David et al. |
| 2005/0197678 A1 | 9/2005 | Boveja et al. |
| 2005/0203501 A1 | 9/2005 | Aldrich et al. |
| 2005/0209654 A1 | 9/2005 | Boveja et al. |
| 2005/0216064 A1 | 9/2005 | Heruth et al. |
| 2005/0216070 A1 | 9/2005 | Boveja et al. |
| 2005/0216071 A1 | 9/2005 | Devlin et al. |
| 2005/0240229 A1 | 10/2005 | Whitehurst et al. |
| 2005/0240231 A1 | 10/2005 | Aldrich et al. |
| 2005/0240241 A1 | 10/2005 | Yun et al. |
| 2005/0240242 A1 | 10/2005 | DiLorenzo |
| 2005/0251220 A1 | 11/2005 | Barrett et al. |
| 2005/0251222 A1 | 11/2005 | Barrett et al. |
| 2005/0267542 A1 | 12/2005 | David et al. |
| 2005/0267547 A1 | 12/2005 | Knudson et al. |
| 2005/0277912 A1 | 12/2005 | John |
| 2005/0283198 A1 | 12/2005 | Haubrich et al. |
| 2006/0009815 A1 | 1/2006 | Boveja et al. |
| 2006/0015151 A1 | 1/2006 | Aldrich |
| 2006/0025828 A1 | 2/2006 | Armstrong et al. |
| 2006/0036293 A1 | 2/2006 | Whitehurst et al. |
| 2006/0052657 A9 | 3/2006 | Zabara |
| 2006/0052831 A1 | 3/2006 | Fukui |
| 2006/0052836 A1 | 3/2006 | Kim et al. |
| 2006/0058851 A1 | 3/2006 | Cigaina |
| 2006/0064137 A1 | 3/2006 | Stone |
| 2006/0064139 A1 | 3/2006 | Chung et al. |
| 2006/0074450 A1 | 4/2006 | Boveja et al. |
| 2006/0074473 A1 | 4/2006 | Gertner |
| 2006/0079936 A1 | 4/2006 | Boveja et al. |
| 2006/0085046 A1 | 4/2006 | Rezai et al. |
| 2006/0095081 A1 | 5/2006 | Zhou et al. |
| 2006/0095090 A1 | 5/2006 | De Ridder |
| 2006/0100668 A1 | 5/2006 | Ben-David et al. |
| 2006/0106755 A1 | 5/2006 | Stuhec |

(56) References Cited

U.S. PATENT DOCUMENTS

| | | |
|---|---|---|
| 2006/0111644 A1 | 5/2006 | Guttag et al. |
| 2006/0111754 A1 | 5/2006 | Rezai et al. |
| 2006/0111755 A1 | 5/2006 | Stone et al. |
| 2006/0116739 A1 | 6/2006 | Betser et al. |
| 2006/0122675 A1 | 6/2006 | Libbus et al. |
| 2006/0129200 A1 | 6/2006 | Kurokawa |
| 2006/0129202 A1 | 6/2006 | Armstrong |
| 2006/0135998 A1 | 6/2006 | Libbus et al. |
| 2006/0136024 A1 | 6/2006 | Cohen et al. |
| 2006/0142802 A1 | 6/2006 | Armstrong |
| 2006/0142822 A1 | 6/2006 | Tulgar |
| 2006/0149337 A1 | 7/2006 | John |
| 2006/0155495 A1 | 7/2006 | Osorio et al. |
| 2006/0161216 A1 | 7/2006 | John et al. |
| 2006/0161217 A1 | 7/2006 | Jaax et al. |
| 2006/0167497 A1 | 7/2006 | Armstrong et al. |
| 2006/0167498 A1 | 7/2006 | DiLorenzo |
| 2006/0167501 A1 | 7/2006 | Ben-David et al. |
| 2006/0173493 A1 | 8/2006 | Armstrong et al. |
| 2006/0173508 A1 | 8/2006 | Stone et al. |
| 2006/0178691 A1 | 8/2006 | Binmoeller |
| 2006/0178703 A1 | 8/2006 | Huston et al. |
| 2006/0178706 A1 | 8/2006 | Lisogurski et al. |
| 2006/0190044 A1 | 8/2006 | Libbus et al. |
| 2006/0190053 A1 | 8/2006 | Dobak |
| 2006/0200208 A1 | 9/2006 | Terry et al. |
| 2006/0200219 A1 | 9/2006 | Thrope et al. |
| 2006/0206155 A1 | 9/2006 | Ben-David et al. |
| 2006/0206158 A1 | 9/2006 | Wu et al. |
| 2006/0229677 A1 | 10/2006 | Moffitt et al. |
| 2006/0229681 A1 | 10/2006 | Fischell |
| 2006/0241697 A1 | 10/2006 | Libbus et al. |
| 2006/0241699 A1 | 10/2006 | Libbus et al. |
| 2006/0247719 A1 | 11/2006 | Maschino et al. |
| 2006/0247721 A1 | 11/2006 | Maschino et al. |
| 2006/0247722 A1 | 11/2006 | Maschino et al. |
| 2006/0259077 A1 | 11/2006 | Pardo et al. |
| 2006/0259084 A1 | 11/2006 | Zhang et al. |
| 2006/0259085 A1 | 11/2006 | Zhang et al. |
| 2006/0259107 A1 | 11/2006 | Caparso et al. |
| 2006/0271115 A1 | 11/2006 | Ben-Ezra et al. |
| 2006/0282121 A1 | 12/2006 | Payne et al. |
| 2006/0282131 A1 | 12/2006 | Caparso et al. |
| 2006/0282145 A1 | 12/2006 | Caparso et al. |
| 2006/0287678 A1 | 12/2006 | Shafer |
| 2006/0287679 A1 | 12/2006 | Stone |
| 2006/0292099 A1 | 12/2006 | Milburn et al. |
| 2006/0293720 A1 | 12/2006 | DiLorenzo |
| 2006/0293721 A1 | 12/2006 | Tarver et al. |
| 2006/0293723 A1 | 12/2006 | Whitehurst et al. |
| 2007/0016262 A1 | 1/2007 | Gross et al. |
| 2007/0016263 A1 | 1/2007 | Armstrong et al. |
| 2007/0021785 A1 | 1/2007 | Inman et al. |
| 2007/0021786 A1 | 1/2007 | Paris et al. |
| 2007/0021814 A1 | 1/2007 | Inman et al. |
| 2007/0025608 A1 | 2/2007 | Armstrong |
| 2007/0027482 A1 | 2/2007 | Paris et al. |
| 2007/0027483 A1 | 2/2007 | Maschino et al. |
| 2007/0027484 A1 | 2/2007 | Guzman et al. |
| 2007/0027486 A1 | 2/2007 | Armstrong |
| 2007/0027492 A1 | 2/2007 | Maschino et al. |
| 2007/0027496 A1 | 2/2007 | Paris et al. |
| 2007/0027497 A1 | 2/2007 | Paris |
| 2007/0027498 A1 | 2/2007 | Maschino et al. |
| 2007/0027499 A1 | 2/2007 | Maschino et al. |
| 2007/0027500 A1 | 2/2007 | Maschino et al. |
| 2007/0027504 A1 | 2/2007 | Barrett et al. |
| 2007/0055324 A1 | 3/2007 | Thompson et al. |
| 2007/0067004 A1 | 3/2007 | Boveja et al. |
| 2007/0083242 A1 | 4/2007 | Mazgalev et al. |
| 2007/0093434 A1 | 4/2007 | Rossetti et al. |
| 2007/0093870 A1 | 4/2007 | Maschino |
| 2007/0093875 A1 | 4/2007 | Chavan et al. |
| 2007/0100263 A1 | 5/2007 | Merfeld |
| 2007/0100377 A1 | 5/2007 | Armstrong et al. |
| 2007/0100378 A1* | 5/2007 | Maschino ............... A61N 1/32 607/2 |
| 2007/0100380 A1 | 5/2007 | Fukui |
| 2007/0100392 A1 | 5/2007 | Maschino et al. |
| 2007/0106339 A1 | 5/2007 | Enrico et al. |
| 2007/0112404 A1 | 5/2007 | Mann et al. |
| 2007/0118177 A1 | 5/2007 | Libbus et al. |
| 2007/0118178 A1 | 5/2007 | Fukui |
| 2007/0129767 A1 | 6/2007 | Wahlstrand |
| 2007/0129780 A1 | 6/2007 | Whitehurst et al. |
| 2007/0135846 A1 | 6/2007 | Knudson et al. |
| 2007/0135856 A1 | 6/2007 | Knudson et al. |
| 2007/0135857 A1 | 6/2007 | Knudson et al. |
| 2007/0135858 A1 | 6/2007 | Knudson et al. |
| 2007/0136098 A1 | 6/2007 | Smythe et al. |
| 2007/0142870 A1 | 6/2007 | Knudson et al. |
| 2007/0142871 A1 | 6/2007 | Libbus et al. |
| 2007/0142874 A1 | 6/2007 | John |
| 2007/0150006 A1 | 6/2007 | Libbus et al. |
| 2007/0150011 A1 | 6/2007 | Meyer et al. |
| 2007/0150021 A1 | 6/2007 | Chen et al. |
| 2007/0150027 A1 | 6/2007 | Rogers |
| 2007/0156180 A1 | 7/2007 | Jaax et al. |
| 2007/0198063 A1 | 8/2007 | Hunter et al. |
| 2007/0239243 A1 | 10/2007 | Moffitt et al. |
| 2007/0244522 A1 | 10/2007 | Overstreet |
| 2007/0250145 A1 | 10/2007 | Kraus et al. |
| 2007/0255320 A1 | 11/2007 | Inman et al. |
| 2007/0255333 A1 | 11/2007 | Giftakis |
| 2007/0255339 A1 | 11/2007 | Torgerson |
| 2008/0015659 A1 | 1/2008 | Zhang |
| 2008/0021517 A1 | 1/2008 | Dietrich |
| 2008/0021520 A1 | 1/2008 | Dietrich |
| 2008/0046055 A1 | 2/2008 | Durand et al. |
| 2008/0051852 A1 | 2/2008 | Dietrich et al. |
| 2008/0058871 A1 | 3/2008 | Libbus et al. |
| 2008/0103407 A1 | 5/2008 | Bolea et al. |
| 2008/0140138 A1 | 6/2008 | Ivanova et al. |
| 2008/0166348 A1 | 7/2008 | Kupper et al. |
| 2008/0183226 A1 | 7/2008 | Buras et al. |
| 2008/0183246 A1 | 7/2008 | Patel et al. |
| 2008/0195171 A1 | 8/2008 | Sharma |
| 2008/0208266 A1 | 8/2008 | Lesser et al. |
| 2008/0213331 A1 | 9/2008 | Gelfand et al. |
| 2008/0234780 A1 | 9/2008 | Smith |
| 2008/0234790 A1 | 9/2008 | Bayer et al. |
| 2008/0281197 A1 | 11/2008 | Wiley et al. |
| 2008/0281365 A1 | 11/2008 | Tweden et al. |
| 2008/0281372 A1 | 11/2008 | Libbus et al. |
| 2009/0012590 A1 | 1/2009 | Inman et al. |
| 2009/0048194 A1 | 2/2009 | Aerssens et al. |
| 2009/0076561 A1 | 3/2009 | Libbus et al. |
| 2009/0082832 A1 | 3/2009 | Carbunaru et al. |
| 2009/0088821 A1 | 4/2009 | Abrahamson |
| 2009/0105782 A1 | 4/2009 | Mickle et al. |
| 2009/0112291 A1 | 4/2009 | Wahlstrand et al. |
| 2009/0123521 A1 | 5/2009 | Weber et al. |
| 2009/0125076 A1 | 5/2009 | Shuros et al. |
| 2009/0125079 A1 | 5/2009 | Armstrong et al. |
| 2009/0131995 A1 | 5/2009 | Sloan et al. |
| 2009/0143831 A1 | 6/2009 | Huston et al. |
| 2009/0171405 A1 | 7/2009 | Craig |
| 2009/0177112 A1 | 7/2009 | Gharib et al. |
| 2009/0182388 A1 | 7/2009 | Von Arx et al. |
| 2009/0187231 A1 | 7/2009 | Errico et al. |
| 2009/0210042 A1 | 8/2009 | Kowalczewski |
| 2009/0248097 A1 | 10/2009 | Tracey et al. |
| 2009/0254143 A1 | 10/2009 | Tweden et al. |
| 2009/0275997 A1 | 11/2009 | Faltys et al. |
| 2009/0276019 A1 | 11/2009 | Perez et al. |
| 2009/0281593 A9 | 11/2009 | Enrico et al. |
| 2009/0281594 A1 | 11/2009 | King et al. |
| 2009/0312817 A1 | 12/2009 | Hogle et al. |
| 2010/0003656 A1 | 1/2010 | Kilgard et al. |
| 2010/0010556 A1 | 1/2010 | Zhao et al. |
| 2010/0010571 A1 | 1/2010 | Skelton et al. |
| 2010/0010581 A1 | 1/2010 | Goetz et al. |
| 2010/0010603 A1 | 1/2010 | Ben-David et al. |
| 2010/0016746 A1 | 1/2010 | Hampton et al. |

(56) References Cited

U.S. PATENT DOCUMENTS

| | | |
|---|---|---|
| 2010/0042186 A1 | 2/2010 | Ben-David et al. |
| 2010/0063563 A1 | 3/2010 | Craig |
| 2010/0074934 A1 | 3/2010 | Hunter |
| 2010/0167937 A1 | 7/2010 | Goldknopf et al. |
| 2010/0191304 A1 | 7/2010 | Scott |
| 2010/0204766 A1 | 8/2010 | Zdeblick et al. |
| 2010/0215632 A1 | 8/2010 | Boss et al. |
| 2010/0219796 A1 | 9/2010 | Kallmyer |
| 2010/0241183 A1 | 9/2010 | DiLorenzo |
| 2010/0241195 A1 | 9/2010 | Meadows et al. |
| 2010/0241207 A1 | 9/2010 | Bluger |
| 2010/0249859 A1 | 9/2010 | DiLorenzo |
| 2010/0280500 A1 | 11/2010 | Skelton et al. |
| 2010/0280562 A1 | 11/2010 | Pi et al. |
| 2010/0280569 A1 | 11/2010 | Bobillier et al. |
| 2011/0004266 A1 | 1/2011 | Sharma |
| 2011/0009734 A1 | 1/2011 | Foley et al. |
| 2011/0042574 A1 | 2/2011 | Nishino et al. |
| 2011/0054569 A1 | 3/2011 | Zitnik et al. |
| 2011/0066208 A1 | 3/2011 | Pasricha et al. |
| 2011/0082515 A1 | 4/2011 | Libbus et al. |
| 2011/0092882 A1 | 4/2011 | Firlik et al. |
| 2011/0144717 A1 | 6/2011 | Burton et al. |
| 2011/0145588 A1 | 6/2011 | Stubbs et al. |
| 2011/0152967 A1 | 6/2011 | Simon et al. |
| 2011/0224749 A1 | 9/2011 | Ben-David et al. |
| 2011/0247620 A1 | 10/2011 | Armstrong et al. |
| 2011/0275927 A1 | 11/2011 | Wagner et al. |
| 2011/0301658 A1 | 12/2011 | Yoo et al. |
| 2011/0301667 A1 | 12/2011 | Olson et al. |
| 2011/0307027 A1 | 12/2011 | Sharma et al. |
| 2012/0053657 A1 | 3/2012 | Parker et al. |
| 2012/0065706 A1 | 3/2012 | Vallapureddy et al. |
| 2012/0179219 A1 | 7/2012 | Kisker et al. |
| 2012/0185009 A1 | 7/2012 | Kornet et al. |
| 2012/0185020 A1 | 7/2012 | Simon et al. |
| 2012/0296176 A1 | 11/2012 | Herbst |
| 2012/0302821 A1 | 11/2012 | Burnett |
| 2013/0013016 A1 | 1/2013 | Diebold |
| 2013/0018439 A1 | 1/2013 | Chow et al. |
| 2013/0066392 A1 | 3/2013 | Simon et al. |
| 2013/0066395 A1 | 3/2013 | Simon et al. |
| 2013/0071390 A1 | 3/2013 | Stadheim et al. |
| 2013/0150756 A1 | 6/2013 | Vitek et al. |
| 2013/0245718 A1 | 9/2013 | Birkholz et al. |
| 2013/0278226 A1 | 10/2013 | Cong et al. |
| 2013/0289385 A1 | 10/2013 | Lozano et al. |
| 2013/0317580 A1 | 11/2013 | Simon et al. |
| 2014/0046407 A1 | 2/2014 | Ben-Ezra et al. |
| 2014/0070761 A1 | 3/2014 | Labbe et al. |
| 2014/0206945 A1 | 7/2014 | Liao |
| 2014/0213926 A1 | 7/2014 | Vaidyanathan |
| 2014/0257425 A1 | 9/2014 | Arcot-Krishnamurthy et al. |
| 2014/0277260 A1 | 9/2014 | Khalil et al. |
| 2014/0288551 A1 | 9/2014 | Bharmi et al. |
| 2014/0324118 A1 | 10/2014 | Simon et al. |
| 2014/0330335 A1 | 11/2014 | Errico et al. |
| 2014/0371818 A1 | 12/2014 | Bond et al. |
| 2015/0018728 A1 | 1/2015 | Gross et al. |
| 2015/0119956 A1 | 4/2015 | Libbus et al. |
| 2015/0133717 A1 | 5/2015 | Ghiron et al. |
| 2015/0180271 A1 | 6/2015 | Angara et al. |
| 2015/0196767 A1 | 7/2015 | Ahmed |
| 2015/0202446 A1 | 7/2015 | Franke et al. |
| 2015/0233904 A1 | 8/2015 | Nayak |
| 2015/0241447 A1 | 8/2015 | Zitnik et al. |
| 2015/0321001 A1* | 11/2015 | Libbus .............. A61N 1/37264 607/62 |
| 2016/0089540 A1 | 3/2016 | Bolea |
| 2016/0114165 A1 | 4/2016 | Levine et al. |
| 2016/0250097 A9 | 9/2016 | Tracey et al. |
| 2016/0279435 A1 | 9/2016 | Hyde et al. |
| 2016/0331952 A1 | 11/2016 | Fallys et al. |
| 2016/0367808 A9 | 12/2016 | Simon et al. |
| 2017/0189699 A1 | 7/2017 | Dellamano et al. |
| 2017/0202467 A1 | 7/2017 | Zitnik et al. |
| 2017/0239484 A1 | 8/2017 | Ram Rakhyani et al. |
| 2017/0245379 A1 | 8/2017 | Kang |
| 2017/0254818 A1 | 9/2017 | Haskins et al. |
| 2017/0304621 A1 | 10/2017 | Malbert et al. |
| 2017/0361093 A1 | 12/2017 | Yoo et al. |
| 2018/0001096 A1 | 1/2018 | Faltys et al. |
| 2018/0021580 A1 | 1/2018 | Tracey et al. |
| 2018/0078769 A1 | 3/2018 | Dinsmoor et al. |
| 2018/0085578 A1* | 3/2018 | Rennaker, II ...... A61N 1/36067 |
| 2018/0117320 A1 | 5/2018 | Levine et al. |
| 2018/0133460 A1 | 5/2018 | Townley et al. |
| 2018/0289970 A1 | 10/2018 | Faltys et al. |
| 2019/0010535 A1 | 1/2019 | Pujol Onofre et al. |
| 2019/0022389 A1 | 1/2019 | Leonhardt |
| 2019/0030334 A1 | 1/2019 | Lerman et al. |
| 2019/0054295 A1 | 2/2019 | Pannu et al. |
| 2019/0090358 A1 | 3/2019 | Aresta et al. |
| 2019/0111263 A1 | 4/2019 | Levine et al. |
| 2019/0192847 A1 | 6/2019 | Faltys et al. |
| 2019/0209844 A1 | 7/2019 | Estellar et al. |
| 2019/0240490 A1 | 8/2019 | Yeh et al. |
| 2019/0275328 A1 | 9/2019 | Zitnik et al. |
| 2019/0290902 A1 | 9/2019 | Romero-Ortega et al. |
| 2019/0358461 A1 | 11/2019 | Steinke |
| 2020/0078589 A1 | 3/2020 | Simon et al. |
| 2020/0094055 A1 | 3/2020 | Manogue |
| 2020/0171312 A1 | 6/2020 | Dinsmoor et al. |
| 2020/0206515 A1 | 7/2020 | Faltys et al. |
| 2020/0238078 A1 | 7/2020 | Faltys et al. |
| 2020/0330760 A1 | 10/2020 | Levine et al. |
| 2020/0384259 A1 | 12/2020 | Chasensky et al. |
| 2020/0402656 A1 | 12/2020 | DeBates et al. |
| 2021/0121696 A1 | 4/2021 | Parker et al. |
| 2021/0251848 A1 | 8/2021 | Tracey et al. |
| 2021/0315505 A1 | 10/2021 | Levine et al. |
| 2021/0353949 A1 | 11/2021 | Faltys et al. |
| 2022/0040483 A1 | 2/2022 | Levine et al. |
| 2022/0189604 A1 | 6/2022 | El-Khatib et al. |
| 2022/0212001 A1 | 7/2022 | Faltys et al. |
| 2023/0117074 A1 | 4/2023 | Zanos et al. |
| 2023/0144580 A1 | 5/2023 | Manogue |
| 2023/0241387 A1 | 8/2023 | Levine et al. |
| 2023/0321445 A1 | 10/2023 | Zanos et al. |
| 2024/0215900 A1 | 7/2024 | Levine et al. |
| 2024/0216688 A1 | 7/2024 | Zitnik et al. |

FOREIGN PATENT DOCUMENTS

| | | |
|---|---|---|
| CN | 101578067 A | 11/2009 |
| CN | 101868280 A | 10/2010 |
| CN | 104220129 A | 12/2014 |
| CN | 104602759 A | 5/2015 |
| DE | 2628045 A1 | 1/1977 |
| DE | 3736664 A1 | 5/1989 |
| DE | 20316509 U1 | 4/2004 |
| EP | 0438510 B1 | 8/1996 |
| EP | 0726791 B1 | 6/2000 |
| EP | 1001827 B1 | 1/2004 |
| EP | 2213330 A2 | 8/2010 |
| EP | 2073896 B1 | 10/2011 |
| EP | 3470111 A1 | 4/2019 |
| GB | 04133 | 2/1910 |
| GB | 2073428 A | 10/1981 |
| JP | 2017502787 | 1/2017 |
| JP | 2019517830 | 6/2019 |
| KR | 20050039445 A | 4/2005 |
| WO | WO93/01862 A1 | 2/1993 |
| WO | WO97/30998 A1 | 8/1997 |
| WO | WO98/20868 A1 | 5/1998 |
| WO | WO00/27381 A2 | 5/2000 |
| WO | WO00/47104 A2 | 8/2000 |
| WO | WO01/00273 A1 | 1/2001 |
| WO | WO01/08617 A1 | 2/2001 |
| WO | WO01/89526 A1 | 11/2001 |
| WO | WO02/44176 A1 | 6/2002 |
| WO | WO02/057275 A1 | 7/2002 |
| WO | WO03/072135 A2 | 9/2003 |
| WO | WO2004/000413 A2 | 12/2003 |

(56) References Cited

FOREIGN PATENT DOCUMENTS

| WO | WO2004/064918 A1 | 8/2004 |
| --- | --- | --- |
| WO | WO2006/073484 A1 | 7/2006 |
| WO | WO2006/076681 A2 | 7/2006 |
| WO | WO2007/133718 A2 | 11/2007 |
| WO | WO2010/005482 A1 | 1/2010 |
| WO | WO2010/067360 A2 | 6/2010 |
| WO | WO2010/118035 A2 | 10/2010 |
| WO | WO2015/009907 A1 | 1/2015 |
| WO | WO2016/134197 A1 | 8/2016 |
| WO | WO2019/204884 A1 | 10/2019 |

OTHER PUBLICATIONS

Yang IH, Gary D, Malone M, Dria S, Houdayer T, Belegu V, McDonald JW, Thakor N. Axon myelination and electrical stimulation in a microfluidic, compartmentalized cell culture platform. Neuromolecular Med. Jun. 2012; 14(2): 112-8. doi: 10.1007/s12017-012-8170-5. Epub Apr. 13, 2012. PMID: 22527791. (Year: 2012).*

McLean, Nikki A et al. "Delayed nerve stimulation promotes axon-protective neurofilament phosphorylation, accelerates immune cell clearance and enhances remyelination in vivo in focally demyelinated nerves." PloS one vol. 9, 10 e110174. Oct. 13, 2014, doi: 10.1371/journal.pone.0110174 (Year: 2014).*

Huston et al.; U.S. Appl. No. 17/646,144 entitled "Treating inflammatory disorders by stimulation of the cholinergic anti-inflammatory pathway," filed Dec. 27, 2021.

Manogue; U.S. Appl. No. 17/578,339 entitled "Methods and apparatuses for reducing bleeding via coordinated trigeminal and vagal nerve stimulation," filed Jan. 18, 2022.

De Jonge et al.; Stimulation of the vagus nerve attenuates macrophage activation by activating the Jak2-STAT3 signaling pathway; Nature Immunology; 6(8); pp. 844-851; Aug. 2005.

Emery et al.; Rituximab versus an alternative TNF inhibitor in patients with rheumatoid arthritis who failed to respond to a single previous TNF inhibitor: switch-ra, a global, oberservational, comparative effectiveness study; Annals of the Rheumatic Diseases; 4(6); pp. 979-984; Jun. 2015.

Gottenberg et al.; Non-TNF-targeted biologic vs a second anti-TNF drug to treat rheumatoid arthritis in patients with insufficient response to a first anti TNF drug: a randomized clinical trial; JAMA; 316(11); pp. 1172-1180; Sep. 2016.

Monaco et al.; Anti-TNF therapy:past,present, and future; International Immunology; 27(1); pp. 55-62; Jan. 2015.

Olofsson et al.; Single-pulse and unidirectional electrical activation of the cervical vagus nerve reduces tumor necrosis factor in endotoxemia; Bioelectronic Medicine; 2(1); pp. 37-42; Jun. 2015.

Pasricha et al.; Sacral nerve stimulation prompts vagally-mediated amelioration of rodent colitis; Physiological Reports; 8(1); e14294; 7 pages; Jan. 2020.

Rendas-Baum et al.; Evaluating the efficacy of sequential biologic therapies for rheumatoid arthritis patients with an inadequate response to tumor necrosis factor-alpha inhibitors; Arthritis research and therapy; 13; R25; 15 pages; ; Feb. 2011.

Rosas-Ballina et al.; Acetylcholine-synthesizing T cells relay neural signals in a vagus nerve circuit Science; 334(6052); pp. 98-101; 10 pages; (Author Manuscript); Oct. 2011.

Vida et al.; Aplha 7-cholinergic receptor mediates vagal induction of splenic norepinephrine; Journal of Immunology: 186(7); pp. 4340-4346; 16 pages; (Author Manuscript); Apr. 2011.

Yang et al.; Acetylcholine inhibits LPS-induced MMP-9 production and ccell migration via the alpha7 nAChR-JAK2/STAT3 pathway in RAW264.7 cells; Cellular Physiology and Biochemistry; 36(5); pp. 2025-2038; (the year of publication is sufficiently earlier than the effective U.S. filing date and any foreign priority date so that the particular month of publication is not in issue) 2015.

Levine et al.; U.S. Appl. No. 17/728,765 entitled "Systems and methods for stimulating and/or monitoring loci in the brain to treat inflammation and to enhance vagus nerve stimulation," filed Apr. 25, 2022.

Faltys et al.; U.S. Appl. No. 17/751,505 entitled "Implantable neurostimulator having power control and thermal regulation and methods of use," filed May 23, 2022.

Jacob et al.; Detrimental role of granulocyte-colony stimulating factor in neuromyelitis optica: clinical case and histological evidence; Multiple Sclerosis Journal; 18(12); pp. 1801-1803; Dec. 2012.

Levine et al.; U.S. Appl. No. 18/151,407 entitled "Control of vagal stimulation," filed Jan. 6, 2023.

Abraham, Coagulation abnormalities in acute lung injury and sepsis, Am. J. Respir. Cell Mol. Biol., vol. 22(4), pp. 401-404, Apr. 2000.

Aekerlund et al., Anti-inflammatory effects of a new tumour necrosis factor-alpha (TNF-Alpha) inhibitor (CNI-1493) in collagen-induced arthritis (CIA) in rats, Clinical & Experimental Immunology, vol. 115, No. 1, pp. 32-41, Jan. 1, 1999.

Anderson et al.; Reflex principles of immunological homeostasis; Annu. Rev. Immunol.; 30; pp. 313-335; Apr. 2012.

Antonica, A., et al., Vagal control of lymphocyte release from rat thymus, J. Auton. Nerv. Syst., vol. 48(3), pp. 187-197, Aug. 1994.

Asakura et al., Non-surgical therapy for ulcerative colitis, Nippon Geka Gakkai Zasshi, vol. 98, No. 4, pp. 431-437, Apr. 1997 (abstract only).

Beliavskaia et al.,"On the effects of prolonged stimulation of the peripheral segment of the vagus nerve . . . ," Fiziologicheskii Zhurnal SSSR Imeni I.M. Sechenova., vol. 52(11); p. 1315-1321, Nov. 1966.

Ben-Noun et al.; Neck circumference as a simple screening measure for identifying overweight and obese patients; Obesity Research; vol. 9; No. 8; pp. 470-477; Aug. 8, 2001.

Benoist, et al., "Mast cells in autoimmune disease" Nature., vol. 420(19): pp. 875-878, Dec. 2002.

Benthem et al.; Parasympathetic inhibition of sympathetic neural activity to the pancreas; Am.J.Physiol Endocrinol.Metab; 280(2); pp. E378-E381; Feb. 2001.

Bernik et al., Vagus nerve stimulation attenuates cardiac TNF production in endotoxic shock, (supplemental to Shock, vol. 15, 2001, Injury, inflammation and sepsis: laboratory and clinical approaches, Shock, Abstracts, 24th Annual Conference on Shock, Marco Island, FL, Jun. 9-12, 2001), Abstract No. 81.

Bernik et al., Vagus nerve stimulation attenuates endotoxic shock and cardiac TNF production, 87th Clinical Congress of the American College of Surgeons, New Orleans, LA, Oct. 9, 2001.

Bernik et al., Vagus nerve stimulation attenuates LPS-induced cardiac TNF production and myocardial depression IN shock, New York Surgical Society, New York, NY, Apr. 11, 2001.

Bernik, et al., Pharmacological stimulation of the cholinergic anti-inflammatory pathway, The Journal of Experimental Medicine, vol. 195, No. 6, pp. 781-788, Mar. 18, 2002.

Besedovsky, H., et al., Immunoregulatory feedback between interleukin-1 and glucocorticoid hormones, Science, vol. 233, No. 4764, pp. 652-654, Aug. 1986.

Bhattacharya, S.K. et al., Central muscarinic receptor subtypes and carrageenin-induced paw oedema in rats, Res. Esp. Med. vol. 191(1), pp. 65-76, Dec. 1991.

Bianchi et al., Suppression of proinflammatory cytokines in monocytes by a tetravalent guanylhydrazone, Journal of Experimental Medicine, vol. 183, pp. 927-936, Mar. 1996.

Biggio et al.; Chronic vagus nerve stimulation induces neuronal plasticity in the rat hippocampus; Int. J. Neurpsychopharmacol.; vol. 12; No. 9; pp. 1209-1221; Oct. 2009.

Blackwell, T. S. et al., Sepsis and cytokines: current status, Br. J. Anaesth., vol. 77(1), pp. 110-117, Jul. 1996.

Blum, A. et al., Role of cytokines in heart failure, Am. Heart J., vol. 135(2), pp. 181-186, Feb. 1998.

Boldyreff, Gastric and intestinal mucus, its properties and physiological importance, Acta Medica Scandinavica (journal), vol. 89, Issue 1-2, pp. 1-14, Jan./Dec. 1936.

Borovikova et al., Acetylcholine inhibition of immune response to bacterial endotoxin in human macrophages, Abstracts, Society for Neuroscience, 29th Annual Meeting, Miami Beach, FL, (Abs. No. 624.6); Oct. 23-28, 1999.

(56) References Cited

OTHER PUBLICATIONS

Borovikova et al., Efferent vagus nerve activity attenuates cytokine-mediated inflammation, Society for Neuroscience Abstracts, vol. 26, No. 102, Nov. 4-9, 2000 (abstract only).

Borovikova et al., Intracerebroventricular CNI-1493 prevents LPS-induced hypotension and peak serum TNF at a four-log lower dose than systemic treatment, 21st Annual Conference on Shock, San Antonio, TX, Jun. 14-17, 1998, Abstract No. 86.

Borovikova et al., Role of the efferent vagus nerve signaling in the regulation of the innate immune response to LPS, (supplemental to Shock, vol. 13, 2000, Molecular, cellular, and systemic pathobiological aspects and therapeutic approaches, abstracts, 5th World Congress on Trauma, Shock inflammation and sepsis-pathophysiology, immune consequences and therapy, Feb. 29, 2000-Mar. 4, 2000, Munich, DE), Abstract No. 166.

Borovikova et al., Role of the vagus nerve in the anti-inflammatory effects of CNI-1493, the FASEB journal, vol. 14, No. 4, 2000 (Experimental Biology 2000, San Diego, CA, Apr. 15-18, 2000, Abstract No. 97.9).

Borovikova et al., Vagotomy blocks the protective effects of I.C.V. CNI-1493 against LPS-induced shock, (Supplemental to Shock, vol. 11, 1999, Molecular, cellular, and systemic pathobioligal aspects and therapeutic approaches, absfacts and program, Fourth international Shock Congress and 22nd Annual Conference on Shock, Philadelphia, PA, Jun. 12-16, 1999), Abstract No. 277.

Borovikova, L. V., et al., Role of vagus nerve signaling in CNI-1493-mediated suppression of acute inflammation, Autonomic Neuroscience, vol. 85, No. 1-3, pp. 141-147, Dec. 20, 2000.

Borovikova, L. V., et al., Vagus nerve stimulation attenuates the systemic inflammatory response to endotoxin, Nature, vol. 405, No. 6785: pp. 458-462, May 25, 2000.

Bruchfeld et al.; Whole blood cytokine attenuation by cholinergic agonists ex vivo and relationship to vagus nerve activity in rheumatoid arthritis; J. Int. Med.; 268(1); pp. 94-101; Jul. 2010.

Bulloch et al.; Characterization of choline O-acetyltransferase (ChAT) in the BALB/C mouse spleen; Int.J.Neurosci.; 76(1-2); pp. 141-149; May 1994.

Bumgardner, G. L. et al., Transplantation and cytokines, Seminars in Liver Disease, vol. 19, No. 2, Thieme Medical Publishers; pp. 189-204, © 1999.

Burke et al., Bent pseudoknots and novel RNA inhibitors of type 1 human immunodeficiency virus (HIV-1) reverse transcriptase, J. Mol. Biol., vol. 264(4); pp. 650-666, Dec. 1996.

Bushby et al; Centiles for adult head circumference; Archives of Disease in Childhood; vol. 67(10); pp. 1286-1287; Oct. 1992.

Cano et al.; Characterization of the central nervous system innervation of the rat spleen using viral transneuronal tracing; J.Comp Neurol.; 439(1); pp. 1-18; Oct. 2001.

Caravaca et al.; A novel flexible cuff-like microelectrode for dual purpose, acute and chronic electrical interfacing with the mouse cervical vagus nerve; Journal of Neural Engineering; 14(6);066005; Nov. 1, 2017.

Carteron, N. L., Cytokines in rheumatoid arthritis: trials and tribulations, Mol. Med. Today, vol. 6(8), pp. 315-323, Aug. 2000.

Cavaillon et al.; The pro-inflammatory cytokine casade; Immune Response in the Critically Ill; Springer-Verlag Berlin Hiedelberg; pp. 37-66; Jan. 21, 2002.

Cheyuo et al.; The parasympathetic nervous system in the quest for stroke therapeutics; J. Cereb. Blood Flow Metab.; 31(5); pp. 1187-1195; May 2011.

Cicala et al., "Linkage between inflammation and coagulation: An update on the molecular basis of the crosstalk," Life Sciences, vol. 62(20); pp. 1817-1824. Apr. 1998.

Clark et al.; Enhanced recognition memory following vagus nerve stimulation in human subjects; Nat. Neurosci.; 2(1); pp. 94-98; Jan. 1999.

Cohen, "The immunopathogenesis of sepsis," Nature., vol. 420(6917): pp. 885-891, Dec. 2002.

Corcoran, et al., The effects of vagus nerve stimulation on pro- and anti-inflammatory cytokines in humans: a preliminary report, NeuroImmunoModulation, vol. 12(5), pp. 307-309, Sep. 2005.

Crusz et al.; Inflammation and cancer; advances and new agents; Nature reviews Clinical Oncology; 12(10); pp. 584-596; doi: 10.1038/nrclinonc.2015.105; Jun. 30, 2015.

Dake; Chronic cerebrospinal venous insufficiency and multiple sclerosis: Hostory and background; Techniques Vasc. Intervent. Radiol.; 15(2); pp. 94-100; Jun. 2012.

Das, Critical advances in spticemia and septic shock, Critical Care, vol. 4, pp. 290-296, Sep. 7, 2000.

Del Signore et al.; Nicotinic acetylcholine receptor subtypes in the rat sympathetic ganglion: pharmacological characterization, subcellular distribution and effect of pre- and postganglionic nerve crush; J.Neuropathol.Exp. Neurol.; 63(2); pp. 138-150; Feb. 2004.

Diamond et al.; Mapping the immunological homunculus; Proc. Natl. Acad. Sci. USA; 108(9); pp. 3461-3462; Mar. 1, 2011.

Dibbs, Z., et al., Cytokines in heart failure: pathogenetic mechanisms and potential treatment, Proc. Assoc. Am. Physicians, vol. 111, No. 5, pp. 423-428, Sep.-Oct. 1999.

Dinarello, C. A., The interleukin-1 family: 10 years of discovery, FASEB J., vol. 8, No. 15, pp. 1314-1325, Dec. 1994.

Dorr et al.; Effect of vagus nerve stimulation on serotonergic and noradrenergic transmission; J. Pharmacol. Exp. Ther.; 318(2); pp. 890-898; Aug. 2006.

Doshi et al., Evolving role of tissue factor and its pathway inhibitor, Crit. Care Med., vol. 30, suppl. 5, pp. S241-S250, May 2002.

Elenkov et al.; Stress, corticotropin-releasing hormone, glucocorticoids, and the immune / inflammatory response: acute and chronic effects; Ann. N.Y. Acad. Sci.; 876; pp. 1-13; Jun. 22, 1999.

Ellington et al., In vitro selection of RNA molecules that bind specific ligands, Nature, vol. 346, pp. 818-822, Aug. 30, 1990.

Ellrich et al.; Transcutaneous vagus nerve stimulation; Eur. Neurological Rev.; 6(4); pp. 254-256; Winter 2011.

Engineer et al.; Directing neural plasticity to understand and treat tinnitus; Hear. Res.; 295; pp. 58-66; Jan. 2013.

Engineer et al.; Reversing pathological neural activity using targeted plasticity; Nature; 470(7332); pp. 101-104; Feb. 3, 2011 (Author Manuscript).

Esmon, The protein C pathway, Crit. Care Med., vol. 28, suppl. 9, pp. S44-S48, Sep. 2000.

Fields; New culprits in chronic pain; Scientific American; pp. 50-57; Nov. 2009.

Fleshner, M., et al., Thermogenic and corticosterone responses to intravenous cytokines (IL-1? and TNF-?) are attenuated by subdiaphragmatic vagotomy, J. Neuroimmunol., vol. 86(2), pp. 134-141, Jun. 1998.

Fox, D. A., Cytokine blockade as a new strategy to treat rheumatoid arthritis, Arch. Intern. Med., vol. 160, pp. 437-444, Feb. 28, 2000.

Fox, et al., Use of muscarinic agonists in the treatment of Sjorgren' syndrome, Clin. Immunol., vol. 101, No. 3; pp. 249-263, Dec. 2001.

Fujii et al.; Simvastatin regulates non-neuronal cholinergic activity in T lymphocytes via CD11a-mediated pathways; J. Neuroimmunol.; 179(1-2); pp. 101-107; Oct. 2006.

Gao et al.; Investigation of specificity of auricular acupuncture points in regulation of autonomic function in anesthetized rats; Autonomic Neurosc.; 138(1-2); pp. 50-56; Feb. 29, 2008.

Gattorno, M., et al., Tumor necrosis factor induced adhesion molecule serum concentrations in henoch-schoenlein purpura and pediatric systemic lupus erythematosus, J. Rheumatol., vol. 27, No. 9, pp. 2251-2255, Sep. 2000.

Gaykema, R. P., et al., Subdiaphragmatic vagotomy suppresses endotoxin-induced activation of hypothalamic corticotropin-releasing hormone neurons and ACTH secretion, Endocrinology, vol. 136, No. 10, pp. 4717-4720, Oct. 1995.

Ghelardini et al., S-(−)-ET 126: A potent and selective M1 antagonist in vitro and in vivo, Life Sciences, vol. 58, No. 12, pp. 991-1000, Feb. 1996.

Ghia, et al., The vagus nerve: a tonic inhibitory influence associated with inflammatory bowel disease in a murine model, Gastroenterology, vol. 131, No. 4, pp. 1122-1130, Oct. 2006.

(56) References Cited

OTHER PUBLICATIONS

Giebelen, et al., Stimulation of ?7 cholinergic receptors inhibits lipopolysaccharide-induced neutrophil recruitment by a tumor necrosis factor ?- independent mechanism, Shock, vol. 27, No. 4, pp. 443-447, Apr. 2007.

Goyal et al., Nature of the vagal inhibitory innervation to the lower esophageal sphincter, Journal of Clinical Investigation, vol. 55, pp. 1119-1126, May 1975.

Gracie, J. A., et al., A proinflammatory role for IL-18 in rheumatoid arthritis, J. Clin. Invest., vol. 104, No. 10, pp. 1393-1401, Nov. 1999.

Granert et al., Suppression of macrophage activation with CNI-1493 increases survival in infant rats with systemic haemophilus influenzae infection, Infection and Immunity, vol. 68, No. 9, pp. 5329-5334, Sep. 2000.

Green et al., Feedback technique for deep relaxation, Psycophysiology, vol. 6, No. 3, pp. 371-377, Nov. 1969.

Gregory et al., Neutrophil-kupffer-cell interaction in host defenses to systemic infections, Immunology Today, vol. 19, No. 11, pp. 507-510, Nov. 1998.

Groves et al.; Recordings from the rat locus coeruleus during acute vagal nerve stimulation in the anaesthetised rat; Neuroscience Letters; 379(3); pp. 174-179; May 13, 2005.

Guarente, Leonard, Ph. D .; Sirtuins, Aging, and Medicine; N Engl J Med ; vol. 364:pp. 2235-2244; Jun. 2011.

Guslandi, M., Nicotine treatment for ulcerative colitis, Br. J. Clin. Pharmacol., vol. 48(4), pp. 481-484, Oct. 1999.

Hansson, E.; Could chronic pain and spread of pain sensation be induced and maintained by glial activation?. Acta Physiologica, vol. 187, Issue 1-2; p. 321R327, May/Jun. 2006.

Harrison's Principles of Internal Medicine, 13th Ed., pp. 511-515 and 1433-1435, Mar. 1994.

Hatton et al.; Vagal nerve stimulation: overview and implications for anesthesiologists; Int'l Anesthesia Research Society; vol. 103; No. 5; pp. 1241-1249; Nov. 2006.

Hirano, T., Cytokine suppresive agent improves survival rate in rats with acute pancreatitis of closed duodenal loop, J. Surg. Res., vol. 81, No. 2, pp. 224-229, Feb. 1999.

Hirao et al., The limits of specificity: an experimental analysis with RNA aptamers to MS2 coat protein variants, Mol. Divers., vol. 4, No. 2, pp. 75-89, 1999 (Accepted Jan. 13, 1999).

Hoffer et al.; Implantable electrical and mechanical interfaces with nerve and muscle; Annals of Biomedical Engineering; vol. 8; pp. 351-360; Jul. 1980.

Holladay et al., Neuronal nicotinic acetylcholine receptors as targets for drug discovery, Journal of Medicinal Chemistry, 40(26), pp. 4169-4194, Dec. 1997.

Hommes, D. W. et al., Anti- and Pro-inflammatory cytokines in the pathogenesis of tissue damage in Crohn's disease, Current Opinion in Clinical Nutrition and Metabolic Care, vol. 3(3), pp. 191-195, May 2000.

Housley et al.; Biomarkers in multiple sclerosis; Clinical Immunology; 161 (1); pp. 51-58; Nov. 2015.

Hsu, et al., Analysis of efficiency of magnetic stimulation, IEEE Trans. Biomed. Eng., vol. 50(11), pp. 1276-1285, Nov. 2003.

Hsu, H. Y., et al., Cytokine release of peripheral blood monoculear cells in children with chronic hepatitis B virus infection, J. Pediatr. Gastroenterol., vol. 29, No. 5, pp. 540-545, Nov. 1999.

Hu, et al., The effect of norepinephrine on endotoxin-mediated macrophage activation, J. Neuroimmunol., vol. 31(1), pp. 35-42, Jan. 1991.

Huston et al.; Splenectomy inactivates the cholinergic antiinflammatory pathway during lethal endotoxemia and polymicrobial sepsis; J. Exp. Med. 2006; vol. 203, No. 7; pp. 1623-1628; Jun. 19, 2006.

Huston et al.; Transcutaneous vagus nerve stimulation reduces serum high mobility group box 1 levels and improves survival in murine sepsis; Crit. Care Med.; 35(12); pp. 2762-2768; Dec. 2007.

Hutchinson et al.; Proinflammatory cytokines oppose opioid induced acute and chronic analgesia; Brain Behav Immun.; vol. 22; No. 8; pp. 1178-1189; Nov. 2008.

Ilton et al., "Differential expression of neutrophil adhesion molecules during coronary artery surgery with cardiopulmonary bypass" Journal of Thoracic and Cardiovascular Surgery, Mosby—Year Book, inc., St. Louis, Mo, US, pp. 930-937, Nov. 1, 1999.

Jaeger et al., The structure of HIV-1 reverse transcriptase complexed with an RNA pseudoknot inhibitor, The EMBO Journal, 17(15), pp. 4535-4542, Aug. 1998.

Jander, S. et al., Interleukin-18 is induced in acute inflammatory demyelinating polymeuropathy, J. Neuroimmunol., vol. 114, pp. 253-258, Mar. 2001.

Joshi et al., Potent inhibition of human immunodeficiency virus type 1 replection by template analog reverse transcriptase , J. Virol., 76(13), pp. 6545-6557, Jul. 2002.

Kalishevskaya et al. "The character of vagotomy-and atropin-induced hypercoagulation," Sechenov Physiological Journal of the USSR, 65(3): pp. 398-404, Mar. 1979.

Kalishevskaya et al.; Nervous regulation of the fluid state of the blood; Usp. Fiziol. Nauk;, vol. 13; No. 2; pp. 93-122; Apr.-Jun. 1982.

Kanai, T. et al., Interleukin-18 and Crohn's disease, Digestion, vol. 63, suppl. 1, pp. 37-42, (year of pub. sufficiently earlier than effective US filing date and any foreign priority date) 2001.

Katagiri, M., et al., Increased cytokine production by gastric mucosa in patients with helicobacter pylori infection, J. Clin, Gastroenterol., vol. 25, Suppl. 1, pp. S211-S214, 1997.

Katsavos et al.; Biomarkers in multiple sclerosis: an up-to-date overview; Multiple Sclerosis International; vol. 2013, Article ID 340508, 20 pages; (year of pub. sufficiently earlier than effective US filing date and any foreign priority date) 2013.

Kawahara et al.; SIRT6 links histone H3 lysine 9 deacetylation to NF-kappaB-dependent gene expression and organismal life span.; Cell. ; vol. 136; No. 1; pp. 62-74; Jan. 2009.

Kawashima, et al., Extraneuronal cholinergic system in lymphocytes, Pharmacology & Therapeutics, vol. 86, pp. 29-48, Apr. 2000.

Kees et al.; Via beta-adrenoceptors, stimulation of extrasplenic sympathetic nerve fibers inhibits lipopolysaccharide-induced TNF secretion in perfused rat spleen; J.Neuroimmunol.; 145(1-2); pp. 77-85; Dec. 2003.

Kensch et al., HIV-1 reverse transcriptase-pseudoknot RNA aptamer interaction has a binding affinity in the low picomolar range coupled with high specificity, J. Biol. Chem., 275(24), pp. 18271-18278, Jun. 16, 2000.

Khatun, S., et al., "Induction of hypercoagulability condition by chronic localized cold stress in rabbits," Thromb. and Haemost., 81(3): pp. 449-455, Mar. 1999.

Kimball, et al., Levamisole causes differential cytokine expression by elicited mouse peritoneal macrophases, Journal of Leukocyte Biology, vo. 52, No. 3, pp. 349-356, Sep. 1992 (abstract only).

Kimmings, A. N., et al., Systemic inflammatory response in acute cholangitis and after subsequent treatment, Eur. J. Surg., vol. 166, pp. 700-705, Sep. 2000.

Kirchner et al.; Left vagus nerve stimulation suppresses experimentally induced pain; Neurology; vol. 55; pp. 1167-1171; Oct. 2000.

Kokkula, R. et al., Successful treatment of collagen-induced arthritis in mice and rats by targeting extracellular high mobility group box chromosomal protein 1 activity, Arthritis Rheum., 48(7), pp. 2052-2058, Jul. 2003.

Koopman et al.; Pilot study of stimulation of the cholinergic anti-inflammatory pathway with an implantable vagus nerve stimulation device in patients with rheumatoid arthritis; Arth. Rheum.; 64(10 suppl.); pp. S195; Oct. 2012.

Koopman et al., Pilot study of stimulation of the cholinergic anti-inflammatory pathway with an implantable vagus nerve stimulation device in patients with rheumatoid arthritis; 2012 ACR/ARHP Annual Meeting; Abstract No. 451; 4 pages; retrieved from the internet (https://acrabstracts.org/abstract/pilot-study-of-stimulation-of-the-cholinergic-anti-inflammatory-pathway-with-an-implantable-vagus-nerve-stimulation-device-in-patients-with-rheumatoid-arthritis); (Abstract Only); on Sep. 24, 2020.

(56) References Cited

OTHER PUBLICATIONS

Koopman et al.; THU0237 first-in-human study of vagus nerve stimulation for rheumatoid arthritis: clinical and biomarker results through day 84; Annals of the Rheumatic Diseases; 72(Suppl 3):A246; Jun. 1, 2013 (Abstract Only).
Koopman et al.; Vagus nerve stimulation inhibits cytokine production and attenuates disease severity in rheumatoid arthritis; Proceedings of the National Academy of Sciences; 113(29); pp. 8284-8289; Jul. 19, 2016.
Krarup et al.; Conduction studies in peripheral cat nerve using implanted electrodes: I. methods and findings in controls; Muscle & Nerve; vol. 11; pp. 922-932; Sep. 1988.
Kudrjashov, et al. "Reflex nature of the physiological anticoagulating system," Nature, vol. 196(4855): pp. 647-649; Nov. 17, 1962.
Kumins, N. H., et al., Partial hepatectomy reduces the endotoxin-induced peak circulating level of tumor necrosis factor in rats, Shock, vol. 5, No. 5, pp. 385-388, May 1996.
Kuznik, "Role of the vascular wall in the process of hemostatis," Usp Sovrem Biol., vol. 75(1): pp. 61-85. (year of pub. sufficiently earlier than effective US filing date and any foreign priority date) 1973.
Kuznik, et al., "Blood Coagulation in stimulation of the vagus nerve in cats," Biull. Eskp. Biol. Med., vol. 78 (7): pp. 7-9, (year of pub. sufficiently earlier than effective US filing date and any foreign priority date) 1974.
Kuznik, et al., "Heart as an efferent regulator of the process of blood coagulation and fibrinolysis," Kardiologiia, vol. 13(3): pp. 10-17, (year of pub. sufficiently earlier than effective US filing date and any foreign priority date) 1973.
Kuznik, et al., "Role of the heart and vessels in regulating blood coagulation and fibrinolysis," Kagdiologiia, vol. 13(4): pp. 145-154, Apr. 1973.
Kuznik, et al., "Secretion of blood coagulation factors into saliva under conditions of hypo-and hypercoagulation, "Voprosy Meditsinskoi Khimil, vol. 19(1): pp. 54-57; (year of pub. sufficiently earlier than effective US filing date and any foreign priority date) 1973.
Kuznik, et al., "The dynamics of procoagulatible and fibrinolytic activities during electrical stimulation of peripheral nerves," Sechenov Physiological Journal of the USSR, vol. 65; No. 3: pp. 414-420, Mar. 1979.
Kuznik, et al., "The role of the vascular wall in the mechanism of control of blood coagulation and fibrinolysis on stimulation of the vagus nerve," Cor Vasa, vol. 17(2): pp. 151-158, (year of pub. sufficiently earlier than effective US filing date and any foreign priority date) 1975.
Lang, et al., "Neurogienic control of cerebral blood flow," Experimental Neurology, 43(1): pp. 143-161, Apr. 1974.
Lee, H. G., et al., Peritoneal lavage fluids stimulate NIH3T3 fibroblast proliferation and contain increased tumour necrosis factor and IL6 in experimental silica-induced rat peritonitis, Clin. Exp. Immunol., vol. 100, pp. 139-144, Apr. 1995.
LeNovere, N. et al., Molecular evolution of the nicotinic acetylcholine receptor: an example of multigene family in excitable cells, J. Mol. Evol., 40, pp. 155-172, Feb. 1995.
Leonard, S. et al., Neuronal nicotinic receptors: from structure to function, Nicotine & Tobacco Res. 3:203-223, Aug. 2001.
Lips et al.; Coexpression and spatial association of nicotinic acetylcholine receptor subunits alpha7 and alpha10 in rat sympathetic neurons; J.Mol.Neurosci.; 30; pp. 15-16; Feb. 2006.
Lipton, J. M. et al.; Anti-inflammatory actions of the neuroimmunomodulator?-MSH, Immunol. Today, vol. 18, pp. 140-145, Mar. 1997.
Loeb et al.; Cuff electrodes for chronic stimulation and recording of peripheral nerve activity; Journal of Neuroscience Methods; vol. 64; pp. 95-103; Jan. 1996.
Mayo Clinic; The factsheet of vagus nerve stimulation from the Mayo Clinic website: www.mayoclinic.org/tests-procedures/vagus-nerve-sti mulation/about/pac-20384565; retrieved from the internet on Sep. 28, 2021.
Madretsma, G. S., et al., Nicotine inhibits the in vitro production of interleukin 2 and tumour necrosis factor-alpha by human monocuclear cells, Immunopharmacology, vol. 35, No. 1, pp. 47-51, Oct. 1996.
Manta et al.; Optimization of vagus nerve stimulation parameters using the firing activity of serotonin neurons in the rat dorsal raphe; European Neuropsychopharmacology; vol. 19; pp. 250-255; Jan. 2009 (doi: 10.1016/j.euroneuro.2008.12.001).
Martindale: The Extra Pharmacopoeia; 28th Ed. London; The Pharmaceutical Press; pp. 446-485; © 1982.
Martiney et al., Prevention and treatment of experimental autoimmune encephalomyelitis by CNI-1493, a macrophage-deactivating agent, Journal of Immunology, vol. 160, No. 11, pp. 5588-5595, Jun. 1, 1998.
McGuinness, P. H., et al., Increases in intrahepatic CD68 positive cells, MAC387 positive cells, and proinflammatory cytokines (particulary interleukin 18) in chronic hepatitis C infection, Gut, vol. 46(2), pp. 260-269, Feb. 2000.
Miguel-Hidalgo, J.J.; The role of glial cells in drug abuse; Current Drug Abuse Reviews; vol. 2; No. 1; pp. 76-82; Jan. 2009.
Milligan et al.; Pathological and protective roles of glia in chronic pain; Nat Rev Neurosci.; vol. 10; No. 1; pp. 23-26; Jan. 2009.
Minnich et al.; Anti-cytokine and anti-inflammatory therapies for the treatment of severe sepsis: progress and pitfalls; Proceedings of the Nutrition Society; vol. 63(3); pp. 437-441; Aug. 2004.
Mishchenko, et al., "Coagulation of the blood and fibrinolysos in dogs during vagal stimulation," Sechenov Physiological Journal of the USSR, vol. 61(1): pp. 101-107, 1975.
Mishchenko, "The role of specific adreno-and choline-receptors of the vascular wall in the regulation of blood coagulation in the stimulation of the vagus nerve," Biull. Eskp. Biol. Med., vol. 78(8): pp. 19-22, 1974.
Molina et al., CNI-1493 attenuates hemodynamic and pro-inflammatory responses to LPS, Shock, vol. 10, No. 5, pp. 329-334, Nov. 1998.
Nadol et al., "Surgery of the Ear and Temporal Bone," Lippinkott Williams & Wilkins, 2nd Ed., 2005, (Publication date: Sep. 21, 2004), p. 580.
Nagashima et al., Thrombin-activatable fibrinolysis inhibitor (TAFI) deficiency is compatible with murine life, J. Clin. Invest., 109, pp. 101-110, Jan. 2002.
Nathan, C. F., Secretory products of macrophages, J. Clin. Invest., vol. 79 (2), pp. 319-326, Feb. 1987.
Navalkar et al.; Irbesartan, an angiotensin type 1 receptor inhibitor, regulates markers of inflammation in patients with premature atherosclerosis; Journal of the American College of Cardiology; vol. 37; No. 2; pp. 440-444; Feb. 2001.
Navzer et al.; Reversing pathological neural activity using targeted plasticity; Nature; 470(7332); pp. 101-104; Feb. 3, 2011.
Neuhaus et al.; P300 is enhanced in responders to vagus nerve stimulation for treatment of major depressive disorder; J. Affect. Disord.; 100(1-3); pp. 123-128; Jun. 2007.
Noguchi et al., Increases in Gastric acidity in response to electroacupuncture stimulation of hindlimb of anesthetized rats, Jpn. J. Physiol., 46(1), pp. 53-58, Feb. 1996.
Norton, Can ultrasound be used to stimulate nerve tissue, BioMedical Engineering OnLine, 2(1), pp. 6, Mar. 4, 2003.
Olofsson et al.; Rethinking inflammation: neural circuits in the regulation of immunity; Immunological Reviews; 248(1); pp. 188-204; Jul. 2012.
Oshinsky et al.; Non-invasive vagus nerve stimulation as treatment for trigeminal allodynia; Pain; 155(5); pp. 1037-1042; May 2014.
Palmblad et al., Dynamics of early synovial cytokine expression in rodent collagen-induced arthritis: a thereapeutic study unding a macrophage-deactivation compound, American Journal of Pathology, vol. 158, No. 2, pp. 491-500, Feb. 2, 2001.
Pateyuk, et al., "Treatment of Botkin's disease with heparin," Klin. Med., vol. 51(3): pp. 113-117, Mar. 1973.
Pavlov et al.; Controlling inflammation: the cholinergic anti-inflammatory pathway; Biochem. Soc. Trans.; 34(Pt 6); pp. 1037-1040; Dec. 2006.
Pavlov et al.; The cholinergic anti-inflammatory pathway; Brain, Behavior, and Immunity, 19; p. 493-499; Nov. 2005.

(56) References Cited

OTHER PUBLICATIONS

Palov et al.; The cholinergic anti-inflammatory pathway: a missing link in neuroimmunomodulation; Molecular Medicine; 9(5); pp. 125-134; May 2003.
Payne, J. B. et al., Nicotine effects on PGE2 and IL-1 beta release by LPS-treated human monocytes, J. Perio. Res., vol. 31, No. 2, pp. 99-104, Feb. 1996.
Peuker; The nerve supply of the human auricle; Clin. Anat.; 15(1); pp. 35-37; Jan. 2002.
Pongratz et al.; The sympathetic nervous response in inflammation; Arthritis Research and Therapy; 16(504); 12 pages; retrieved from the internet (http://arthritis-research.com/content/16/6/504) ; Jan. 2014.
Prystowsky, J. B. et al., Interleukin-1 mediates guinea pig gallbladder inflammation in vivo, J. Surg. Res., vol. 71, No. 2, pp. 123-126, Aug. 1997.
Pulkki, K. J., Cytokines and cardiomyocyte death, Ann. Med., vol. 29(4), pp. 339-343, Aug. 1997.
Pullan, R. D., et al., Transdermal nicotine for active ulcerative colitis, N. Engl. J. Med., vol. 330, No. 12, pp. 811-815, Mar. 24, 1994.
Pulvirenti et al.; Drug dependence as a disorder of neural plasticity:focus on dopamine and glutamate; Rev Neurosci.; vol. 12; No. 2; pp. 141-158; Apr./Jun. 2001.
Rahman et al.; Mammalian Sirt 1: Insights on its biological functions; Cell Communications and Signaling; vol. 9; No. 11; pp. 1-8; May 2011.
Rayner, S. A. et al., Local bioactive tumour necrosis factor (TNF) in corneal allotransplantation, Clin. Exp. Immunol., vol. 122, pp. 109-116, Oct. 2000.
Reale et al.; Treatment with an acetylcholinesterase inhibitor in alzheimer patients modulates the expression and production of the pro-inflammatory and anti-inflammatory cytokines; J. Neuroimmunology; 148(1-2); pp. 162-171; Mar. 2004.
Rinner et al.; Rat lymphocytes produce and secrete acetylcholine in dependence of differentiation and activation; J.Neuroimmunol.; 81(1-2); pp. 31-37; Jan. 1998.
Robinson et al.; Studies with the Electrocardiogram the Action of the Vagus Nerve on the Human Heart; J Exp Med; 14(3):217-234; Sep. 1911.
Romanovsky, A. A., et al., The vagus nerve in the thermoregulatory response to systemic inflammation, Am. J. Physiol., vol. 273, No. 1 (part 2), pp. R407-R413, Jul. 1, 1997.
Saghizadeh et al.; The expression of TNF? by human muscle; J. Clin. Invest.; vol. 97; No. 4; pp. 1111-1116; Feb. 15, 1996.
Saindon et al.; Effect of cervical vagotomy on sympathetic nerve responses to peripheral interleukin-1beta; Auton.Neuroscience Basic and Clinical; 87; pp. 243-248; Mar. 23, 2001.
Saito, Involvement of muscarinic M1 receptor in the central pathway of the serotonin-induced bezold-jarisch reflex in rats, J. Autonomic Nervous System, vol. 49, pp. 61-68, Sep. 1994.
Sandborn, W. J., et al., Transdermal nicotine for mildly to moderately active ulcerative colitis, Ann. Intern. Med, vol. 126, No. 5, pp. 364-371, Mar. 1, 1997.
Sato, E., et al., Acetylcholine stimulates alveolar macrophages to release inflammatory cell chemotactic activity, Am. J. Physiol., vol. 274, pp. L970-L979, Jun. 1998.
Sato, K.Z., et al., Diversity of mRNA expression for muscarinic acetylcholine receptor subtypes and neuronal nicotinic acetylcholine receptor subunits in human mononuclear leukosytes and leukernic cell lines, Neuroscience Letters, vol. 266, pp. 17-20, Apr. 30, 1999.
Scheinman, R. I., et al., Role of transcriptional activation of I?B? in mediation of immunosuppression by glucocorticoids, Science, vol. 270, No. 5234, pp. 283-286, Oct. 13, 1995.
Schneider et al., High-affinity ssDNA inhibitors of the review transcriptase of type 1 human immunodeficiency virus, Biochemistry, 34(29), pp. 9599-9610, Jul. 1995.
Shafer, Genotypic testing for human immunodeficiency virus type 1 drug resistance, Clinical Microbiology Reviews, vol. 15, pp. 247-277, Apr. 2002.

Shapiro et al.; Prospective, randomised trial of two doses of rFVIIa (NovoSeven) in haemophilia patients with inhibitors undergoing surgery; Thromb Haemost; vol. 80(5); pp. 773-778; Nov. 1998.
Sher, M. E., et al., The influence of cigarette smoking on cytokine levels in patients with inflammatory bowel disease, Inflamm. Bowel Dis., vol. 5, No. 2, pp. 73-78, May 1999.
Shi et al.; Effects of efferent vagus nerve excitation on inflammatory response in heart tissue in rats with endotoxemia; vol. 15, No. 1; pp. 26-28; Jan. 2003 (Eng. Abstract).
Snyder et al., Correction of hemophilia B in canine and murine models using recombinant adeno-associated viral vectors; Nature Medicine, 5(1), pp. 64-70, Jan. 1999.
Sokratov, et al. "The role of choline and adrenegic structures in regulation of renal excretion of hemocoagulating compounds into the urine," Sechenov Physiological Journal of the USSR, vol. 63(12): pp. 1728-1732, 1977.
Stalcup et al., Endothellal cell functions in the hemodynamic responses to stress, Annals of the New York Academy of Sciences, vol. 401, pp. 117-131, Dec. 1982.
Steinlein, New functions for nicotine acetylcholine receptors?, Behavioural Brain Res., vol. 95(1), pp. 31-35, Sep. 1998.
Sternberg, E. M., Perspectives series: cytokines and the brain 'neural-immune interactions in health and disease,' J. Clin. Invest., vol. 100, No. 22, pp. 2641-2647, Dec. 1997.
Stevens et al.; The anti-inflammatory effect of some immunosuppressive agents; J. Path.; 97(2); pp. 367-373; Feb. 1969.
Strojnik et al.; Treatment of drop foot using and implantable peroneal underknee stimulator; Scand. J. Rehab. Med.; vol. 19(1); pp. 37R43; Dec. 1986.
Strowig et al.; Inflammasomes in health and disease; Nature; vol. 481; pp. 278-286; doi: 10.1038/nature 10759; Jan. 19, 2012.
Sugano et al., Nicotine inhibits the production of inflammatory mediators in U937 cells through modulation of nuclear factor-kappaß activation, Biochemical and Biophysical Research Communications, vol. 252, No. 1, pp. 25-28, Nov. 9, 1998.
Suter et al.; Do glial cells control pain?; Neuron Glia Biol.; vol. 3; No. 3; pp. 255-268; Aug. 2007.
Swick et al.; Locus coeruleus neuronal activity in awake monkeys: relationship to auditory P300-like potentials and spontaneous EEG. Exp. Brain Res.; 101(1); pp. 86-92; Sep. 1994.
Sykes, et al., An investigation into the effect and mechanisms of action of nicotine in inflammatory bowel disease, Inflamm. Res., vol. 49, pp. 311-319, Jul. 2000.
Takeuchi et al., A comparison between chinese blended medicine "Shosefryuto" tranilast and ketotifen on the anit-allergic action in the guinea pigs, Allergy, vol. 34, No. 6, pp. 387-393, Jun. 1985 (eng. abstract).
Tekdemir et al.; A clinico-anatomic study of the auricular branch of the vagus nerve and arnold's ear-cough reflex; Surg. Radiol. Anat.; 20(4); pp. 253-257; Mar. 1998.
Toyabe, et al., Identification of nicotinic acetylcholine receptors on lymphocytes in the periphery as well as thymus in mice, Immunology, vol. 92(2), pp. 201-205, Oct. 1997.
Tracey et al., Mind over immunity, Faseb Journal, vol. 15, No. 9, pp. 1575-1576, Jul. 2001.
Tracey, K. J. et al., Anti-cachectin/TNF monoclonal antibodies prevent septic shock during lethal bacteraemia; Nature, 330: pp. 662-664, Dec. 23, 1987.
Tracey, K. J. et al., Physiology and immunology of the cholinergic antiinflammatory pathway; J Clin Invest.; vol. 117: No. 2; pp. 289-296; Feb. 2007.
Tracey, K. J. et al., Shock and tissue injury induced by recombinant human cachectin, Science, vol. 234, pp. 470-474, Oct. 24, 1986.
Tracey, K. J.; Reflex control of immunity; Nat Rev Immunol; 9(6); pp. 418-428; Jun. 2009.
Tracey, K.J., The inflammatory reflex, Nature, vol. 420, pp. 853-859, Dec. 19-26, 2002.
Tsutsui, H., et al., Pathophysiologi roles of interleukin-18 in inflammatory liver diseases; Immunol. Rev., 174:192-209, Apr. 2000.
Tuerk et al., RNA pseudoknots that inhibit human immunodeficiency virus type 1 reverse transcriptase; Proc. Natl. Acad. Sci. USA, 89, pp. 6988-6992, Aug. 1992.

(56) References Cited

OTHER PUBLICATIONS

Tuerk et al., Systematic evolution of ligands by exponential enrichment: RNA ligands to bacteriophage T4 DNA polymerase; Science, 249(4968), pp. 505-510, Aug. 3, 1990.
Van Der Horst et al.; Stressing the role of FoxO proteins in lifespan and disease; Nat Rev Mol Cell Biol.; vol. 8; No. 6; pp. 440-450; Jun. 2007.
Van Dijk, A. P., et al., Transdermal nictotine inhibits interleukin 2 synthesis by mononuclear cells derived from healthy volunteers, Eur. J. Clin. Invest, vol. 28, pp. 664-671, Aug. 1998.
Vanhoutte, et al., Muscarinic and beta-adrenergic prejunctional modulation of adrenergic neurotransmission in the blood vessel wall, Gen Pharmac, vol. 14(1), pp. 35-37, Jan. 1983.
VanWesterloo, et al., The cholinergic anti-inflammatory pathway regulates the host response during septic peritonitis, The Journal of Infectious Diseases, vol. 191, pp. 2138-2148, Jun. 15, 2005.
Ventureyra, Transcutaneous vagus nerve stimulation for partial onset seizure therapy, Child's Nerv Syst, vol. 16(2), pp. 101-102, Feb. 2000.
Vijayaraghavan, S.; Glial-neuronal interactions-implications for plasticity anddrug addictionl AAPS J.; vol. 11; No. 1; pp. 123-132; Mar. 2009.
Villa et al., Protection against lethal polymicrobial sepsis by CNI-1493, an inhibitor of pro-inflammatory cytokine synthesis, Journal of Endotoxin Research, vol. 4, No. 3, pp. 197-204, Jun. 1997.
Von Känel, et al., Effects of non-specific ?-adrenergic stimulation and blockade on blood coagulation in hypertension, J. Appl. Physiol., vol. 94, pp. 1455-1459, Apr. 2003.
Von Känel, et al., Effects of sympathetic activation by adrenergic infusions on hemostasis in vivo, Eur. J. Haematol., vol. 65: pp. 357-369, Dec. 2000.
Walland et al., Compensation of muscarinic brochial effects of talsaclidine by concomitant sympathetic activation in guinea pigs; European Journal of Pharmacology, vol. 330(2-3), pp. 213-219, Jul. 9, 1997.
Wang et al; Nicotinic acetylcholine receptor alpha7 subunit is an essential regulator of inflammation; Nature; 421; 384-388; Jan. 23, 2003.
Wang, H., et al., HMG-1 as a late mediator of endotoxin lethality in mice, Science, vol. 285, pp. 248-251, Jul. 9, 1999.
Waserman, S. et al., TNF -? dysregulation in asthma: relationship to ongoing corticosteroid therapy, Can. Respir. J., vol. 7, No. 3, pp. 229-237, May-Jun. 2000.
Watanabe, H. et al., The significance of tumor necrosis factor (TNF) levels for rejection of joint allograft, J. Reconstr. Microsurg., vol. 13, No. 3, pp. 193-197, Apr. 1997.
Wathey, J.C. et al., Numerical reconstruction of the quantal event at nicotinic synapses; Biophys. J., vol. 27: pp. 145-164, Jul. 1979.
Watkins, L.R. et al., Blockade of interleukin-1 induced hyperthermia by subdiaphragmatic vagotomy: evidence for vagal mediation of immune-brain communication, Neurosci. Lett., vol. 183(1-2), pp. 27-31, Jan. 1995.
Watkins, L.R. et al., Implications of immune-to-brain communication for sickness and pain, Proc. Natl. Acad. Sci. U.S.A., vol. 96(14), pp. 7710-7713, Jul. 6, 1999.
Webster's Dictionary, definition of "intrathecal", online version accessed Apr. 21, 2009.
Weiner, et al., "Inflammation and therapeutic vaccination in CNS diseases," Nature., vol. 420(6917): pp. 879-884, Dec. 19-26, 2002.
Westerheide et al.; Stress-inducible regulation of heat shock factor 1 by the deacetylase SIRT1.; Science; Vo. 323; No. 5717; pp. 1063-1066; Feb. 2009.
Whaley, K et al., C2 synthesis by human monocytes is modulated by a nicotinic cholinergic receptor, Nature, vol. 293, pp. 580-582, Oct. 15, 1981.
Woiciechowsky, C. et al., Sympathetic activation triggers systemic interleukin-10 release in immunodepression induced by brain injury, Nature Med., vol. 4, No. 7, pp. 808-813, Jul. 1998.
Yeh, S.S. et al., Geriatric cachexia: the role of cytokines, Am. J. Clin. Nutr., vol. 70(2), pp. 183-197, Aug. 1999.
Yu et al.; Low-level transcutaneous electrical stimulation of the auricular branch of the vagus nerve: a non-invasive approach to treat the initial phase of atrial fibrillation; Heart Rhythm; 10(3); pp. 428-435; Mar. 2013.
Zamotrinsky et al.; Vagal neurostimulation in patients with coronary artery disease; Auton. Neurosci.; 88(1-2); pp. 109-116; Apr. 2001.
Zhang et al., Tumor necrosis factor, The Cytokine Handbook, 3rd ed., Ed. Thompson, Academic Press, pp. 517-548, Jul. 1, 1998.
Zhang et al.; Chronic vagus nerve stimulation improves autonomic control and attenuates systemic inflammation and heart failure progression in a canine high-rate pacing model; Circulation Heart Fail.; 2; pp. 692-699; Nov. 2009.
Zhang et al.; Roles of SIRT1 in the acute and restorative phases following induction of inflammation.; J Biol Chem.; vol. 285; No. 53; pp. 41391-401; Dec. 2010.
Zhao et al.; Transcutaneous auricular vagus stimulation protects endotoxeric rat from lipopolysaccharide-induced inflammation; Evid. Based Complement Alternat. Med.; vol. 2012; Article ID 627023; 10 pages; Dec. 29, 2012.
Zitnik et al.; Treatment of chronic inflammatory diseases with implantable medical devices; Cleveland Clinic Journal of Medicine; 78(Suppl 1); pp. S30-S34; Aug. 2011.
Huston et al.; U.S. Appl. No. 18/355,401 entitled "Methods for reducing bleeding in hemophilia by vagus nerve stimualtion to prime platelets," filed Jul. 19, 2023.
Calle et al.; U.S. Appl. No. 18/562,283 entitled "Neurostimulation parameter authentication and expiration system for nuerostimulation," filed Nov. 17, 2023.
Levine et al.; U.S. Appl. No. 18/431,974 entitled "Vagus nerve stimulation pre-screening test," filed Feb. 3, 2024.
Huston et al.; U.S. Appl. No. 17/784,805 entitled "Treating bleeding and bleeding disorders via high intensity focused ultrasound stimulation of the spleen," filed Jun. 13, 2022.
Zitnik et al.; U.S. Appl. No. 17/875,327 entitled "Batteryless Implantable Microstimulators," filed Jul. 27, 2022.
Gautron et al.; Neurobiology of inflammation-associated anorexia; Frontiers in Neuroscience; 3(59); 10 pages; Jan. 8, 2010.
Levine; U.S. Appl. No. 18/605,809 entitled "Bimodal vagus nerve simulation to treat neurodegenerative disorders," filed Mar. 14, 2024.
Li et al.; U.S. Appl. No. 18/645,129 entitled "System and methods of stimulation at trigeminaly innervated regions for disorders of cerebral perfusion," filed Apr. 24, 2024.
Levine et al.; U.S. Appl. No. 18/664,817 entitled "Reversing demyelination," filed May 15, 2024.
Hebb et al.; Creating the Feedback Loop: Closed-Loop Neurostimulation; Neurosurgery Clinics of North America; 25(1); pp. 187-204; Jan. 28, 2014.

\* cited by examiner

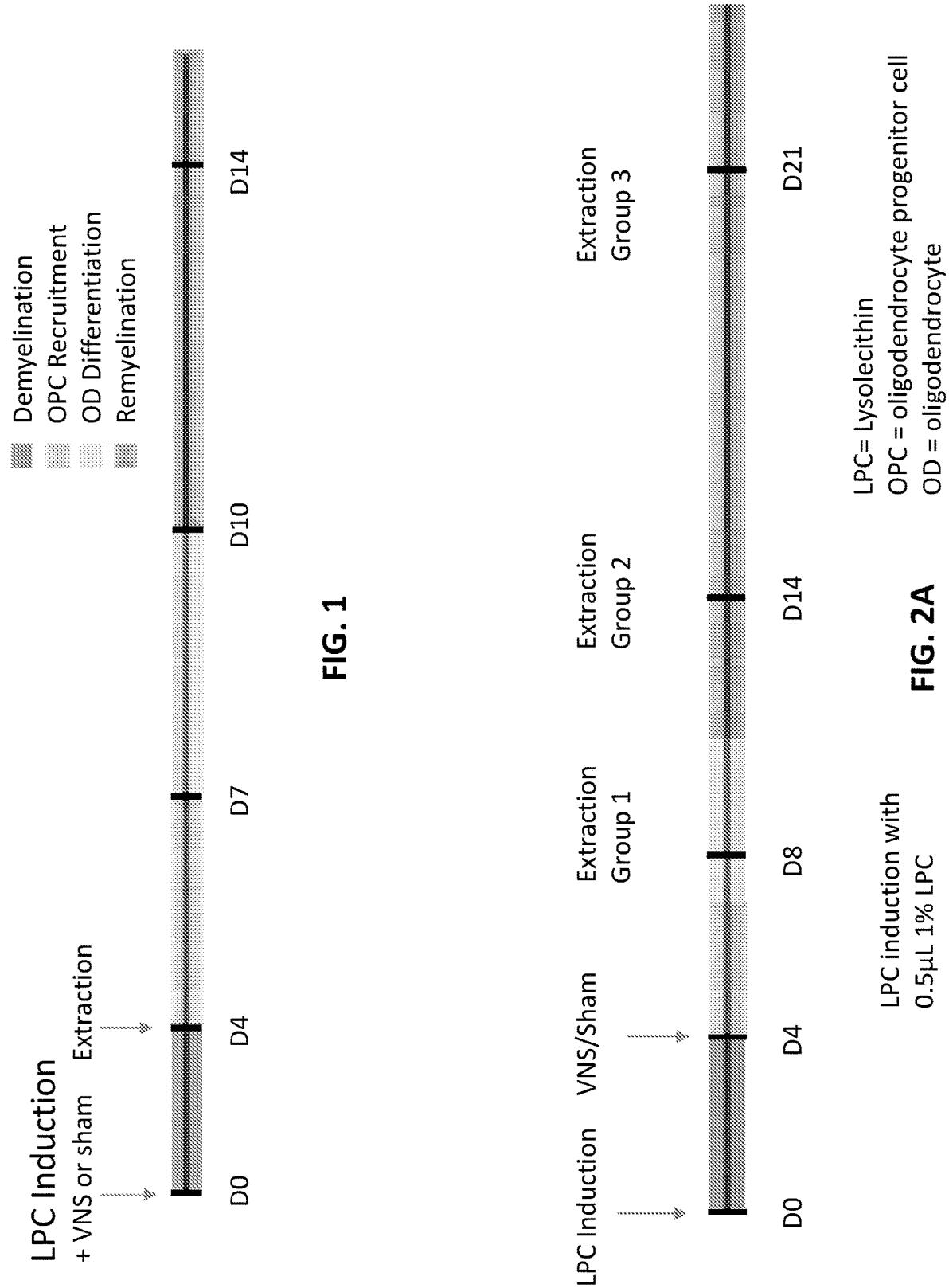

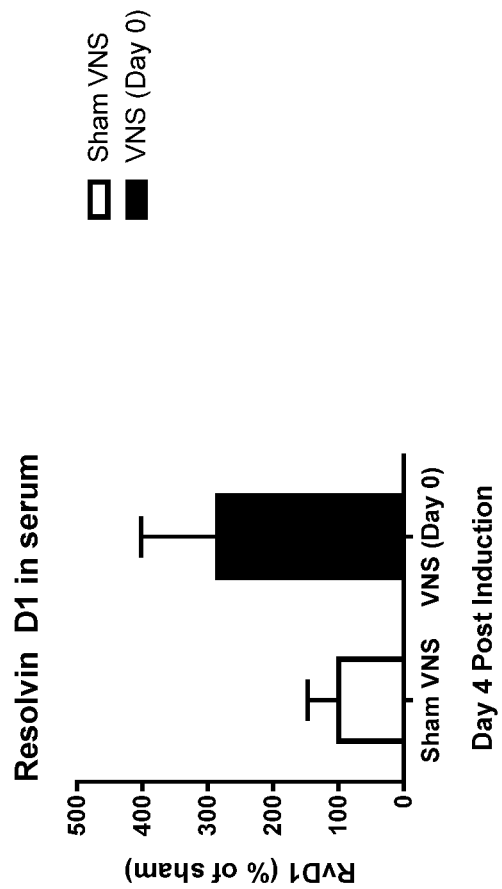
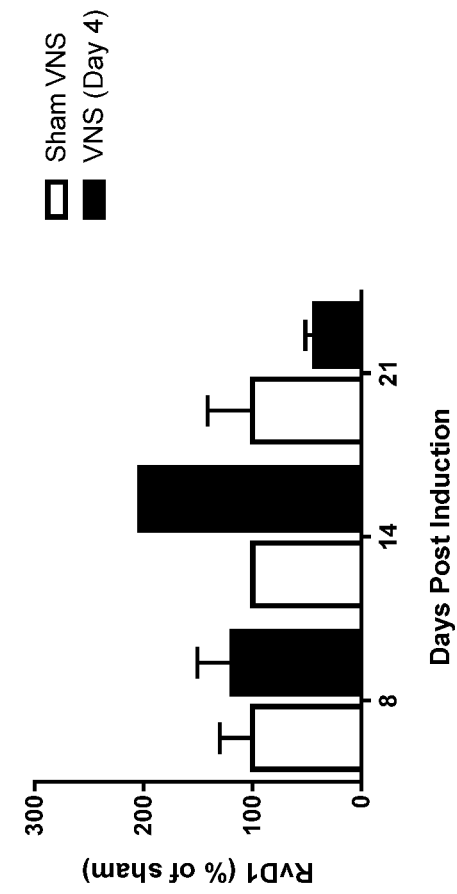
FIG. 10A
FIG. 10B

Representative Oil Red O staining
Treatment paradigm A, Day 4 post-induction

\* Box represents region of interest where lesion is located

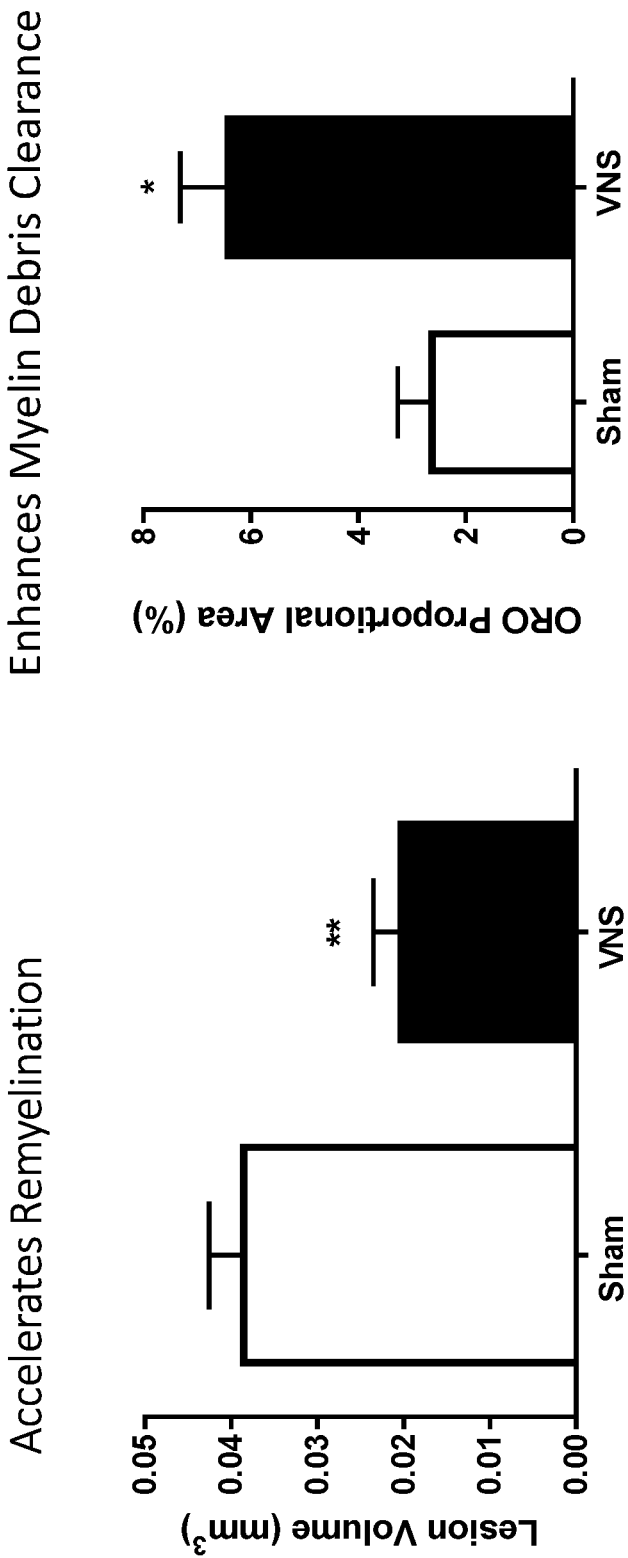

VAGUS NERVE STIMULATION TO TREAT NEURODEGENERATIVE DISORDERS

CROSS REFERENCE TO RELATED APPLICATIONS

This application is a national phase application under 35 U.S.C. 371 of International Patent Application No. PCT/US2020/027906, titled "VAGUS NERVE STIMULATION TO TREAT NEURODEGENERATIVE DISORDERS," filed Apr. 13, 2020, now International Patent Publication No. WO 2020/210786, which claims priority to U.S. provisional patent application No. 62/833,631, filed Apr. 12, 2019, titled "VAGUS NERVE STIMULATION TO TREAT NEURODEGENERATIVE DISORDERS," each of which is herein incorporated by reference in its entirety.

This patent application may be related to U.S. patent application Ser. No. 16/158,222 filed on Oct. 11, 2018, titled "VAGUS NERVE STIMULATION TO TREAT NEURODEGENERATIVE DISORDERS," which claims priority to U.S. provisional patent application No. 62/572,374, filed on Oct. 13, 2017, titled "VAGUS NERVE STIMULATION TO TREAT NEURODEGENERATIVE DISORDERS," and U.S. provisional patent application No. 62/576,547, filed Oct. 24, 2017, titled "VAGUS NERVE STIMULATION TO TREAT NEURODEGENERATIVE DISORDERS," each of which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

Embodiments of the invention relate generally to apparatuses (e.g., devices, systems) and methods for vagus nerve stimulation to treat neurodegenerative and neuroinflammatory disorders, and more specifically apparatuses and methods for vagus nerve stimulation to reduce demyelination (e.g., by preventing the immune cell infiltration into the CNS) and/or to promote remyelination to treat various neurodegenerative and neuroinflammatory disorders such as multiple sclerosis.

BACKGROUND

A variety of central nervous system (CNS) demyelinating disorders, including multiple sclerosis, acute disseminated encephalomyelitis and neuromyelitis optica spectrum disorders, are difficult to effectively treat. For example, multiple sclerosis (MS) is a neurodegenerative and neuroinflammatory disease characterized by demyelination of nerves in the central nervous system. Although the root cause of demyelination is not well understood, it generally is associated with the formation of lesions on the myelin sheaths and inflammation. Currently, there is no known cure for MS. Current treatments, with modest success, are primarily directed to treating acute attacks and reducing the frequency of attacks in the relapsing-remitting subtype of the disease or treating the symptoms. However, current therapies at best only slow the progression of the disease, and no therapy to date has demonstrated an ability to remyelinate nerves.

Therefore, it would be desirable to provide additional treatment methods and systems that can be used independently or in conjunction with other therapies to reduce the rate or amount of demyelination. Furthermore, it would desirable to provide a therapy that remyelinates nerves and reverses the progression demyelination.

SUMMARY OF THE DISCLOSURE

The present invention relates generally to vagus nerve stimulation to treat neurodegenerative and neuroinflammatory disorders, and more specifically to vagus nerve stimulation to reduce demyelination and/or to promote remyelination to treat various neurodegenerative and neuroinflammatory disorders such as multiple sclerosis.

For example, described herein are apparatuses (e.g., devices and/or systems) for reducing demyelination and/or increase remyelination by stimulation of a vagus nerve. These apparatuses may be implants or implanted into the patient's body. Any of these apparatuses may include: a biosensor configured to detect one or more biomarkers; a stimulator configured to apply stimulation to the vagus nerve; and a controller coupled to the biosensor and the stimulator and configured to apply stimulation to the vagus nerve from the stimulator sufficient to reduce demyelination and/or increase remyelination of nerves within the patient when the biosensor detects a biomarker indicative of demyelination. In some variations, these apparatuses include an implant comprising a stimulator (e.g., a waveform and/or pulse generator, an oscillator, a power supply and/or power regulation circuit, etc.), a stimulation applicator (e.g., one or more electrodes, mechanical transducers, etc.), and a controller. The controller may be configured as a microcontroller and may be in electrical communication with the stimulator so as to control operation of the stimulator. The controller may include one or more processors, a memory and/or a timer. The stimulator and/or controller may be in electrical communication, one or more stimulation applicators. In some variations the controller may include or be in communication with wireless communications circuitry for wirelessly communicating with one or more remote processors. The remote processor may be a hand-held device (e.g., smartphone, wearable electronics, etc.). The controller may optionally be in communication with one or more biosensors that may be included with the implant or may be remote from the implant (e.g., may be wearable, single-use, etc.). In some variations the biosensors are wirelessly connected to the apparatus.

In some variations the apparatus may be used without a biosensor. For example, the apparatus may be configured to periodically and/or on demand apply VNS treatment to prevent or reduce demyelination. The apparatus may be configured to apply VNS treatment doses once multiple times per day (e.g., 1× day, 2×, day, 3×, day, 4× day, 5× day, 6× day), or every other day, or every 3 days, etc. In some variations the apparatus may be configured to both automatically apply a VNS treatment dose on a predetermined and/or adjustable scheduled, as well as provide VNS treatment doses based on input from a user (e.g., patient, physician, etc., including "on demand" doses) and/or based on detection of a biomarker indicative of an actual or potential increase in demyelination.

In any of these variations, a biosensor may be configured to detect one or more markers (e.g., biomarkers) from the patient's body, including from the patient's blood and/or cerebrospinal fluid. Examples of biomarkers may be found herein. The biosensor may be part of the implanted apparatus, or it may be connected to the apparatus (e.g., the controller) via a wired or wireless communication. The biosensor may be configured to detect any biological marker, including chemical markers (e.g., a protein, nucleotide, e.g., RNA, DNA, microRNA, etc., lipid, carbohydrate, etc.), as well as functional markers (nerve conduction, etc.), body temperature, and the like. For example, in some variations, the biosensor is configured to detect temperature.

In general, the apparatuses described herein may be configured to be inserted or implanted into the body. For example, the apparatus may be configured to be implanted. The apparatus may include a stimulation applicator (also referred to as simply a stimulator or a VNS treatment stimulator) that may be a mechanical and/or electrical stimulator. A mechanical stimulator may be a piezoelectric driver that may vibrate and/or apply pressure to the tissue, including to the vagus nerve, in the VNS treatment parameters, such as mechanical stimulation of the vagus nerve at between 1-2 kHz for a treatment time (e.g., between 1 ms and 5 minutes, e.g., 10 ms-10 sec, etc.). Alternatively or additionally, the stimulation applicator may be an electrical stimulation applicator and may include one or more (e.g., two or more) electrodes configured to apply electrical stimulation to the vagus nerve. For example, electrical stimulation of about 0.1 mA to 10 mA (e.g., between 1 mA-5 mA), at a frequency of between about 1 Hz and about 2 kHz (e.g., between about 1-100 Hz), where the pulses applied have a pulse width of between about (50-500 usec, e.g., between about 100-300 usec). The controller may be configured to enforce an 'off-time' following a VNS treatment dose of between about 10 minute and 12 hours (e.g., between about 2 hours and 10 hours, between about 3 hours and 6 hours, at least 2 hours, at least 3 hours, at least 4 hours, at least 5 hours, at least 6 hours, etc.). For example, the stimulator may include an electrode configured to apply electrical energy to the vagus nerve.

In some variation the apparatus is configured to apply VNS treatment to the patient in which the VNS treatment is electrical stimulation. For example, the VNS treatment may include the application of electrical energy at between about 1-100 Hz (e.g., between about 1-50 Hz, between about 1-20 Hz, between about 5-30 Hz, between about 5-15 Hz, approximately 5 Hz, approximately 10 Hz, approximately 15 Hz, etc.). The energy may have a peak amplitude of between about 0.1 mA and about 2 mA (e.g., between about 0.2 mA and about 1.8 mA, between about 0.5 mA and about 1.5 mA, between about 0.5 mA and about 1 mA, between about 0.1 mA and about 1 mA, approximately 0.5 mA, approximately 0.75 mA, approximately 1 mA, etc.). Alternatively the applied energy may have an average amplitude of between about 0.1 mA and about 2 mA (e.g., between about 0.2 mA and about 1.8 mA, between about 0.5 mA and about 1.5 mA, between about 0.5 mA and about 1 mA, between about 0.1 mA and about 1 mA, approximately 0.5 mA, approximately 0.75 mA, approximately 1 mA, etc.). The applied energy is typically pulsed, and may be pulsed square waves, sinusoidal waves, triangular waves, etc. The applied energy may be biphasic or monophasic. For example, the applied energy may be biphasic. The applied VNS treatment may be a constant biphasic pulse train having a frequency of between 1-100 Hz (e.g., 10 Hz) and a peak amplitude of between about 0.5 mA and 2 mA (e.g., approximately 0.75 mA). Any of the methods for treatment described herein may be configured to apply this type of VNS treatment.

Any of the apparatuses (e.g., devices, systems, etc.) described herein may be configured to be implanted on the vagus nerve. Thus, any of these apparatuses may be implanted via a nerve sheath or nerve cuff configured to secure the apparatus onto the nerve and/or prevent movement of the apparatus relative to the nerve and/or insulate the apparatus from other tissues. The implanted apparatus may be implanted in any appropriate location on the nerve, including one or around the vagus nerve at the upper chest, or on or around the vagus nerve at a subdiaphragmatic location. The implant may be a leadless implant that is connected to the vagus (see, e.g., U.S. Pat. Nos. 8,412,338, 8,612,002, 8,886,339, and 8,788,034, each of which is herein incorporated by reference in its entirety). For example, any of these apparatuses may include a nerve cuff configured to secure the stimulator to the vagus nerve. Alternatively, any of these apparatuses may include a lead connecting the micro stimulator and/or other components to the stimulation applicator on/around the vagus nerve via one or more leads.

As mentioned, any of these apparatuses may be configured to apply VNS treatment comprising a low duty-cycle electrical stimulation of between about 0.25 mA and about 5 mA to the vagus nerve for less than about 2 minutes. The apparatus may be configured to provide an off-time of at least x minutes/hours (e.g., 10 minutes, 20 minutes, 30 minutes, 40 minutes, 60 minutes, 2 hours, 3 hours, 4 hours, etc.).

Any of the apparatuses described herein may be configured to perform a method of reducing demyelination in a patient diagnosed with or at risk of a disorder involving demyelinated nerves (e.g., including but not limited to methods of treating a disorder and/or disease associated with demyelination, such as multiple sclerosis). For example, a method of reducing demyelination (and/or a method of increasing remyelination) may be a method comprising detecting a marker for demyelination and applying stimulation to the vagus nerve to reduce demyelination of nerves within the patent.

Applying stimulation to the vagus nerve includes applying VNS treatment and may comprise, for example, applying electrical stimulation of between about 0.25 and about 5 mA to the vagus nerve for less than about 2 minutes. In some variations this may include waiting for an off-time (e.g., an off-time of at least 10 minutes, 30 minutes, 1 hour, 2 hours, 3 hours, 4 hours, etc.).

Any of these methods may include applying non-invasive stimulation to the vagus nerve. For example, the simulation may be through a transdermal (e.g., via a surface electrode and/or mechanical stimulation, including ultrasound) route over a portion of the vagus nerve. The vagus nerve includes a number of branches or extensions that may be accessed and/or targeted from outside of the body either mechanically and/or electrically. For example, non-invasive application may include ultrasound stimulation of the vagus nerve. Any of these methods may include applying transdermal electrical stimulation (TENS), or the like.

Any of the methods described herein may include monitoring, e.g., periodically, on demand, and/or continuously, one or more markers (e.g., biomarkers) for demyelination or a risk of demyelination. As mentioned, any appropriate method or apparatus for monitoring demyelination or a risk of demyelination may be used. For example any of these methods may include detecting a marker for demyelination comprising monitoring the patient's temperature. A change (including an increase) in core body temperature has been linked to an increase in symptoms in demyelination disorders, including but not limited to MS.

Any of the methods and apparatuses described herein may be used with or linked to markers for the integrity of the blood-brain barrier. The methods and apparatuses described herein generally improve the integrity of the blood-brain barrier. Thus, any marker linked to leakage or loss of integrity of the blood-brain barrier may be used to trigger VNS therapy as described herein. Examples of markers may include Serum S100β, as well as imaging modalities such as contrast-enhanced magnetic resonance imaging, CT-scan and lumbar puncture.

A detection of one or more markers (e.g., biomarkers) for demyelination may include determining a level of tumor necrosis factor in a blood or cerebrospinal fluid sample.

For example, described herein are methods (e.g., methods of treating a demyelination disorder, such as but not limited to MS, and/or methods of reducing or reversing demyelination) that include: detecting demyelination in a patient, and applying stimulation to the vagus nerve to increase the remyelination of nerves within the patent.

For example, any of these methods may include repeatedly applying a low duty-cycle electrical stimulation of between about 0.25 and about 5 mA to the patient's vagus nerve for less than about 2 minutes, followed by an off-time (e.g., of between about 10 minutes and about 48 hours) before the next stimulation.

Any of these methods and apparatuses may also include or be adapted to include the concurrent (immediately before, during or after, including systemically and/or locally) treatment with one or more pharmacological agents, particularly those that are believed to help with a demyelinating condition, such as (but not limited to) MS. For example, any of these method may include concurrently treating with a pharmacological agent such as one or more of: interferon beta-1a, interferon beta-1b, glatiramer acetate, glatiramer acetate, peginterferon beta-1a, daclizumab, teriflunomide, fingolimod, dimethyl fumarate, alemtuzumab, mitoxantrone, ocrelizumab, natalizumab.

As mentioned, any of the methods and apparatuses described herein may include continuously monitoring the patient for demyelination or a condition implicated in demyelination. For example, any of these methods and apparatuses described herein may include monitoring the patient for a marker related to a diseased selected from the group consisting of neurodegenerative diseases, neuroinflammatory diseases, and neuropathies. In some examples, the method includes detecting demyelination in a patient by detecting a marker related to MS. For example, the marker (e.g., biomarker) may be selected from the group including: neurofilament, glial fibrillary acidic protein, the monocyte macrophage marker CD163, the glial activation marker YKL-40, the B cell chemoattractant CXCL13, miRNA, mRNA, myelin reactive t cells, Kir4.1 antibodies, osteopontin, and microbiome associated lipopeptides.

In particular, described herein are methods and apparatuses for reducing or preventing demyelination and/or for increasing remyelination by stimulation of a vagus nerve. For example, an apparatus (e.g., a system, device, assembly, etc., including implants), may include: a vagus nerve stimulator configured to be implanted over or adjacent to a vagus nerve; one or more electrodes on the vagus nerve stimulator configured to apply electrical stimulation to the vagus nerve; and a controller coupled to the vagus nerve stimulator and configured to apply electrical stimulation to the vagus nerve from the one or more electrodes, wherein the controller is constrained to apply a charge per day of between 2.5 nC and 7.5 mC to reduce demyelination and/or increase remyelination within the patient. This apparatus may be system.

The system may include an input configured to receive one or more marker level indicators, wherein the controller is configured to adjust the applied charge based on the one or more marker level indicators. For example, the system may include a biosensor is configured to detect the marker from the patient's blood and/or cerebrospinal fluid and to determine a maker level indicator.

The controller may be configured to deliver the electrical stimulation during one or more dose sessions of about 5 minutes or less (e.g., 4 min or less, 3 min or less, 2 min or less, 1 min or less, etc.). The controller may be configured to apply the charge per day at a frequency of between 1 and 20 Hz. In some variations the controller is configured to apply the charge per day at a frequency of between 1 and 12 Hz.

In any of these apparatuses, the system is configured to be implanted.

Any of these systems may include a nerve cuff configured to secure the vagus nerve stimulator to the vagus nerve. The controller may be configured to apply the charge per day at two distinct frequencies between 1 and 20 Hz. The controller may be configured to apply a first dose of the electrical stimulation to reduce demyelination at a first frequency between 1 and 20 Hz, and a second dose of electrical stimulation to increase remyelination within the patient at a second frequency that is higher than the first frequency. For example, the first dose of electrical stimulation may have a frequency less than 10 Hz, and the second dose of electrical stimulation has a frequency ranging from 10 Hz and 30 Hz. In some variations the first dose of electrical stimulation has a frequency of ranging from 1 Hz and 5 Hz, and the second dose of electrical stimulation has a frequency ranging from 10 Hz and 30 Hz.

Also described herein are method of increasing clearance of myelin debris in a patient diagnosed with or at risk of a disorder involving demyelinated nerves, the method comprising applying vagus nerve stimulation to the patient of between 2.5 nC to 7.5 mC per day. The Applying may comprise applying the vagus nerve stimulation at between 0.1 and 20 Hz to the vagus nerve. In some variations, applying comprises applying a the vagus nerve stimulation for less than about 5 minute each day (e.g., less than about 4 min per day, less than about 3 min per day, less than about 2 min per day, less than about 1 min per day, etc.). Applying may comprise applying stimulation to the vagus nerve from an implanted neurostimulator attached or adjacent to the vagus nerve.

Any of these methods may include adjusting the applied vagus nerve stimulation based on the level of a marker. For example, the method may include detecting a marker for demyelination in a blood, sputum, and/or cerebrospinal fluid sample.

A system for reducing demyelination and/or increasing remyelination by stimulation of a vagus nerve may include: a vagus nerve stimulator configured to be implanted over or adjacent to a vagus nerve; one or more electrodes on the vagus nerve stimulator configured to apply electrical stimulation to the vagus nerve; and a controller coupled to the vagus nerve stimulator and configured to apply electrical stimulation to the vagus nerve from the one or more electrodes, wherein the controller is constrained to apply a low duty-cycle electrical stimulation for a duration of between 1 second and 5 minutes per day, the electrical stimulation comprising a first dose of electrical stimulation to reduce demyelination at a first frequency of between 1 and 20 Hz, and a second dose of electrical stimulation to increase remyelination at a second frequency that is higher than the first frequency.

The controller may be configured to apply electrical stimulation between 1 and 24 times per day. The frequency of the first dose of electrical stimulation may be between 1 Hz to 10 Hz. The frequency of the first dose of electrical stimulation may be between 1 Hz to 5 Hz. The frequency of the second dose of electrical stimulation may be between 10 Hz to 30 Hz. The first dose of electrical stimulation may have a frequency less than 5 Hz, and the second dose of electrical stimulation may have a frequency ranging from 10 Hz and 30 Hz.

As mentioned, the controller may be configured to modulate the electrical stimulation based on feedback from a user or based on one or more biomarkers associated with demyelination. The controller may be configured to reduce the frequency of the electrical stimulation based on the feedback. For example, a controller may be configured to adjust the duration of the first dose and the second dose based on the feedback.

A method of reducing demyelination and/or increasing remyelination in a patient having a disorder involving demyelinated nerves may include: applying a low duty-cycle electrical stimulation for a total duration of between 1 second and 5 minutes per day, the electrical stimulation comprising a first dose of electrical stimulation to reduce demyelination at a first frequency of between 1 and 20 Hz, and a second dose of electrical stimulation to increase remyelination at a second frequency that is higher than the first frequency. The low duty-cycle electrical stimulation may be applied, e.g., from 1 to 24 times per day.

The first frequency may range from 1 Hz to 10 Hz. In some variations, the first frequency ranges from 1 Hz to 5 Hz. The second frequency may range from 10 Hz to 30 Hz. The first dose of electrical stimulation may have a frequency less than 5 Hz, and the second dose of electrical stimulation may have a frequency ranging from 10 Hz and 30 Hz.

Any of these method may also include modulating the electrical stimulation based on feedback from a user or based on one or more biomarkers associated with demyelination. The controller may be configured to adjust the duration of the first dose and the second dose based on the feedback.

As described herein, any of these methods may include concurrently administering one or more of an Interferon β drug, glatiramer acetate, and daclizumab in combination with applying the low duty-cycle electrical stimulation to target interferon β-1a and 1b receptors and T-cell activation to reduce central nervous system inflammation and demyelination. For example, any of these methods may include administering one or more of fingolimod, teriflunomide, and dimethyl fumarate in combination with applying the low duty-cycle electrical stimulation to target lymphocyte migration or activation to reduce central nervous system inflammation and demyelination. Any of these methods may include administering one or more of mitoxantrone, alemtuzumab, ocrelizumab, and natalizumab in combination with applying the low duty-cycle electrical stimulation to induce DNA breakage, CD52 to induce cell lysis, B-cell CD20 antigen for depletion, and/or integrin receptors to alter leukocyte migration, to reduce central nervous system inflammation and demyelination. In some variations, these methods may include administering one or more of clemastine, a Selective Estrogen Receptor Modulator (SERM), and other drugs targeting oligodentrocyte progenitor cells to enhance maturation into myelin-producing oligodendrocytes to enhance remyelination and clinical recovery from central nervous system damage.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1 illustrates a typical example of the 4 epochs that follow lysolecithin injection to the spinal cord in a model used to study multiple sclerosis.

FIGS. 2A and 2B illustrate the experimental protocols used to study demyelination and remyelination.

FIG. 4A is a graph showing the effect of vagal nerve stimulation (VNS) on demyelination with various levels of stimulation (O mA, 0.25 mA, and 0.75 mA) four days following inducing of a demyelinating lesion. FIG. B shows the increase in remyelination by two weeks after inducing the demyelinating lesion without VNS treatment (0 mA) and with VNS treatment (0.75 mA), showing a rapid remyelination when VNS is applied. FIG. 4C is a 3D graph of the lesion size variation by depth at four days post induction of the demyelinating lesion with and without VNS treatment. FIG. 4D is a 2D projection graph of the median lesion four days post-induction of the demyelinating lesion comparing sham (no VNS treatment) and VNS treatment.

FIG. 5A is a graph showing the change in demyelination (determined by the change in induced lesion volume) following induction of demyelination with and without VNS treatment, showing an approximately 65% reduction in the area under the lesion volume ($mm^3$)/days post induction. FIG. 5B is a 3D representation of the demyelination (lesion) size variation with depth for no VNS treatment (sham) and VNS treatment. FIG. 5C is a 2D projection of median lesion volume eight days post-induction of demyelination (e.g., lesion) with VNS treatment and without VNS treatment (sham). FIG. 5D is a 3D representation of demyelination (lesion size) variation with depth at day 14 following inducing of demyelination (day 14 post induction) with VNS treatment (VNS) and without VNS treatment (sham). FIG. 5E is a 2D projection of median demyelination (lesion) at two weeks post-induction of demyelination with VNS treatment and without VNS treatment ("sham"). FIG. 5F is a 3D representation of demyelination (lesion size) variation with depth at day 21 following inducing of demyelination (day 14 post induction) with VNS treatment (VNS) and without VNS treatment (sham). FIG. 5G is a 2D projection of median demyelination (lesion) at three weeks post-induction of demyelination with VNS treatment and without VNS treatment ("sham").

FIG. 9 illustrates macrophage infiltration through a model of the blood-brain barrier is significantly decreased 24 hours post-demyelination induction (e.g., via LPC) with VNS treatment compared to sham (no VNS treatment) by 55%.

FIGS. 10A and 10B illustrate the effect of pro-resolution lipid Resolvin D1 following induction of demyelination with VNS treatment (VNS) and without VNS treatment (sham), showing Resolvin D1 (RvD1) is increased in VNS animals 4 days post-LPC induction compared to Sham animals and remains elevated 14 days post-LPC induction. Levels were decreased below that of the Sham 21 days post-LPC induction, by which time, no visible lesion is detected in VNS animals.

FIG. 20 illustrates a 34% reduction in lesion volume in the VNS group relative to the sham group on day 10 post-induction in aged mice.

FIG. 21 illustrates a 2.4× fold increase in oil red O staining as a % of lesion for the VNS group compared to the sham group (p<0.05) on day 10 in aged mice.

DETAILED DESCRIPTION

Figure 2B:
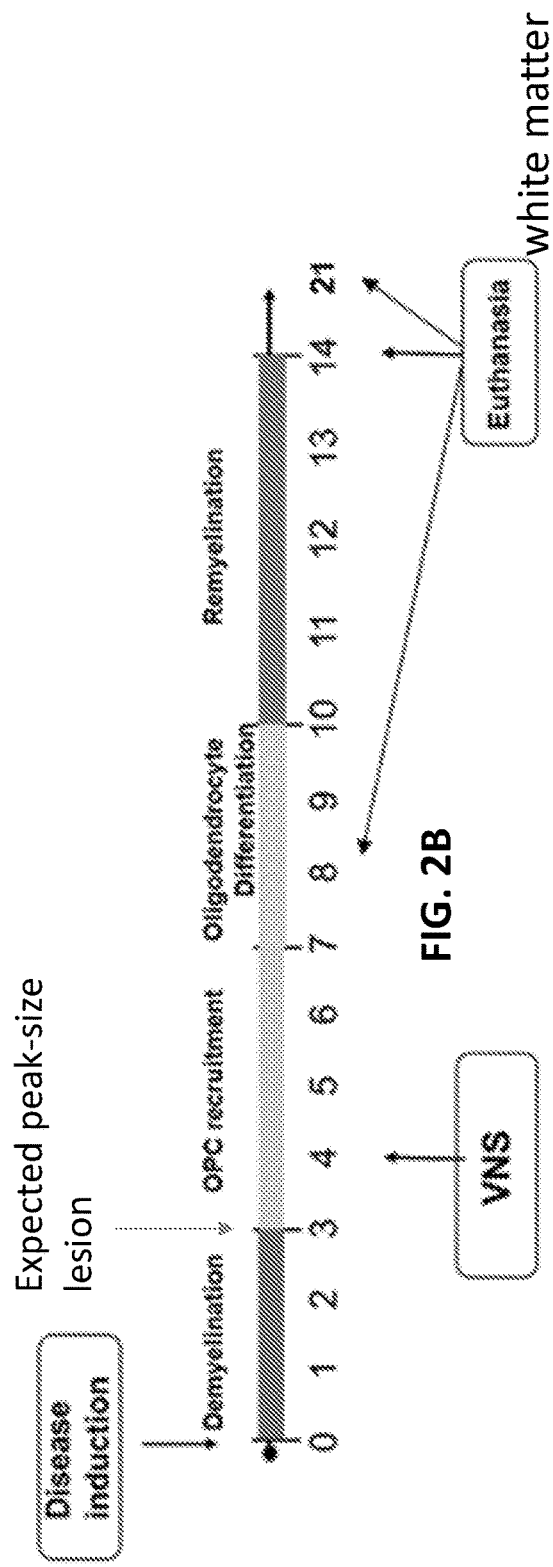

Electrical and/or mechanical stimulation of the cholinergic anti-inflammatory pathway (NCAP) by stimulation of the carotid vagus nerve been well described. For example, see U.S. Pat. Nos. 6,838,471, 8,914,114, 9,211,409, 6,610,713, 8,412,338, 8,996,116, 8,612,002, 9,162,064, 8,855,767, 8,886,339, 9,174,041, 8,788,034 and 9,211,410, each of which is herein incorporated by reference in its entirety. It has not previously been suggested that vagus nerve stimulation may be used to prevent or reduce demyelination and/or improve remyelination. Vagus nerve stimulation, through activation of both efferent and afferent pathways (or primarily through one of the efferent or afferent pathway), may be able to reduce the inflammation associated with inflammatory diseases and disorders, thereby reducing the severity of the symptoms and/or slowing, stopping, or reversing the progression of the disease. Applicants have surprisingly found that the apparatuses (e.g., systems, devices, etc.) and methods described herein may be used to stimulate the vagus nerve to reduce demyelination and/or to increase or promote remyelination. Furthermore, although the use of VNS treatment to modulate inflammation has been thought to involve afferent pathways, remyelination and demyelination may involve the efferent pathway or both the afferent and efferent pathways.

Diseases (e.g., diseases and disorder of myelination) which may benefit from VNS as described herein (e.g., the methods and apparatuses described herein) include, but are not limited to, multiple sclerosis (MS), Alzheimer's disease, Parkinson's disease, Huntington's disease, Amyotrophic lateral sclerosis (ALS), chronic inflammatory demyelinating polyneuropathy (CIDP), and Batten disease. Other neuroinflammatory disorders may include: acute disseminated encephalomyelitis (ADEM), acute optic neuritis (AON), transverse myelitis, and Neuromyelitis optica (NMO). Neuropathies that may benefit from VNS include peripheral neuropathies, cranial neuropathies, and autonomic neuropathies. Thus any of the methods and apparatuses described herein may be used (and adapted for) treatment with any of these diseases and neuropathies.

Vagus Nerve Stimulation Systems and Devices

In some variations the devices described herein are electrical stimulation devices that may be implanted, and may be activated to apply current for a proscribed duration, followed by a period without stimulation. As described in the examples that follow, the stimulation protocol may comprise a very limited period of stimulation (e.g., an on-time of less than 5 minutes, 2 minutes, 1 minute, etc.) followed by an off-time (during which stimulation is not applied, and may be prevented from being applied) of extensive duration (e.g., greater than 10 minutes, 20 minutes, 30 minutes, 40 minutes, 50 minutes, 1 hour, 1.5 hours, 2 hours, 4 hours, 12 hours, greater than 20 hours, greater than 24 hours, greater than 36 hours, greater than 48 hours, etc.). The applied energy may be electrical energy that is a fixed current having a frequency that is within the range of about 0.5 mA to 5 mA (e.g., approximately 2 mA), at a frequency of between about 1 Hz and about 1000 Hz (e.g., between 1 Hz and 100 Hz, between 1 Hz and 30 Hz, between 10 Hz and 200 Hz, etc.), where the pulses applied have a pulse width of approximately (50-500 usec, e.g., a 200 usec pulse). Thus, the duty-cycle of the applied current may be extremely low, where duty cycle may refer to the ratio of on-time/(on-time plus off-time). The stimulation is applied at an extremely low duty cycle, where duty cycle may refer to the percent of on-time to the total on-time and off-time for the ongoing treatment. For example, low duty cycle may be less than about 10, 5, 4, 3, 2, 1, or 0.5 percent of on-time to the total on time and off-time. The effect may be seen relatively quickly, and may persist over the entire off-time.

In particular, the methods and apparatuses described herein may be applied as needed, e.g., when the patient expresses or is likely to express an increased risk for demyelination and/or is experiencing (or has experienced) demyelination. Alternatively or additionally, the methods an apparatuses may be applied as needed when the patient expresses or is likely to express, and/or is experiencing (or has experienced) a leakage through the blood-brain barrier.

For example, we show herein that a low level, low duty cycle stimulation protocol (as described herein) reduces demyelination and/or increases remyelination, and prevents and/or reduces leakage through the blood-brain barrier. The effectiveness of low level, low duty cycle vagus nerve stimulation (VNS therapy) administered on even a single day results in a reduction in demyelination and an increase in remyelination seen over the course of two to three weeks. This type of stimulation contrasts with the use of a high duty cycle stimulation used by others to modulate vagus-nerve mediated functions (such as heart rate, etc.), or treat disorders such as epilepsy and depression. An important finding here is that demyelination can be reduced and even more surprisingly, remyelination can be increased. This effect is corroborated at these low duty cycle parameters by examining the histology of the spinal cord as described later below. Although low duty cycle vagus nerve stimulation is effective and highly efficient at reducing inflammation, in some embodiments, a higher duty cycle stimulation can be used, such as a duty cycle that is greater than about 1, 2, 3, 4, 5, 10, 20, 30, 40, or 50 percent of on-time to the total on-time and off-time.

MS patients may experience circadian pattern disruptions to symptoms that may be associated with or caused in part by the circadian patterns of IL-6 levels. Optionally, drugs, such as steroids, can be used along with VNS to suppress nighttime spiking of IL-6. Similarly, VNS can be modulated, by altering the timing of the stimulations for example, to suppress nighttime spiking of IL-6 more effectively. However, one advantage of VNS is the relatively long duration of the effect after a single stimulation, which may allow suppression of IL-6 levels during both night and day, which may render unnecessary the need for supplementary drug treatment or alternative timings. In some embodiments, VNS can be given in the evening before sleep, such as 15, 30, 45, 60, 90, 120, 150, or 180 minutes before sleep, and may also be given at night during sleep, to ensure nighttime suppression of IL-6 levels. In some embodiments, the amplitude of stimulation during sleep can be lowered (e.g., less than 2, 1.5, or 1 mA) to avoid waking the patient. In some embodiments, IL-6 levels can be measured and/or monitored, and VNS can be modulated based on the measured and/or monitored IL-6 levels. Other cytokines may also be measured and/or monitored, such as IL-1, TNF, IFN-gamma, IL-12, IL-18, and GM-CSF. These other cytokines may be used instead of or in addition to IL-6, either in combination or singly.

The methods, devices and systems herein may be applied specifically to treat any disorder for which a reduction of demyelination and/or an increase in remyelination would be beneficial. For example, described herein are electrodes (e.g., cuff electrodes, microstimulators) that may be placed around the vagus nerve and may communicate with one or more stimulators configured to apply appropriate stimulation of the vagus nerve to modulate demyelination and/or remyelination. The stimulator may be implanted. In some variations the stimulator is integral to the electrodes, and may be charged externally. The extremely low duty-cycle of the technique described herein may allow the device to be miniaturized to a greater degree than previously suspected for the treatment of chronic disorders via an implantable device.

In general, a device or system for modulating demyelination and/or remyelination may include a stimulator element (e.g., an electrode, actuator, etc.) and a controller for controlling the application of stimulation by the stimulator element. A stimulator element may be configured for electrical stimulation (e.g., an electrode such as a cuff electrode, needle electrode, paddle electrode, non-contact electrode, array or plurality of electrodes, etc.), mechanical stimulation (e.g., a mechanical actuator, such as a piezoelectric actuator or the like), ultrasonic actuator, thermal actuator, or the like. In some variations the systems and/or devices are implantable. In some variations the systems and/or device are non-invasive. In general, the controller may include control logic (hardware, software, firmware, or the like) to control the activation and/or intensity of the stimulator element. The controller may control the timing (e.g., on-time, off-time, stimulation duration, stimulation frequency, etc.). In variations in which the applied energy is electrical, the controller may control the applied waveform (amplitude, frequency, burst duration/inter-burst duration, etc.). Other components may also be include as part of any of these device or system, such as a power supply (e.g., battery, inductive, capacitor, etc.), transmit/receive elements (e.g., antenna, encoder/decoder, etc.), signal generator (e.g., for conditioning or forming the applied signal waveform), and the like. In some embodiments, a rechargeable battery that may be inductively charged allows the stimulator to deliver numerous electrical stimulations before needing to be recharged. In other embodiments, one or more capacitors that can also be inductively charged can be used to store a limited amount of energy that may be sufficient to deliver a single stimulation or a daily amount of stimulations. This dramatically reduces the size and cost of the stimulator, but requires that the user charge the stimulator daily or before each use.

In one example, an implantable device for modulating demyelination and/or remyelination (and/or reducing or preventing leaking of the blood-brain barrier) includes an electrode for electrically stimulating the vagus nerve. The electrode may be, for example, a cuff electrode. The electrode may be connected (directly or via a connector) to a controller and signal generator. The signal generator may be configured to provide an electrical signal to the electrode(s). For example, the electrical signal may be an electrical waveform having a frequency of between about 0.1 Hz and about 1 KHz (e.g., 10 Hz), where the pulses applied have a pulse width of approximately (50-500 usec, e.g., a 200 usec pulse). The signal generator may be battery (and/or inductively) powered, and the electrical signal may be amplitude and/or voltage controlled. For example in some variations the device or system may be configured to apply a current that is between about 0.05 mA to 25 mA (e.g., approximately 0.5 mA, 1 mA, 2 mA, 3 mA, etc.). The electrical signal may be sinusoidal, square, random, or the like, and may be charge balanced. In general, the controller (which may be embodied in a microcontroller such as a programed ASIC), may regulate turning on and off the stimulation. For example, stimulation may be applied for an on-time of between about 0.1 sec and 10 minutes (e.g., between 1 sec and 5 minutes, between 1 sec and 2 minutes, approximately 1 minute, etc.); the stimulation may be configured to repeat automatically once every x hours or days, e.g., every other day (off time of approximately 48 hours), once a day (e.g., with an off-time of approximately 24 hours), twice a day (off-time of approximately 12 hours), three times a day (off time of approximately 8 hours), four times a day (off time of approximately 6 hours), or the like. In some variations the implant may be configured to receive control information from a communications device. The communications device may allow modification of the stimulation parameters (including off-time, on-time, waveform characteristics, etc.). The communications device may be worn, such as a collar around the neck, or handheld.

In use, an implant may be configured to be implanted so that the electrodes contact or approximate the vagus nerve or a portion of the vagus nerve. In one variation the implant includes a cuff that at least partially surrounds the vagus (e.g., near the carotid region). The controller and/or signal generator (including any power source) may be formed as part of the cuff or may be connected to by a connector (e.g., wire).

In some variations the device may be non-invasive. For example, the device may be worn outside the body and may trigger stimulation of the vagus nerve from a site external to the body (e.g., the ear, neck, torso, etc.). A non-invasive device may include a mechanical device (e.g., configured to apply vibratory energy). In some variations the device is configured to apply ultrasound that may specifically target the vagus nerve and apply energy to activate the vagus nerve. In some variations, transcutaneous magnetic stimulation of the vagus nerve may be used.

In any of the variations described herein, the devices, system and methods may be configured to prevent desensitization of the signal in a way that would reduce or inhibit the modulation of demyelination and/or remyelination. For example in some variations, "over stimulation" of the vagus nerve, e.g., simulation at intensities that are too great or applied for too long, or outside of the frequency ranges described herein, may result in desensitization of the effect, thus further modulation may be limited or inhibited. Therefore, in some embodiments, the amplitude of stimulation may be restricted from exceeding (i.e., be less than) about 3 mA, 4 mA, or 5 mA, and/or the duty cycle may be restricted from exceeding about 1, 2, 3, 4, 5, 6, 7, 8, 9, 10, 15, 20, or 25%. In some embodiments, the amplitude is also at least 0.25 mA, 0.5 mA, 0.75 mA, or 1.0 mA.

The examples illustrated above may provide insight into the devices, systems and methods of use for stimulation of the vagus nerve to modulate demyelination and/or remyelination. These methods and devices may be used to treat any indication for which modulation of demyelination and/or remyelination would be beneficial. Non-limiting examples of indications include neurodegenerative and neuroinflammatory diseases such as multiple sclerosis (MS), Alzheimer's disease, Parkinson's disease, Huntington's disease, Amyotrophic lateral sclerosis (ALS), and Batten disease. Other examples include peripheral neuropathies, cranial neuropathies, and autonomic neuropathies. In general, these devices may offer alternative and in some ways superior treatment as compared to pharmacological interventions aimed at modulating demyelination and/or remyelination, and therefore may be used for any indication for which such pharmacological treatments are suggested or indicated. In some embodiments, the VNS treatments described herein can be used in conjunction with pharmacological treatments, particularly when the pharmacological treatment has a different mechanism of action than the VNS, which may lead to synergistic results.

Thus, the methods of modulating demyelination and/or remyelination as described herein may be used in conjunction with one or more pharmacological interventions, and particularly interventions that treat diseases associated with demyelination, neurodegeneration or neuroinflammation. For example, it may be beneficial to treat a subject receiving stimulation of the vagus nerve to modulate demyelination and/or remyelination by also providing agent such as intravenous corticosteroids (e.g., methylprednisolone), oral corticosteroids, interferons beta-1a and beta-1b, monoclonal antibodies (e.g., natalizumab, alemtuzumab, daclizumab and ocrelizumab), and immunomodulators (e.g., glatiramer acetate, mitoxantrone, fingolimod, teriflunomide, and dimethyl fumarate).

Thus, described herein are devices (VNS devices) for the treatment of neurodegenerative and/or neuroinflammatory disorders. Such devices are generally configured to apply low duty-cycle stimulation to the vagus nerve of a subject, as described in any of the variations (or sub-combinations) of these variations. In some embodiments, the patient is first diagnosed or identified with a neurodegenerative and/or neuroinflammatory disorder, particular a disorder characterized by demyelination or need for remyelination, before being implanted and treated with the VNS device.

In use, any of the methods described herein may include a step of monitoring for demyelination or demyelination-associated disorders, which may be determined through detection of a biomarker from blood and/or cerebrospinal fluid, and/or through medical imaging techniques such as MRI or CT scans. For example, as assay for an inflammatory cytokine (e.g., tumor necrosis factor) may be used to detect acute inflammatory episodes. Monitoring may be continuous or discrete (e.g., at one or more times, or time intervals). In addition or alternatively, biomarkers associated with multiple sclerosis or other neurodegenerative and/or neuroinflammatory diseases or neuropathies can be used for monitoring, depending on the disease being treated. See Housley, W. J., D. Pitt and D. A. Hafler (2015). "Biomarkers in multiple sclerosis." *Clin Immunol* 161(1): 51-58; and Katsavos, S. and M. Anagnostouli (2013). "Biomarkers in Multiple Sclerosis: An Up-to-Date Overview." *Mult Scler Int* 2013: 340508. For example, biomarkers found in MS serum and cerebrospinal fluid include markers of neurodegeneration including neurofilament and GFAP, the monocyte macrophage marker CD163, the glial activation marker YKL-40, the B cell chemoattractant CXCL13, miRNA and mRNA, myelin reactive t cells, Kir4.1 antibodies, osteopontin, and microbiome associated lipopeptides. Any of these biomarkers can be monitored and/or measured alone or in combination, and can be used as feedback to modulate VNS. Other biomarkers for treating MS patients in particular are listed in Table 1.

TABLE 1

Biomarkers in Multiple Sclerosis (A) Diagnostic biomarkers (criteria i, iv, v, and vi)

(1) Genetic-immunogenetic

| | | |
|---|---|---|
| HLA-DRB1*1501 | +++ Risk for MS | See also B, E |
| DR3 and DR4 haplotypes | ++ Risk for MS | |
| HLA-DRB1*04 | ++ Risk for MS | |
| HLA-DRB1*0401 | + Risk for high familial autoimmunity in MS patients | See also F |
| HLA-DQ1*0102 | + Risk for MS, in coexistence with HLA-DRB1*1501 | |
| HLA-DPB1*0501 | + Risk for opticospinal MS | |
| HLA-DPB1*0301 | + Risk for opticospinal MS | |
| IL2RA and IL7RA polymorphisms | + Risk for MS | |
| EVI5, CD58, KIAA0350, and RPL5 polymorphisms | +/− Risk for MS | |

(2) Laboratorial

| | | |
|---|---|---|
| OCB IgG | +++ But with low specificity | See also E |
| KFLC | +++ But with low specificity | See also E |
| MRZ reaction | +++ Higher specificity than OCB IgG | See also E, F |
| Anti BRRF2, anti EBNA-1 | ++ | See also B, C |
| Anti MBP 48-70 and 85-170 | + | See also B, E |
| Anti MBP 43-68 and 146-170 | + Differential diagnosis with OND's | See also B, E |
| MBP/MOG conformational epitopes antibodies | + But low specificity | See also B, E, F |
| VEGF-A | + Lower CSF levels in all disease forms, but low specificity | See also D, E |
| Vitamin D | +++ Lower levels, higher risk for MS | See also C, F |
| TRECs | + Lower serum levels in all disease forms, but low specificity | See also B |
| CSF levels of lipocalin 2 | + Higher CSF levels in MS, but low specificity | See also F |
| AR | +++ Differential diagnosis of MS and NMO | See also C, E |
| NO and NO metabolites | + Higher CSF and serum levels in MS, but low specificity | See also C, E |
| NF-L | ++ Higher CSF levels in MS patients | See also C, F |
| NAA | +++ Differential diagnosis of RRMS and NMO | See also D, E |
| GFAP | +++ Differential diagnosis of MS and NMO | See also C, E |
| | + Differential diagnosis of MS and NMO | See also C, E |
| Nogo-A | ++ For MS forms with prominent neurodegenerative element | See also D |

(3) Imaging

| | | |
|---|---|---|
| Contrast-enhanced T1 lesions | +++ | See also C |
| Hyperintense T2-weighted lesions | +++ | See also C, D, E |
| Corpus callosum DTI abnormalities | ++ Early diagnostic biomarker | See also E |
| MRS findings (glutamate/choline) | +++ | See also C, D, E |
| PET | ++ But still experimental | |
| EPs | +++ | See also |
| Motor EPs | +++ Spinal cord syndrome at presentation | C, D, E |
| VEMPs | +++ Brainstem dysfunction | |
| SSR | ++ Autonomic dysfunction assessment in MS patients | See also E |

(B) Biomarkers of phenotypical expression (criteria ii, iv, v, and vi)

(1) Genetic-immunogenetic

| | | |
|---|---|---|
| HLA-DRB1*1501 | +++ Early disease onset | See also A, E |
| HLA-DRB1*1501 | + Risk for cognitive decline | |
| HLA-DRB1*01 | ++ Protection against malignant disease form | |
| ApoE ε4 | ++ Greater risk for mental disorders | |

(2) Laboratorial

| | | |
|---|---|---|
| OCB IgM against myelin lipids | +/− Aggressive disease course | See also E |
| EBV antibodies | + Early disease onset | See also A, C |
| Anti-MBP | +++ ADEM-like onset in childhood MS | See also A, E |
| Anti-MOG | +++ Childhood MS, ADEM, isolated optic neuritis, anti-AQP4 (−) NMO | See also A, E, F |
| rMOG index | +++ Progressive disease forms | |
| IL-6 serum levels | +++ Age at onset | See also C |
| TRECs | ++ Lower levels PPMS | See also A |
| Amyloid- (1-42) | ++ Lower levels, higher risk for mental disorders | |

(3) Imaging

| | | |
|---|---|---|
| UCCA atrophy | +++ Progressive disease forms | See also E |
| NAGM DTI abnormalities | +++ Progressive disease forms | |

(C) Biomarkers of demyelination-neuroinflammation-relapse (criteria i, ii, iii, iv, v, and vi)

(1) Genetic-immunogenetic

| | | |
|---|---|---|
| TOB1 | +++ Underexpression, higher Th1 and Th17 percentage | See also E |

(2) Laboratorial

| | | |
|---|---|---|
| EBV antibodies | + Higher inflammatory activity | See also A, B |
| CXCL13 | ++ Mobilizes B-cells, T-helper cells | |
| CXCL12 | +/− Neuroprotection against inflammation in EAE/experimental | |
| IFN-/TNF-a | +++ Th1 immune response | |
| IL-1 levels imbalance | + Triggering factor for neuroinflammation | |
| IL-6 | +++ B-cell and T-cell immunity link, Th17 immune response triggering factor | See also B |
| | ++ Correlation with relapse frequency in female MS patients | |
| IL-10-592 position polymorphisms | ++ Regulation of CNS autoimmunity | |
| IL-15 | ++ BBB disruption, enhanced CD8(+) T cytotoxicity | |
| IL-33 | + Increase in IFN-γ and IL-17 in mice EAE | |
| sICAM-1 | ++ Higher levels, higher inflammatory activity | See also F |
| | +++ Higher levels in NMO than MS—marker of BBB disruption | |
| sVCAM-1 | +++ Higher levels in NMO than MS—marker of BBB disruption | See also F |

TABLE 1-continued

Biomarkers in Multiple Sclerosis

| | | |
|---|---|---|
| Laminin 411 | ++ TH-17 enhancement | |
| 4 Integrin | ++ Correlation with gadolinium-enhanced lesions during CIS | See also E, F |
| Osteopontin | ++ Serum and CSF elevation during relapse | |
| Fetuin-A | +++ Overexpression in active demyelinating lesions | See also F |
| Vitamin D | +++ High levels, anti-inflammatory role—lower radiological disease activity | See also A, F |
| CSF mature B-cells/plasma-blasts | ++ Bigger accumulation, higher inflammatory activity | |
| CXCR3 | ++ Helps T-cells to enter the brain | |
| CX(3)CR1 | ++ CD4(+)CD28(−) cytotoxic cells biomarker | |
| CSF CCR2(+)CCR5(+) T cells | +++ Increase during MS relapse—osteopontin enhancement | |
| CD56 Bright NK | ++ Remission phase | |
| AR | +++ Biomarker of BBB disruption | See also A, E |
| MMP-9 | ++ Higher CSF levels during relapse | |
| Ninjurin-1 | ++ Upregulation in active demyelinating lesions | |
| MBP and fragments | +++ Higher CSF levels during relapse | See also F |
| B-Crystalline | +++ Over-expression in active demyelinating lesions | |
| NO and metabolites | ++ | See also A, E |
| 7-Ketocholesterol | ++ | |
| Glutamate | +++ Higher levels in active demyelinating lesions | |
| Cystine/glutamate antiporter | + Over-expression in active demyelinating lesions | |
| NF-L | +++ Higher CSF levels, especially the 3rd week after relapse onset | See also A, F |
| GFAP | ++ Higher levels during relapse | See also A, E |
| S100B | +/− Higher CSF levels during MS/NMO relapse | See also A, E |
| N-CAM | + CSF elevation at remission onset | |
| BDNF | ++ Lower levels inhibit demyelination and axonal loss | See also D, E, F |
| (3) Imaging | | |
| Contrast-enhanced T1 lesions | +++ Active lesions | See also A |
| Hyperintense T2-weighted lesions | ++ Combination of different mechanisms | See also A, D, E |
| MTR decrease | + Demyelination and axonal loss combined | See also D |
| DTI abnormalities | ++ Combination of different mechanisms | See also D, E |
| MRS findings (especially changes in glutamate and choline) | +++ Active lesions | See also A, D, E |
| DTS | ++ Promising but still experimental | See also D |
| EP's delayed conduction | ++ Demyelination biomarker | See also A, D, E |
| (D) Biomarkers of axonal loss-neurodegeneration (criteria i, iv, v, and vi) | | |
| (1) Laboratorial | | |
| VEGF-A | ++ Lower levels, higher risk for neurodegeneration | See also A, E |
| 14-3-3 | +/− Axonal loss | |
| NAA | +++ Axonal loss | See also A, E |
| BDNF | ++ Lower levels inhibit demyelination and axonal loss | See also C, E, F |
| Nogo-A | +++ Higher CSF levels, failure in axonal repair | See also A |
| (2) Imaging | | |
| RNFL thinning | +++ Axonal loss in the optic nerve | See also E, F |
| Hyperintense T2-weighted lesions | ++ Combination of different mechanisms | See also A, C, E |
| Black holes | +++ Axonal loss | See also E |
| MTR decrease | ++ Demyelination and axonal loss combined | See also C |
| DTI abnormalities | ++ Combination of different mechanisms | See also C, E |
| MRS findings (especially NAA) | ++ | See also A, C, E |
| DTS | +++ Promising but still not widely accessible | See also C |
| Visual and motor EPs | ++ | See also A, C, D |
| (E) Prognostic biomarkers—biomarkers of disability progression (criteria ii, iv, v, vi, and viii) | | |
| (1) Genetic-immunogenetic | | |
| HLA-DRB1*1501 | +/− Early progression from RRMS to SPMS | See also A, B |
| HLA-DRB1*1501 | + Worst brain atrophy measures | |
| HLA-DQB1*0301 | + Worst brain atrophy measures | |
| HLA-DQB1*0602 | + Worst whole and gray matter atrophy measures | |
| TOB1 | +++ Early conversion from CIS to CDMS | See also C |
| (2) Laboratorial | | |
| OCB IgG | +++ Conversion from CIS to CDMS | See also A |
| KFLC | +++ Conversion from CIS to CDMS | See also A |
| OCB IgM | +/− Bad prognostic biomarker | See also B |
| MRZ reaction | +++ Conversion from CIS to CDMS | See also A, F |
| Anti-MBP | +/− Conversion from CIS to CDMS | See also A, B |
| Anti-MOG | +/− Conversion from CIS to CDMS | See also A, B, F |
| AR | ++ Marker of clinical severity in NMO | See also A, C |
| VEGF-A | ++ Lower levels, progression from RRMS to SPMS | See also A, D |
| NO and NO metabolites | ++ Higher CSF levels, longer relapses/higher disability progression rates | See also A, C |
| NF-H | +++ Higher CSF levels, progressive forms/bad prognostic biomarker | |
| NF-H and tau | +++ Combined high CSF levels, conversion from CIS to CDMS | |
| Tubulin/actin | ++ Higher CSF levels, progressive forms/worst disability scores | |
| NAA | +++ Lower CSF levels, progressive forms/worst disability scores | See also A, D |
| GFAP | ++ Higher CSF levels, progressive MS forms/worst disability scores | See also A, C |
| | +++ Disability progression in NMO | |
| S100B | + Disability progression in NMO | See also A, C |

TABLE 1-continued

Biomarkers in Multiple Sclerosis

| | | |
|---|---|---|
| BDNF | ++ Lower CSF levels in SPMS patients | See also C, D, F |
| Unblocked α4 integrin | + Prognostic factor of risk for PML | See also C, F |
| (3) Imaging | | |
| RNFL thinning | + Correlation with brain atrophy measures and disease progression | See also D, F |
| Hyperintense T2-weighted lesions | +/− | See also A, C, D |
| Black holes | +/− | See also D |
| Whole brain atrophy measures | ++ Worsening rates at MS onset, prognostic biomarker of disability after 8 years | |
| Gray matter atrophy measures | +++ Higher worsening rates, progressive forms/early CIS conversion to RRMS | |
| UCCA atrophy | ++ Progressive forms, good correlation with EDSS, bad prognostic in RRMS | See also B |
| DTI abnormalities | +++ Early prognostic biomarker of relapse | See also C, D |
| Corpus callosum DTI abnormalities | +++ Bad prognostic biomarker | See also A |
| Spinal cord DTI abnormalities | +++ Good correlation with EDSS scores | |
| Early MRS abnormalities | ++ Bad prognostic biomarker | See also A, C, D |
| Combined EPs | +++ Good prognostic biomarker, especially for benign disease forms | See also A, C, D |
| SSR | ++ Correlation with higher EDSS scores | See also A |
| (F) Biomarkers of therapeutical response (criteria i, iv, v, vi, and vii) | | |
| (1) Genetic-immunogenetic | | |
| HLA-DRB1*0401, 0408, 1601 | +++ Higher risk for developing neutralizing antibodies against IFN-B | See also A |
| (2) Laboratorial | | |
| MRZ reaction | ++ B-cell immunity targeted therapy | See also A, E |
| Anti-MOG | ++ B-cell immunity targeted therapy | See also A, B, E |
| Fetuin-A | +++ Decreased CSF levels in Natalizumab responders | See also C |
| MBP | +++ Decrease in CSF levels in methylprednizolone responders | See also C |
| CSF lipocalin 2 | ++ Decreased CSF levels in Natalizumab responders | See also A |
| Unblocked α4 integrin | +++ Therapeutical response to Natalizumab | See also C, E |
| NF-L | +++ Normalized CSF levels in Natalizumab responders | See also A, C |
| BDNF | +++ CSF elevation in Glatiramer Acetate responders | See also C, D, E |
| TRAIL | ++ Serum levels good predictors of response in IFN-B | |
| MxA | ++ Serum levels good predictors of response in IFN-B | |
| sVCAM | ++ CSF alterations in IFN-B responders | See also C |
| Th17 immune profil | +/− Immune response exacerbation by IFN-B | |
| Vitamin D | +++ Increased levels in IFN-B responders | See also A, C |
| sICAM-1 | + Lower levels in Cladribine responders | See also C |
| sE-Selectin | + Lower levels in Cladribine responders | |
| (3) Imaging | | |
| RNFL | +++ Biomarker of therapeutical efficacy for several agents | See also D, E |

Classification of biomarkers.
+++ very strong correlation,
++ strong correlation,
+ modest correlation, and
+/− controversial correlation.
Criteria used for classification.,
(i) Biological rationale;
(ii) clinical rationale;
(iii) predictability of disease initiation, reactivation or progression, or of disease differentiation;
(iv) sensitivity and specificity;
(v) reproducibility;
(vi) practicality;
(vii) correlation with therapeutical outcome;
(viii) correlation with prognosis and disability.
Biomarkers of more than one category are indicated in the third column.

The information described herein for the first time shows that stimulation of the vagus nerve modulates demyelination and/or remyelination and/or leaking through the blood-brain barrier. The examples provided herein are not intended to be comprehensive, but merely illustrate and embody certain variations of the invention. It is within the abilities of one of ordinary skill in the art to understand and apply, without undue experimentation, the invention as described herein.

Example 1

To study the effect of VNS on neurodegeneration and neuroinflammation, a lysolecithin (LPC)—induced MS model can be used. Lysolecithin is a bioactive pro-inflammatory lipid that is a detergent-like membrane solubilizing agent. A 1% solution of LPC can induce local demyelinating lesions when injected into the white matter of the spinal cord. Four distinct epochs occur over 14 days post-injection: (1) demyelination; (2) oligodendrocyte progenitor cell (OPC) recruitment; (3) differentiation; and (4) remyelination. FIG. 1 illustrates a typical example of the 4 epochs, where demyelination occurs from about days 0-3, OPC recruitment occurs from about days 3-7, OPC differentiation occurs from about days 7-10, and remyelination occurs from about days 10-14.

To induce a self-limited demyelinating lesion, spinal cords of female BALB/c mice were injected between T3-T5 with 1% LPC (0.5 µL at 0.25 µL/min). The procedure to inject the mice with LPC was as follows. The mouse was anesthetized and stabilized into a stereotaxic frame. A midline incision was made between the scapulae. The underlying fat pads were bluntly separated and the spinous process of the T2 vertebra was identified and a laminectomy was performed. A syringe was advanced to 0.3 mm into the spinal cord and 0.5 µL of LPC was injected at a rate of 0.250 µL/min for 2 min. The muscle and adipose tissue were sutured and the skin was closed with surgical staples VNS was performed as previously described (Olofsson, Levine, et al. 2015. Bioelectronic Medicine: 37-42) on Day 0 or Day 4 post-induction with LPC. More specifically, to study the effect of VNS on demyelination, VNS (0.75-1 mA, 250 µS pulse, 10 Hz) or sham VNS (0 mA) was performed immediately following LPC administration, and the mice were euthanized on the day of expected peak lesion volume (day 4 post-induction; *J Neurocytol* 24(10): 775-81). The demyelination experimental protocol is summarized in FIG. 2A.

Spinal cord lesion volumes/areas were quantified by myelin loss as assessed from luxol blue-stained, 15 μm serial sections. FIG. 3A shows an illustration of a typical cross-section of the spinal cord, and FIG. 3B shows a luxol blue stained cross-section of the spinal cord with a LPC induced lesion in the anterior *funiculus* of the white matter 5 days post-LPC injection. To study the effect of VNS on remyelination, VNS or sham VNS treatments was performed 4 days post-induction, mice were euthanized on days 8, 14, or 21 post-induction, and nerves were processed as above. The remyelination experimental protocol is summarized in FIG. 2B. Mean lesion volumes between groups were compared by t-test.

Results: The demyelination protocol illustrated in FIG. 2A showed that VNS inhibited demyelinated lesion progression compared to sham. On day 4 post-induction, the mice were euthanized and the spinal cord around the LPC injection site was sectioned and stained with luxol blue. As shown in FIGS. 4A-4D, the mean lesion volume in the VNS group (0.75 mA) was significantly lower than in the sham group (p=0.0023 by t-test). VNS at 0.25 mA resulted in a mean lesion volume similar to sham VNS.

Figure 3B:
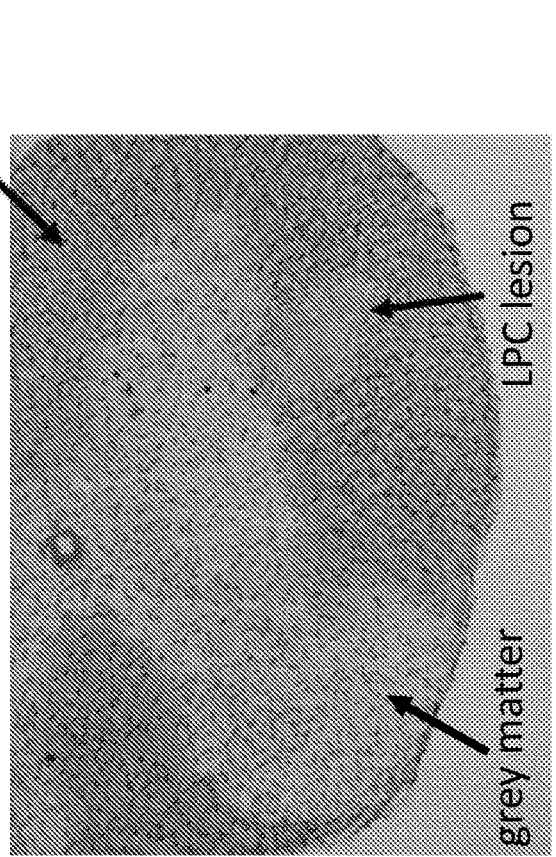
FIG. 3B illustrates a stained cross-section of a spinal cord with a lesion (which may be considered a demyelination) induced by lysolecithin injection.
Figure 3A:
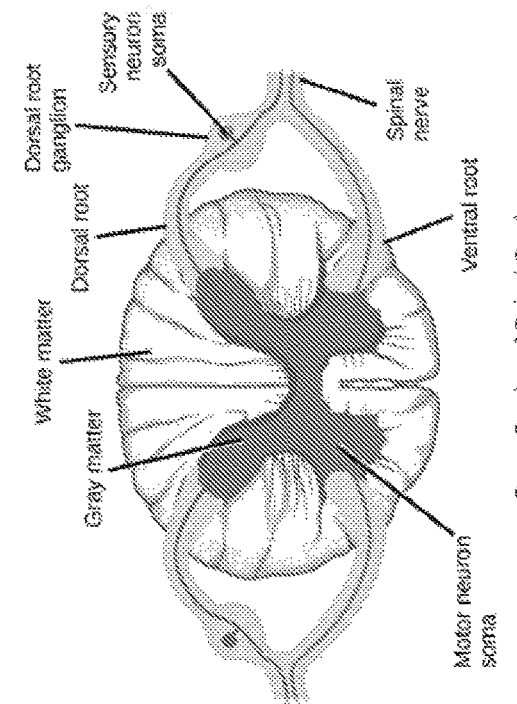
FIG. 3A illustrates a cross-section of a healthy spinal cord.
Figure 4A:
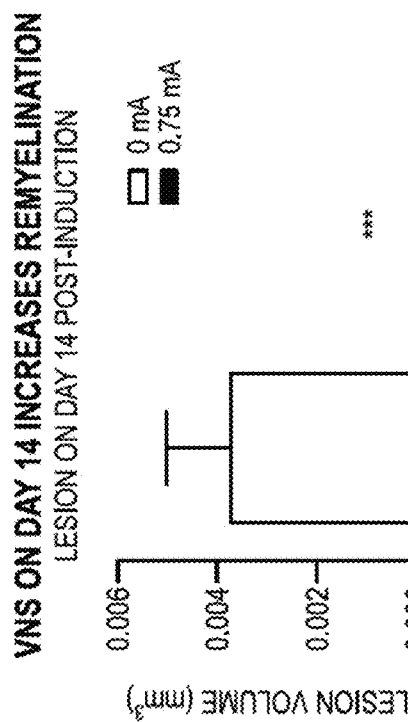
FIGS. 4A-4D are graphs that show that vagus nerve stimulation reduced the amount of demyelination that resulted from lysolecithin injection.
Figure 4B:
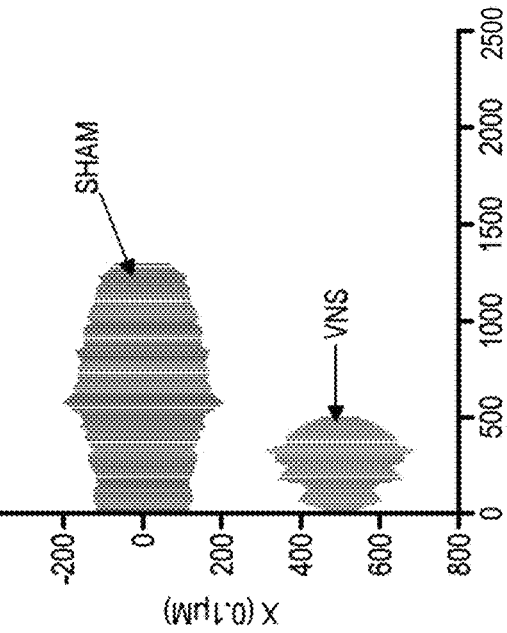
Figure 4C:
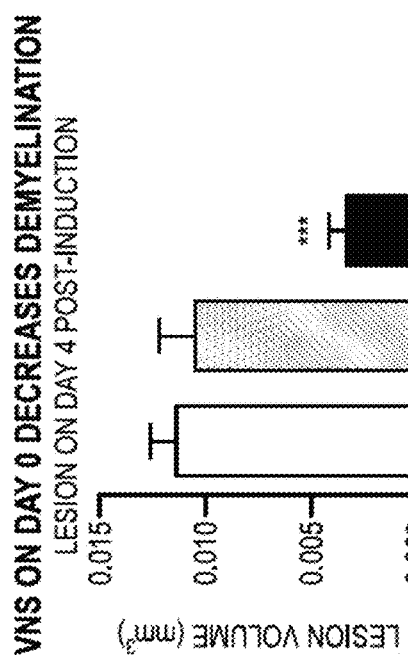
Figure 4D:
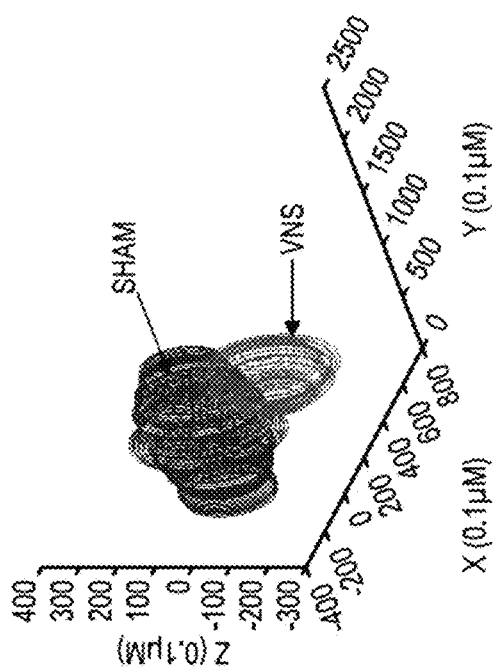
Figure 5A:
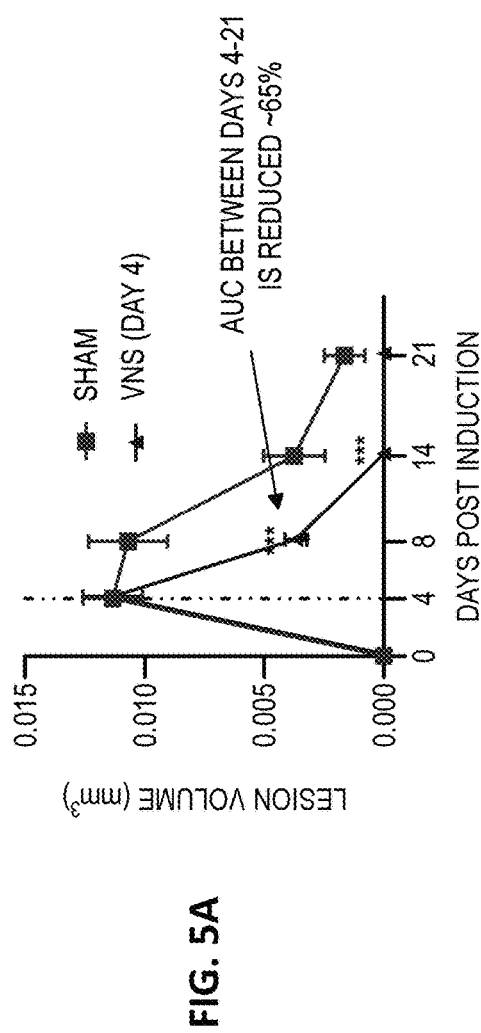
FIGS. 5A-5G are graphs that show that vagus nerve stimulation increased the rate and/or amount of remyelination.
Figure 5C:
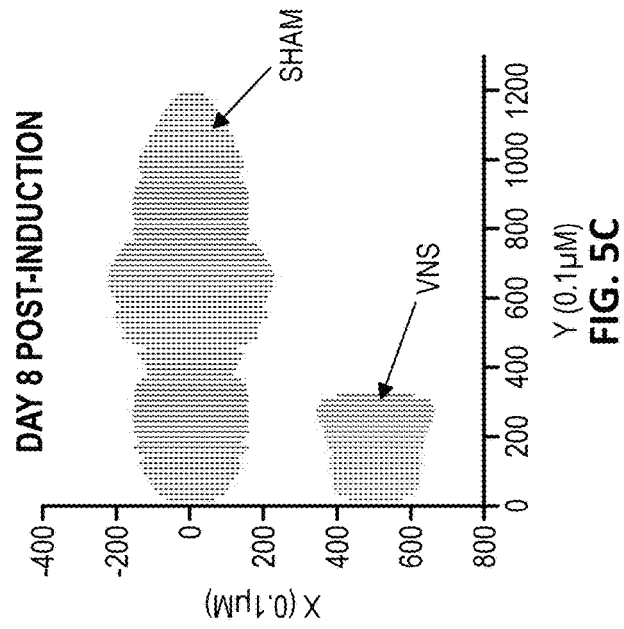
Figure 5B:
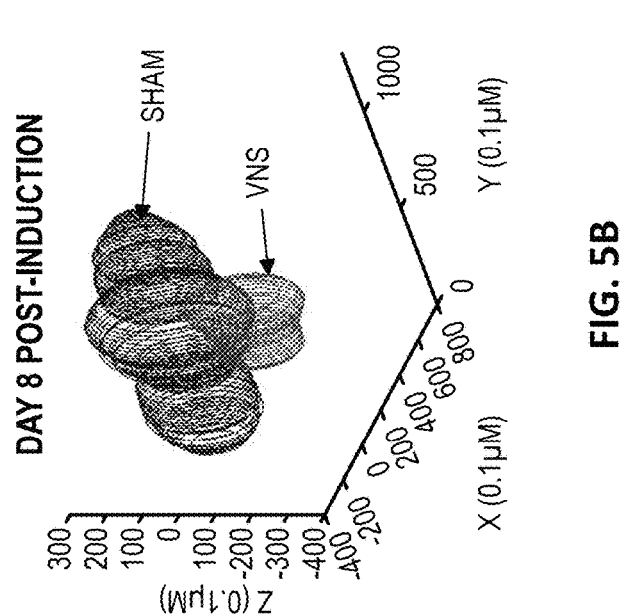
Figure 5E:
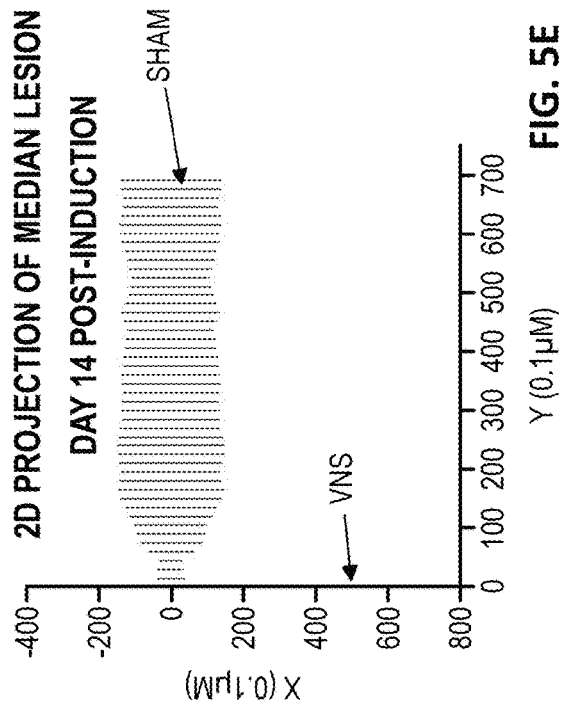
Figure 5G:
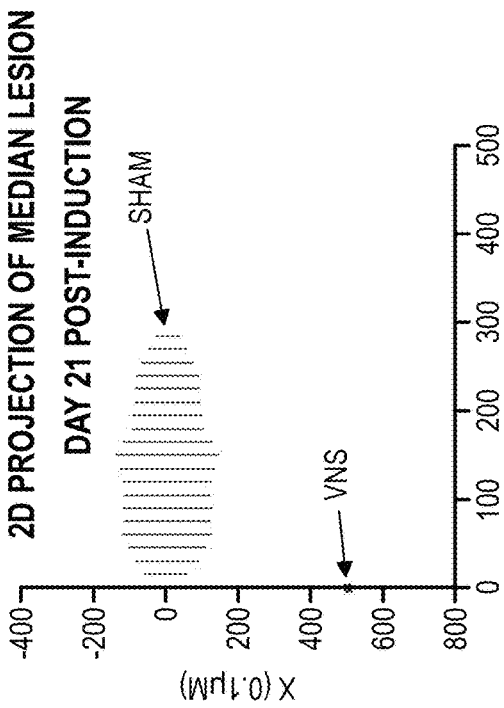
Figure 5D:
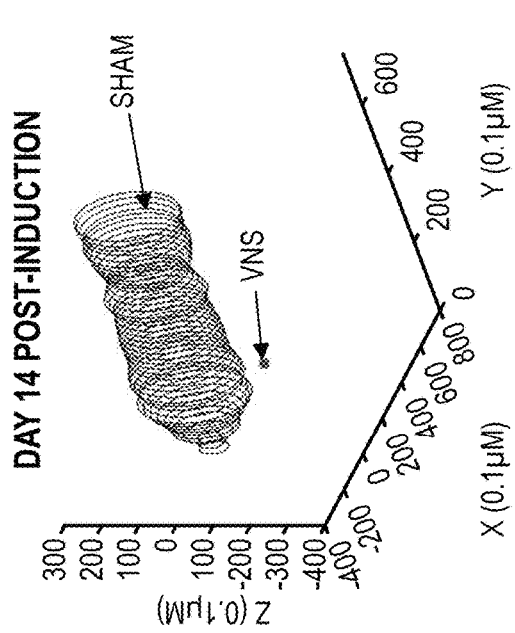
Figure 5F:
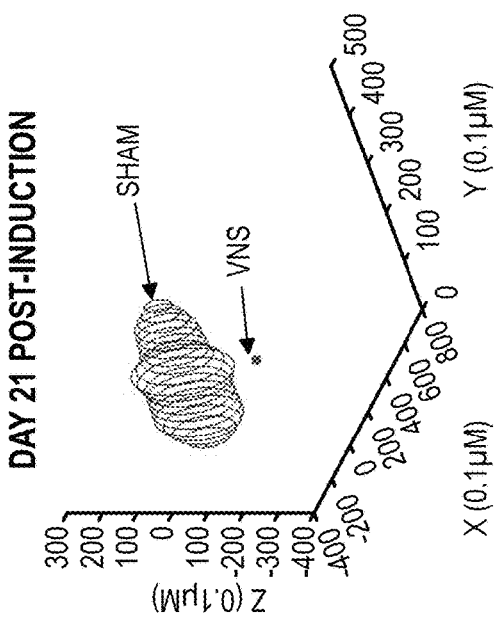

The remyelination protocol illustrated in FIG. 2B showed that remyelination occurred at a significantly accelerated rate in the VNS group. As shown in FIGS. 5A-5G, on day 8 post-induction, mean lesion volume in the VNS group was reduced. On day 14 post-induction, mean lesion volume in the VNS group was significantly lower than in the sham group. On day 14, 11 out of 12 VNS animals had no detectable lesion. By Day 21, the mean lesion volume in the sham group was almost back to baseline. FIG. 5A shows that the area under the curve (AUC) between days 4 and 21 is reduced by about 65 percent with vagus nerve stimulation.

Conclusions: VNS reduced demyelination and accelerated remyelination, demonstrating a robust effect after a single dose in this model. Repeated stimulation of the vagus nerve with an implanted nerve stimulator may further reduce the rate of demyelination and/or further accelerate remyelination. This will be tested in an experimental autoimmune encephalomyelitis model to further assess the potential of VNS to treat MS.

Example 2

Figure 6B:
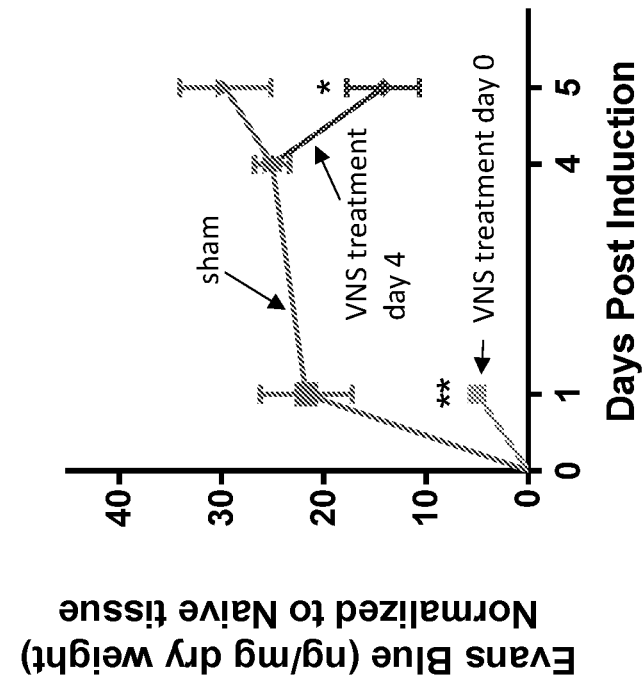
FIG. 6B illustrates the use of VNS treatment as described herein to reduce the leakiness of the blood-brain barrier following induced demyelination. VNS treatment before induced demyelination prevented the passage of dye (Evans blue) through the rat model of the blood brain barrier. VNS treatment after induced demyelination reduced and reversed the leakiness. VNS treatment on Day 0 (following LPC induction) significantly decreased leukocyte infiltration 24 hours post-stimulation, while VNS treatment on Day 4 post-LPC induction significantly decreases leukocyte infiltration 24 hours post-stimulation.
Figure 6A:
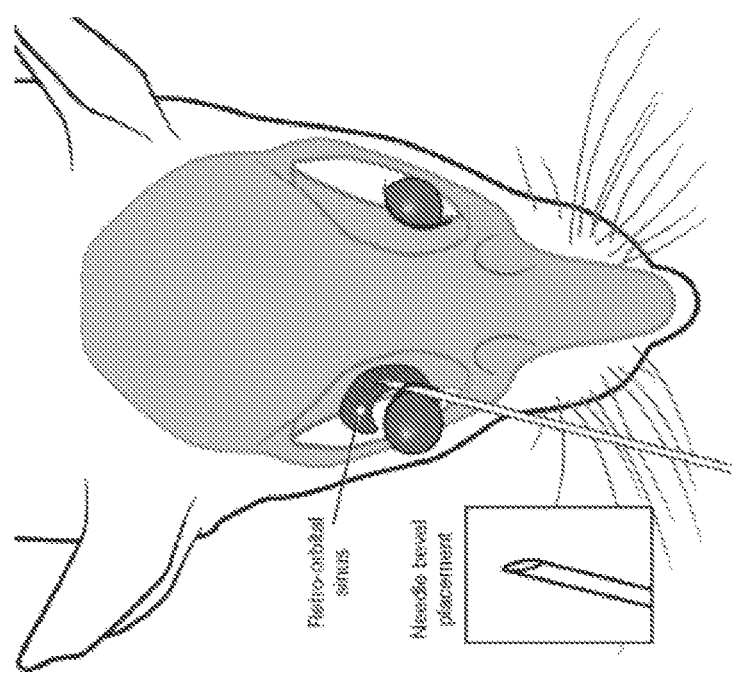
FIG. 6A shows the experimental protocol used to show the effect of VNS treatment as described herein on vessel leakiness following post-induction of demyelination.

Another study was performed to determine the effect of VNS on vessel leakiness 24 hours post-induction and stimulation. A lesion was induced as described above using LPC injection and VNS was performed immediately following induction. At 24 h, 0.15 mL of 1% Evans blue dye was injected intravenously through retro-orbital injection under anesthesia for 1 hr., as shown in FIG. 6A. One hour later, the animals were euthanized via cervical dislocation. Measurement of extravasation in the spinal cord (SC) was determined by extracting the SC and weighing the SC wet. The SC was then dried for 24 h at 56° C. and weighed dry. The Evans blue dye was extracted with a formamide solvent for 48 h at 56° C. incubation. The supernatant was measured spectroscopically at 620 nm and the quantity of Evans blue dye was determined by interpolation from a reference curve. The quantity of Evans blue dye was normalized to the dry weight of the SC. As shown in FIG. 6B, less Evans blue dye was extracted from the spinal cord from the mice that received VNS, which provides evidence that VNS reduces vessel leakiness 24 hours post-induction and stimulation. In addition, the amount of Evans blue dye extracted from the mice that received VNS was similar to the amount of Evans blue dye extracted from naïve mice (no LPC induced lesion).

Leakiness in the blood brain barrier may allow immune cells and inflammatory cytokines and chemokines to pass through and contribute to continued inflammation in the brain and/or spinal cord. Therefore, VNS may reduce vessel leakiness around the central nervous system (CNS), thereby reducing the recruitment of proinflammatory cells such as lymphocytes (e.g., T-cells) and macrophages to the brain and spinal cord, thereby reducing the inflammation in the CNS and reducing the amount demyelination that results from an inflammatory attack by the immune system.

Example 3

In general, the apparatuses and methods described for VNS therapy may also be used to prevent or treat increased leakiness of the blood-brain barrier, as illustrate in FIG. 6B.

Methods: 1% LPC was injected into the spinal cord white matter of BALB/c mice. For the first intervention time point, VNS therapy or sham VNS was performed immediately after injection. 24 hours later, mice (VNS, sham VNS, and naïve (no-LPC)) are injected with 1% Evans blue dye which binds to the albumin in blood and is left to circulate for 1 hour. Spinal cords are then harvested, dried for 24 hours in pre-weighed tubes at 60° C. Dried tissues are then incubated in formamide for 48 hours. Supernatant is then extracted from the tubes and read spectroscopically at 620 nm. For the second intervention time point, VNS therapy or sham VNS therapy occurs on day 4 post-LPC induction. On day 5 post-LPC induction, Evans blue extravasation is performed the same way as described for demyelination experiment. Evans blue concentration is compared (ng/mg of tissue) and normalized to naïve animals.

Results: LPC increased blood-spinal cord leakiness. VNS therapy significantly reduced Evans blue extravasation into the spinal cord compared to sham (81% decrease) 24 hours post-LPC induction (FIG. 6B). In addition, VNS therapy on day 4 post-LPC significantly reduced Evans blue extravasation on day 5 compared to sham (52% decrease).

Conclusion: VNS therapy increases the integrity of the blood-spinal cord barrier and subsequently reduces the extravasation of protein/Evans blue and other circulating species, including antibodies, DAMPS/PAMPS, and immunocytes into the central nervous system.

Example 4

Another experiment was performed to determine whether the effect of VNS on demyelination was α7 nicotinic acetylcholine receptor (nAChR) dependent. Two mice strains were used in the study. One mice strain is the C57 Black subtype 6 (C57BL/6), which is a common wild type strain that expresses α7 receptors and are denoted as α7+/+. The second mice strain is an α7 knockout strain of the C57BL/6 strain, which lacks the α7 receptor and are denoted as α7−/−. Each of the mice strains were given LPC injections in sham (no VNS) and VNS groups. Tissue extraction was performed 4 days post-injection. The procedure was essentially identical to the Balb/c mice demyelination experiments described above in Example 1.

Figure 7A:
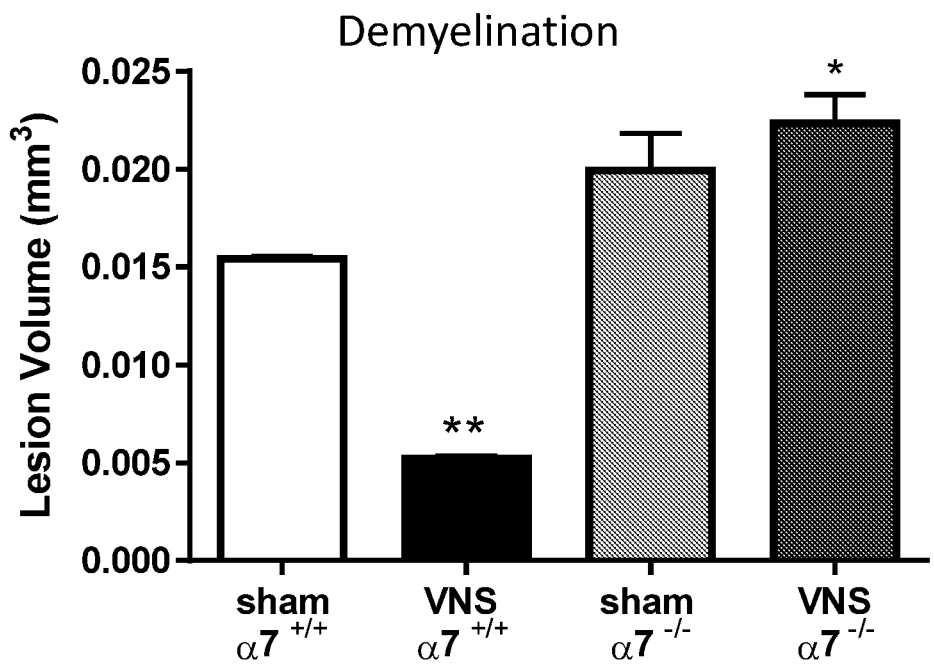
FIG. 7A illustrates the effect of the alpha-7 nicotinic acetylcholine receptors ($\alpha7$ nAChR) in preventing demyelination remyelination from VNS treatment (compared to sham without VNS treatment).
Figure 7B:
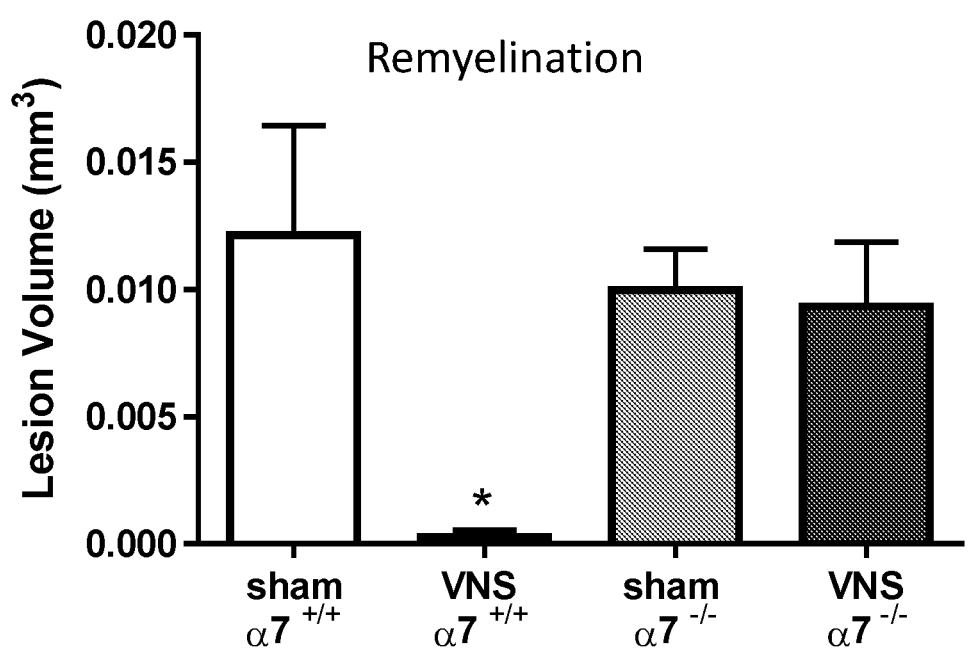
FIG. 7B illustrates the effect of the alpha-7 nicotinic acetylcholine receptors in increasing remyelination from VNS treatment (compared to sham without VNS treatment).

As shown in FIG. 7A, the protective effects of VNS on demyelination is α7 nAChR-dependent. VNS treatment on mice with the α7 nAChR showed a reduced lesion volume when compared with sham, while VNS treatment on mice without the α7 nAChR showed no reduction in lesion volume when compared with sham. Similarly, the remyelination effect of VNS treatment may be α7 nAChR dependent, as shown in FIG. 7B. In this example, the effect of VNS treatment on remyelination in the presence (+/+) and absence (-/-) of the α7 nAChR due to either sham (no VNS treatment) or VNS treatment were examined, showing a substantial decrease in lesion volume, the maker for remyelination following induction of a demyelination event (e.g., application of LPC.

In FIGS. 7A-7B, 1% LPC was injected into the spinal cord white matter of α7 nAChR knockout mice and C57BL/6 (wildtype) mice. For demyelination experiment, VNS treatment or sham VNS treatment, tissue collection, processing, and analysis are all the same as mentioned above for FIG. 1A. For remyelination, VNS and sham VNS intervention occurs the same as experiment described for FIG. 4B. Spinal cords are harvested only on day 8 post-LPC induction. Processing and analysis performed are the same as described for FIGS. 4A-4B.

Result: VNS therapy decreased demyelination in wildtype C57BL/6 mice. VNS therapy did not decrease demyelination in α7 KO animals (FIG. 7A). VNS therapy increased remyelination in wildtype animals, but did not increase remyelination in the knockouts (FIG. 7B). Thus, the effects of VNS on demyelination and remyelination are α7-dependent.

Example 5

Figure 8:
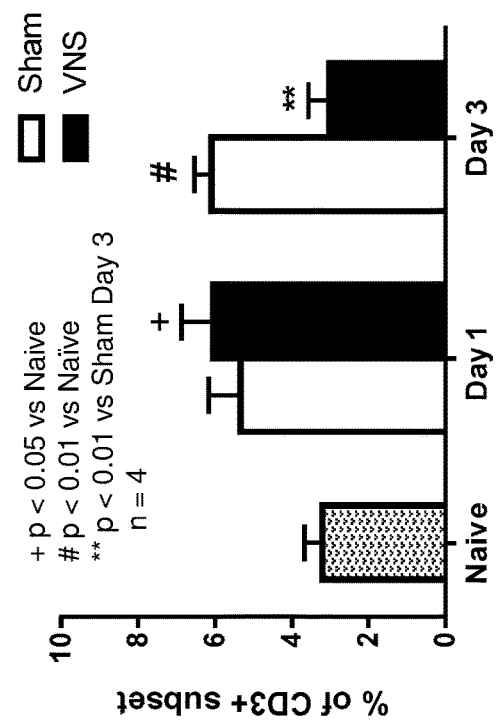
FIG. 8 shows the effect of VNS treatment as described herein to prevent or reverse leakiness of the blood-brain barrier compared to sham (no VNS treatment).
Figure 9:
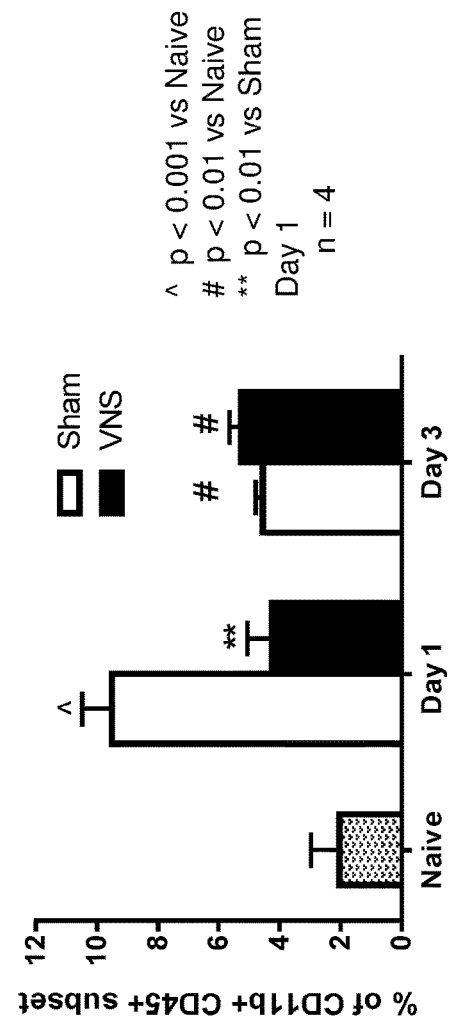
In FIG. 9, CD3+ T cell infiltration was significantly decreased in the VNS group on Day 3 post-LPC induction compared to Sham group by 50%.

In general, the apparatuses and methods described for VNS therapy may also be used to prevent or treat increased immunocyte homing to the central nervous system, as illustrate in FIGS. 8 and 9.

In FIGS. 8 and 9, CD3+ T cell infiltration through a model for the blood-brain barrier is significantly decreased in the VNS treatment group. As shown in FIG. 8, the CD3+ T cell infiltration through the model of the blood-brain barrier on Day 3 post-LPC induction compared to Sham group is reduced by 50%. In. FIG. 9, the macrophage infiltration is significantly decreased 24 hours post-LPC induction in the VNS treatment group compared to the Sham (no VNS treatment) group by 55%.

Methods: Surgical procedures and VNS/sham VNS treatments remain the same from FIG. 4A. Spinal cords from VNS therapy, sham, and naïve mice are harvested on days 1 or 3 post-LPC induction. Tissue is then digested in enzymatic cocktail for 20 minutes at 37° C. followed by trituration and filtering through a 100 μM mesh screen. Single cell suspension is then put through a density gradient to remove myelin debris from glia cells and immune cells. Once isolated, cells are blocked in FACS buffer and CD32/CD19 for a half hour to prevent unspecific antibody staining. Cells are counted and checked for viability via hemocytometer. Cells are then placed in tubes, stained for either T cells (CD3+) or macrophages (CD11b+, CD45hi) and then analyzed via flow cytometer. Populations of cells are quantified using FlowJo program.

Result: LPC increased CD3+ T cell and macrophage infiltration in the spinal cord compared to naïve tissue (FIGS. 8 and 9). There was a significant reduction in CD3+ T cell infiltration on day 3 post-LPC induction in VNS therapy treated animals compared to sham (50% reduction) (FIG. 9). In addition, VNS therapy resulted in a significant decrease in macrophage infiltration compared to sham 1 day post-LPC induction (55% reduction) (FIG. 9). Thus VNS significantly reduces the infiltration of peripheral immunocytes into the CNS in this lysolecithin-induced MS model.

As shown in FIGS. 10A-10B, VNS therapy also increased remyelination following a decrease in myelination. During spinal cord extractions for all prior experiments performed (see examples 1-4, above), blood was collected via cardiac puncture as well. Blood was centrifuged at 8,000×g for 5 minutes, the serum was collected and stored at -80° C. Using a Resolvin D1 ELISA kit, levels of RvD1 were measured spectroscopically from the serum of VNS and sham VNS mice for the demyelination (D4 harvest) and remyelination (D8, D14, and D21 harvests) experiments. Levels of RvD1 are analyzed (pg/mL) and represented as a percent of sham by day.

Result: as showing FIG. 10A, VNS therapy on day 0 (LPC-induction) increased serum levels of RvD1 on day 4. As shown in FIG. 10B, VNS on day 4 post-LPC induction also increased RvD1 in the serum levels of RvD1 with the highest concentration occurring on day 14 post-LPC induction. RvD1 levels in VNS serum were decreased as compared to sham at 21 days post-LPC induction, likely due to earlier resolution in the VNS group.

Thus, VNS therapy increases the pro-resolving lipid mediator RvD1 in serum which may contribute to the increased speed in resolution time of LPC-induced lesions compared to sham.

Example: System

Figure 11:
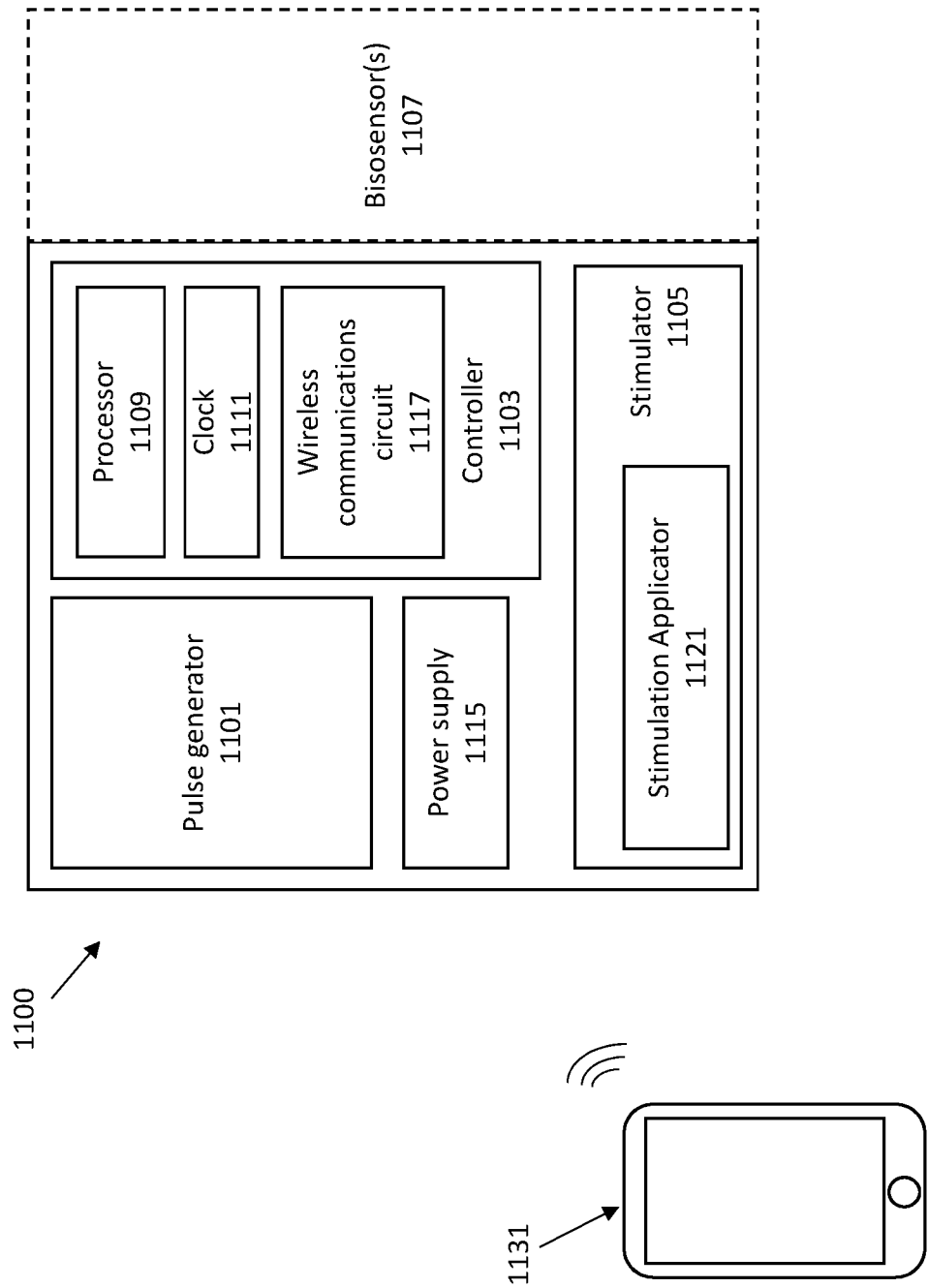
FIG. 11 schematically illustrates one example of an apparatus for reducing demyelination (e.g., increasing remyelination and/or reducing leakage through the blood-brain barrier), as described herein.

FIG. 11 schematically illustrates one example of a system 1100 for treating demyelination (e.g., for treating MS, or any other demyelinating disorders). In some variations the system for reducing demyelination and/or increase remyelination by stimulation of a vagus nerve includes a controller 1103, a stimulator 1105, and a pulse generator 1101. The pulse generator and stimulator may be connected to and controlled by the controller. In some variations all or some of the system may be implanted into the patient's body. All or some of the components of the apparatus may be enclosed by a housing (e.g., an implant housing). In general, the systems may also include one or more biosensor 1107 configured to detect one or more biomarkers. The biosensor may be coupled with the rest of the system (e.g., implant) or it may be separate and may communicate via a wired or wireless connection. For example the biosensor may be implanted into the body so as to sample blood, spinal fluid, or the like; in some variations the biosensor is external to the body and may be single use or configured for limited-reuse. In some variations the biosensor may include a sensor for determining a patient's physical condition (e.g., temperature, nerve conduction, etc.). In some variations the biosensor may be an immunochemical sensor configured to detect binding of one or more analytes and/or to provide a concentration.

The stimulator may be configured to apply stimulation to the vagus nerve. A stimulator may be configured for electrical stimulation, mechanical stimulation, or both. For example, the stimulator may include or be coupled with the pulse generator 1101 (e.g., waveform and/or pulse generator, oscillator, etc.). The stimulator may include one or more stimulation applicators 1121 (e.g., one or more electrodes, mechanical transducers, etc.) for contact with the tissue, including the vagus nerve.

Any of the apparatuses may also include one or more power supplies 1115, and/or power regulation circuit, etc.

The controller is typically functionally coupled to the one or more biosensor (e.g., receiving data from the biosensor(s)) and controls the stimulator and may be configured to apply stimulation to the vagus nerve from the stimulator sufficient to reduce demyelination and/or increase remyelination of nerves within the patient when the biosensor detects a biomarker indicative of demyelination (including detecting active demyelination or a marker that is indicative of imminent active demyelination).

For example, a system may include an implant comprising a stimulator (e.g., a waveform and/or pulse generator, an oscillator, a power supply and/or power regulation circuit, etc.), a stimulation applicator (e.g., one or more electrodes, mechanical transducers, etc.), and a controller. The controller may be configured as a microcontroller and may be in electrical communication with the stimulator so as to control operation of the stimulator. The controller may include one or more processors, a memory and/or a timer. The stimulator and/or controller may be in electrical communication, one or more stimulation applicators. In some variations the controller may include or be in communication with wireless communications circuitry 1117 for wirelessly communicating with one or more remote processors 1131. The remote processor may be a hand-held device (e.g., smartphone, wearable electronics, etc.). The controller may optionally be in communication with one or more biosensors that may be included with the implant or may be remote from the implant (e.g., may be wearable, single-use, etc.). In some variations the biosensors are wirelessly connected to the apparatus.

The electronic device (e.g., smartphone, wearable electronics, etc.), which is in communication with controller, can be configured to accept input from the user and/or to sense one or more biomarkers for triggering a change in the electrical stimulation parameters. For instance, the user may experience a flare-up or relapse, where the user experiences the onset or worsening of symptoms (e.g., pain, muscular cramping or stiffness and/or fatigue). The electronic device can be configured accept input from the user to indicate that they are experience a flare-up, which can cause the controller to adjust the stimulation parameters accordingly (e.g., increase or decrease frequency and/or current) Likewise, the electronic device may be configured to accept input from the user indicating recovery from a flare-up in which the user experiences reduction or extinction of symptoms, which can cause the controller to adjust stimulations accordingly (e.g., increase or decrease frequency and/or current). In some cases, the electronic device is configured to accept a score or rating indicating the severity of a flare-up, and the controller can adjust the stimulation parameters based on the score or rating. Alternatively or additionally, the electronic device can be configured to sense one or more biomarkers that indicate the onset of a flare-up. In some embodiments, the electronic device is configured to non-invasively detect the biomarker(s), for example, using renal biomarker(s) and/or optic nerve biomarker(s). In some embodiments, the electronic device is additionally or alternatively configured to detect the biomarker(s) from a fluid sample. The electronic device may be configured to detect a severity of the flare-up based on, for example, a measurement of the sensed biomarker(s). The controller can be configure to adjust the stimulation parameters (e.g., automatically) based on the detected biomarker(s) indicating the onset and/or diminishment of a flare-up and/or based on the severity of the flare-up.

Increased Clearance

The methods and apparatuses described above describe the treatment of multiple sclerosis (MS). More specifically, the methods and apparatuses described herein may be refined to increase the clearance of cellular debris that may be associated with MS and other neurodegenerative and/or neuroinflammatory disorders as well as acute neuronal injury. Thus, in some variations the methods and apparatuses described herein may increase clearance of neuronal cellular debris by the targeted application of charge to the vagus nerve. The targeted application of charge to the vagus nerve may enhance clearance of cellular debris, particularly in multiple sclerosis patients by modulating the activity of one or more of microglia and/or other macrophages.

Endothelial cells lining the inside of small blood vessels may promote clearance of myelin debris, a common detrimental outcome of demyelinating diseases such as multiple sclerosis (MS). Activity may also decrease due to age or other disease states. In healthy subjects, macrophages/microglia may engulf myelin debris and may otherwise perform homoeostatic activity in the normal CNS, a function associated with high motility of their ramified processes and their constant phagocytic clearance of cell debris. In some conditions, including MS, there may be a reduction of recruitment or activation of microglia to clear myelin debris. Insufficient clearance by microglia, prevalent in several neurodegenerative and/or neuroinflammatory diseases and declining with ageing, is associated with an inadequate regenerative response. The methods and apparatuses described herein may enhance the activity microvascular endothelial cells, and/or macrophages and/or microglia. Specifically, the application of vagus nerve stimulation (VNS) within a defined range of values may result in increased endothelial-mediated clearance of tissue debris and/or macrophage/microglial-mediated clearance of tissue debris.

For example, described herein are methods of treating a patient for a neurodegenerative and/or neuroinflammatory disorder and/or acute CNS injury by increasing the activity of microglia and/or other macrophages for repeating period of time and/or for a sustained period. This may be achieved by the application of vagus nerve stimulation within a range of charge (e.g., in nanocolumb to microcolumb range) of between about 2.5 nC/day (e.g., about 0.1 mA and 0.1 msec pulse-with VNS) to about 7.5 mC/day. Pulses may be applied between 0.1 and 50 Hz (e.g., between 1 and 20 Hz, etc.). The charge may be delivered either directly, e.g., by an implantable device, or indirectly, as by a transcutaneous delivery device. Outside of these ranges (e.g., the application of less than 2.5 nC/day) typically has little or no effect on the majority of patients. Similarly, the application of greater than about 7.5 mC/day may have no additional effect and in some cases may result in an inhibition of the effect. Thus it may be beneficial to limit the daily application of charge to be between about 2.5 nC and 7.5 mC per day (e.g., between about 5 nC and 7 mC, between about 10 nC and about 6.5 mC, between about 50 nC and about 6 mC, between about 100 nC and about 6 mC, etc.).

Applicants have found that the application of VNS within the recited charge range increases the clearance of debris. For example, images of neuronal tissue from animals treated within the effective range of applied charge (e.g., adjusted for animal size and stimulation location) stained for myelin debris shows an increase in intracellular breakdown products, suggested that myelin debris uptake is increased after stimulation. This increase may be sustained for a period following stimulation (e.g., over hours and days). Surprisingly, this effect was seen even with older animals (e.g., otherwise normal mice) showing an enhancement compared to controls otherwise showing normal aging effect of decrease myelin clearance.

Any of the methods described herein may target endothelial cell and/or microglia and/or macrophage activity. For example, in some variations the method and/or apparatus may include examining one or more markers for endothelial cell and/or macrophage and/or microglial activity. These markers may be particularly useful in more precisely targeting the treatment, either with just the VNS treatment alone or in combination with one or more compositions for treating a disorder involving demyelinated neurons such as (but not limited to) MS.

Figures 14, 15:
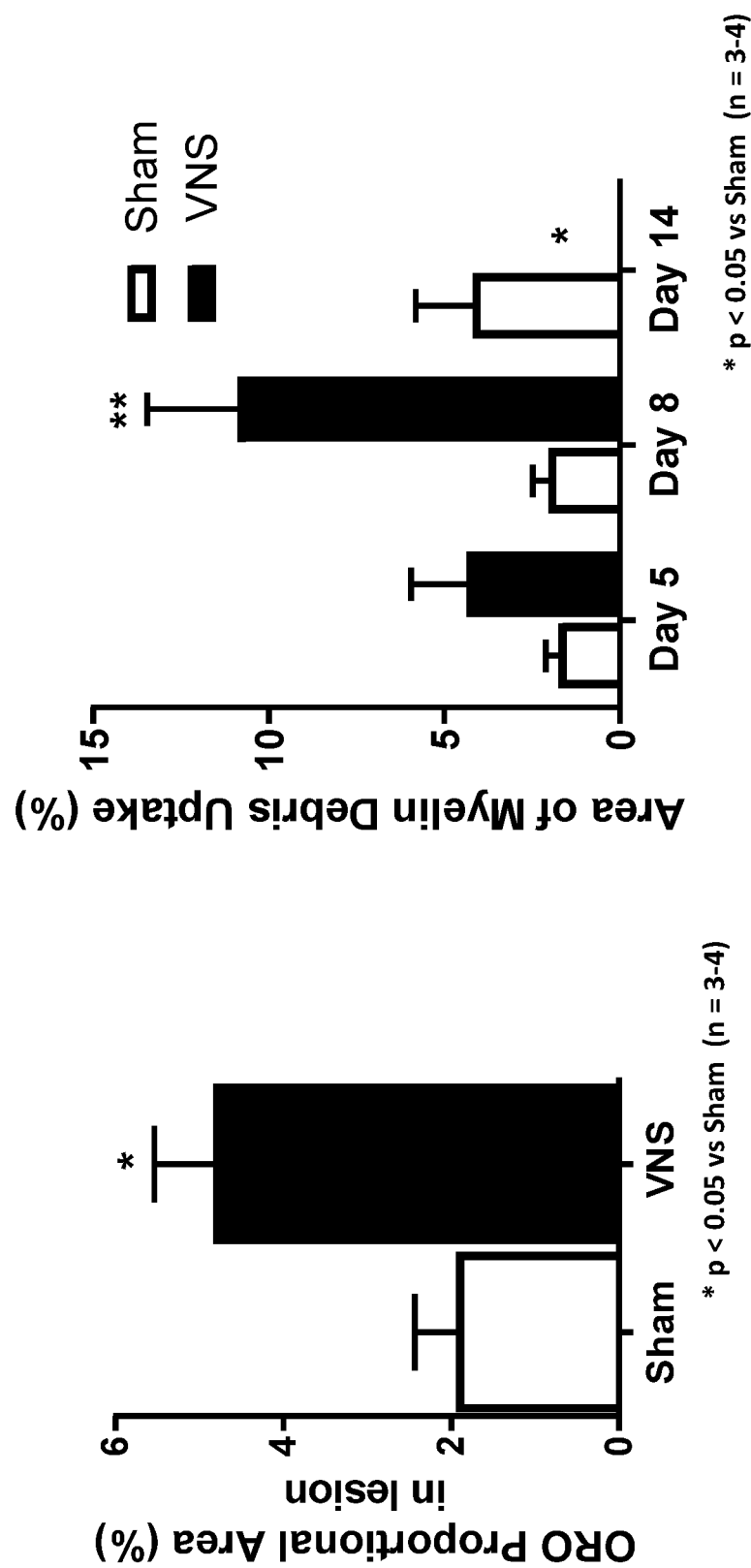
FIGS. 14 and 15 illustrate vagus nerve stimulation (VNS) significantly increased myelin debris uptake when the stimulation was within the prescribed treatment ranges.

FIGS. 14 and 15 illustrate the increase in myelin debris update following VNS within the effective dosing range described herein. In general, tissue resolution of damage may require clearance of damaged cells and debris. In particular, in MS, the process of remyelination may be heavily dependent on endothelial, microglial and macrophage clearance of damaged cells and myelin debris (e.g., efferocytosis and phagocytosis) before oligodendrocytes can lay down new myelin on damaged axons. In MS, the cells responsible for clearing cellular and extracellular debris may have become senescent and inefficient at general endocytosis; a similar effect may be seen in older people and in older animals, causing delayed healing and rapid progression of diseases, including, but not limited to, MS.

Stimulating the vagus nerve electrically (e.g., VNS) can increase the rate of phagocytosis and efferocytosis to increase the rate of disease resolution, demonstrated with remyelination in a rodent model of MS, as discussed above and down in FIGS. 14 and 15. Similar processes enable repair in many other disease contexts. For example, stimulating the vagus nerve electrically can induce more efficient general endocytosis in aged rodents. This finding may be extended to humans, where VNS can reverse senescence in cells, including the cells of older individuals, to increase the rate of repair and the resolution of disease and damage, and to potentially extend life.

In FIG. 14, the data was generated from an animal model (BALB/c mice), in which 1% lysolecithin was injected into the spinal cord white matter (e.g., 0.5 uL at 0.25 uL/min), and VNS (in this example, 0.75 mA, at 10 Hz) or sham VNS was performed immediately after injection ("paradigm A"). Animals were euthanized on day 4 post-induction and intact spinal cords were harvested. In a second treatment paradigm ("paradigm B"), similar mice were treated with VNS (0.75 mA, 10 Hz) or sham VNS was performed on day 4 post-induction. Animals were euthanized on days 5, 8, 10, or 14 post-induction and intact spinal cords were harvested.

Spinal cords were cut into 20 μM sections, and stained with oil red O, which shows the presence of fat or lipids in fresh, frozen tissue sections and is used mainly to measure lipid accumulation. Oil red O is a fat-soluble diazo dye that functions as an oil-soluble colorant (at droplets stain an intense red-orange color). Oil red O stains myelin degradation products and is used as a marker of phagocytosis. Stained area within the lesion was quantified as a percentage of the lesion.

As shown in FIGS. 14 and 15, vagus nerve stimulation (VNS) significantly increased myelin debris uptake when the stimulation was within the prescribed treatment ranges described herein. In FIG. 14, there was an increase in positive staining area compared to sham control, indicating a more than double increase in phagocytosis in this region of the neural tissue. Specifically, when looking at animals treated as per treatment paradigm A, there was an approximately 2.5× fold increase in oil red O staining as a % of lesion for the VNS group compared to the sham group ($p<0.05$) on day 4. FIG. 15 shows a time course for treatment when using treatment paradigm B. in this example, there was an approximately 2.5× and 5.5× fold increase in oil red O staining as a percent of lesion for the VNS group compared to the sham group ($p<0.05$) on day 5 and day 8 respectively. On day 14 there was an increase in oil red o staining in the sham group as compared to sham day 4 and 8. There was no detectable myelin uptake in the VNS group as there were no longer any detectable lesions.

Figure 17:
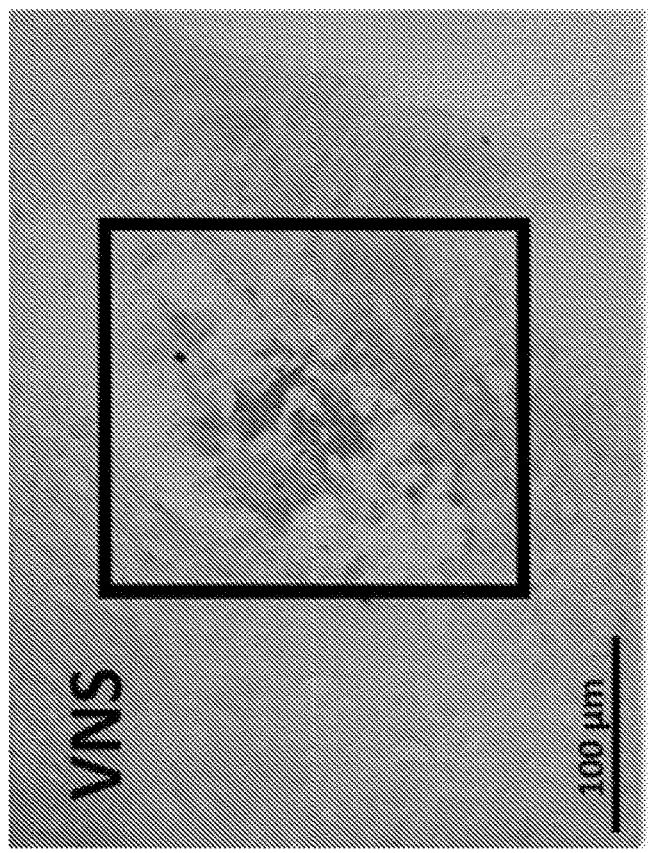
FIG. 17 shows an image from animals treated with VNS on day 4 of treatment paradigm A, post-VNS.
Figure 16:
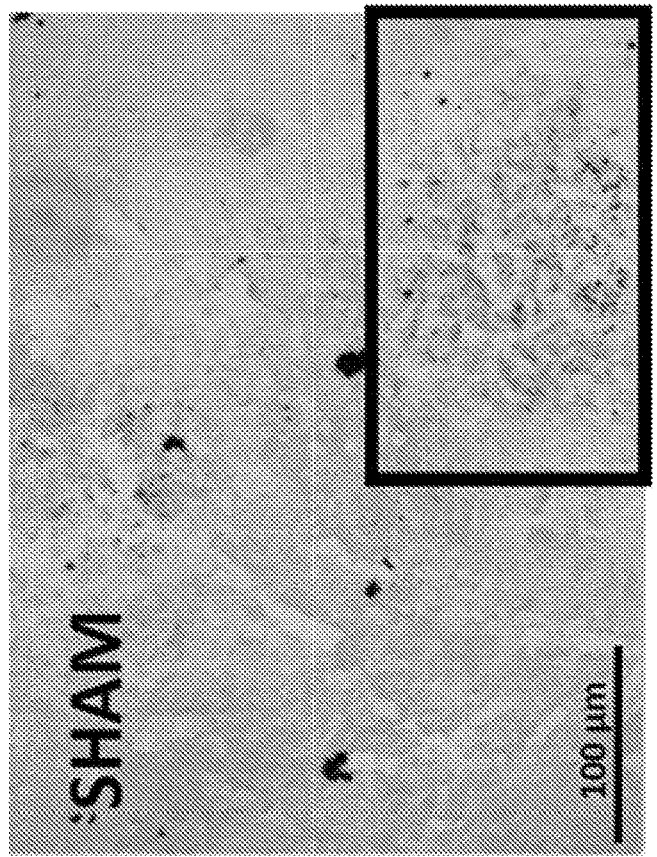
FIG. 16 shows stained sections through tissue from sham animals.
Figures 18, 19:
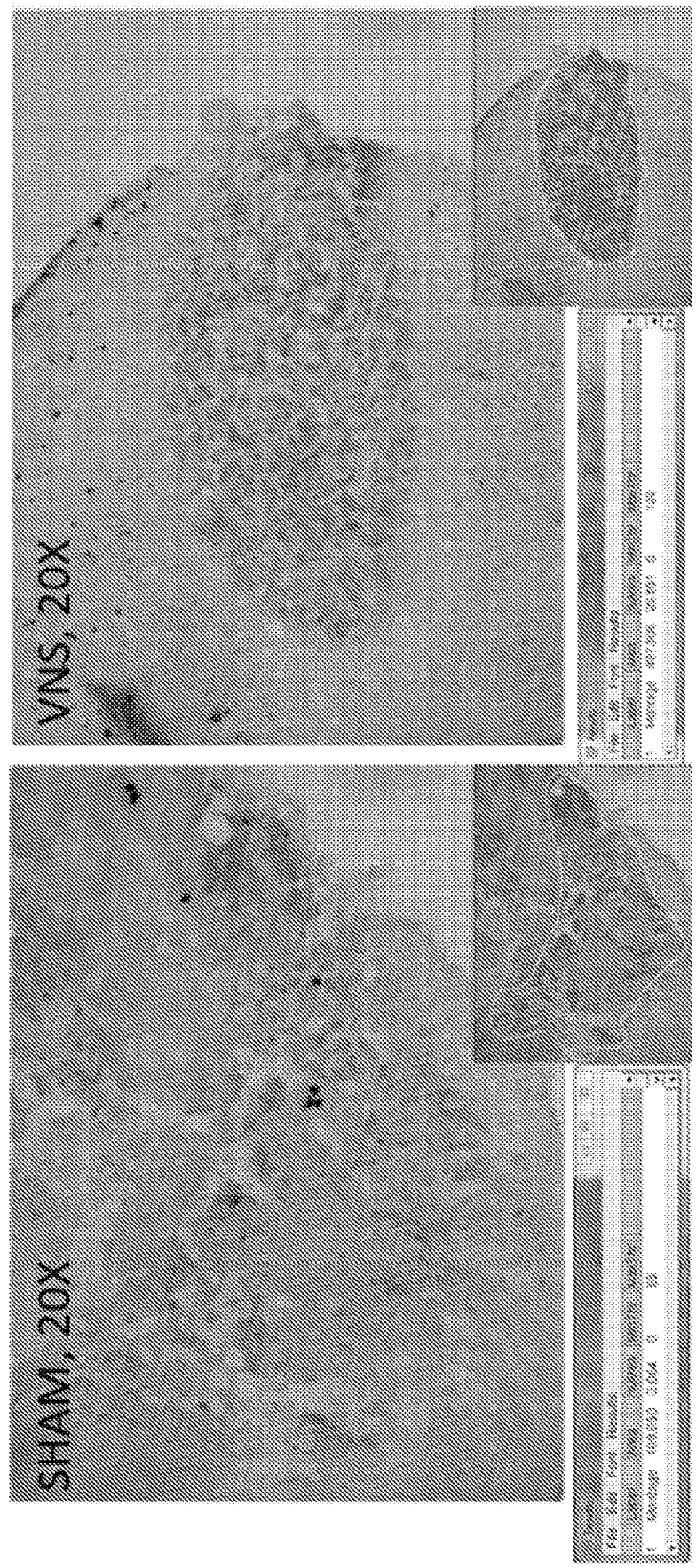
FIGS. 18 and 19 show analysis of the staining to quantify the intensity and extent.

Thus, as evidenced by FIGS. 14 and 15, VNS greatly increases myelin debris uptake by macrophages and microglia in this model as assessed by oil red O staining. An acceleration in myelin debris uptake vs sham was evident. This may also be seen from the raw data shown in FIGS. 16-19, showing representative O Red O staining patterns from the tissue. FIGS. 16 and 18 show stained sections through tissue from sham animals. FIGS. 17 and 19 show images from animals treated with VNS on day 4 of treatment paradigm A, post-VNS (FIG. 17) or day 8 post-induction for paradigm B (FIG. 19). The boxed regions in FIGS. 16 and 17 show lesions. There was significantly more staining in VNS treated regions. The inset regions in the bottoms of FIGS. 18 and 19 show analysis of the staining to quantify the intensity and extent.

Similar results were seen in older mice, in which remyelination normally declines. For example, 1% lysolecithin was injected into the spinal cord white matter of in aged (19 months old) C57Black6 mice and treatment paradigm B was utilized. For example, VNS (0.75 mA, 10 Hz) or sham VNS was performed on day 4 post-induction, and animals were euthanized on day 10 post-induction, and intact spinal cords were harvested. Spinal cords were cut into 20 μM sections and stained with Luxol-fast blue or oil red O, and stained area within the lesion was quantified. As seen in FIGS. 20 and 21, VNS both accelerated remyelination (FIG. 20) and enhanced myelin debris clearance (FIG. 21). As shown in FIG. 20, there was a 34% reduction in lesion volume in the VNS group relative to the sham group on day 10 post-induction. As shown in FIG. 21, there was a 2.4× fold increase in oil red O staining as a % of lesion for the VNS group compared to the sham group ($p<0.05$) on day 10. Thus, in aged mice, VNS increases myelin debris uptake by macrophages and microglia as assessed by oil red O staining, and an acceleration in remyelination of the induced lesion was evident in the VNS group.

Example 6: Evidence of Enhanced Phagocytosis

As described herein, tissue resolution of damage due to an inflammatory event generally requires clearance of damaged cells and debris. In multiple sclerosis (MS), the process of remyelination is believed to be heavily dependent on endothelial, microglial and macrophage clearance of damaged cells and myelin debris (efferocytosis and phagocytosis) before oligodendrocytes can lay down new myelin on damaged axons. The cells responsible for clearing cellular and extracellular debris become senescent and inefficient at general endocytosis in older people and in older animals, causing delayed healing and rapid progression of diseases, including, but not limited to, MS.

Figure 22:
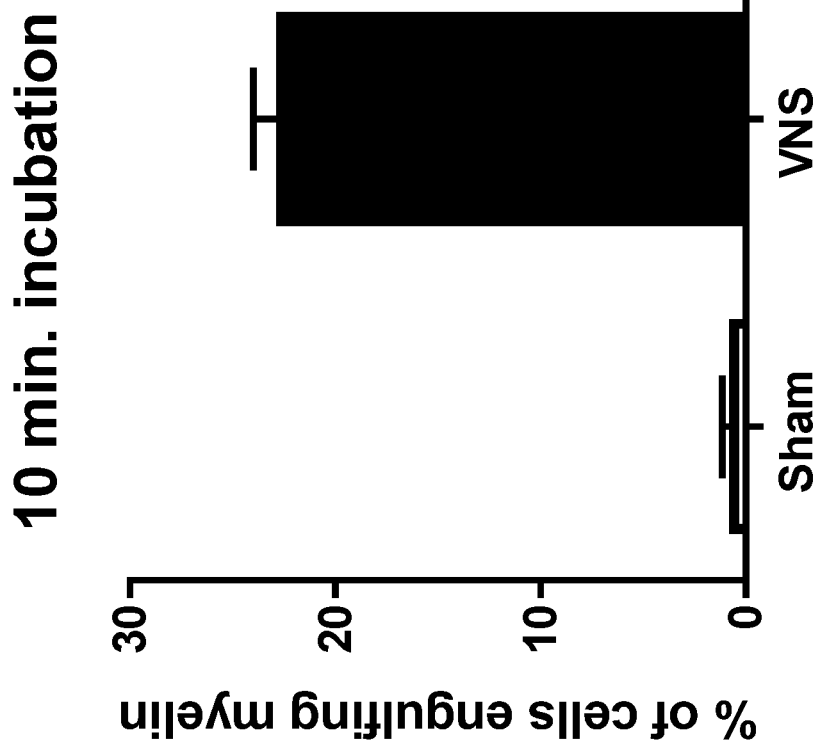
FIG. 22 is a graph showing that VNS enhances myelin clearance, as evidenced by the increase in myelin uptake by macrophages following VNS (e.g., showing an increase in the percentage of cells engulfing myelin following VNS).

Surprisingly, as shown herein, stimulating the vagus nerve electrically can increase the rate of phagocytosis, which in turn increases the rate of disease resolution. FIG. 22 illustrates results of an ex-vivo uptake study demonstrating evidence of enhanced myelin-uptake by macrophages following VNS in mice. The mice were treated with either a VNS dosage or a sham VNS. The macrophages were harvested from the treated mice, and the myelin uptake was quantified. Primary macrophages isolated from the mice that had VNS applied were shown to be more efficient at taking up myelin compared to the sham VNS. As shown in FIG. 22, macrophages from the mice treated with VNS dosage mice had accelerated myelin debris uptake compared to macrophages from the sham stimulated mice. These results indicate that stimulating the vagus nerve electrically can induce more efficient general endocytosis in rodents. These result suggest VNS intervention in humans may reverse senescence in cells, to increase the rate of repair and the resolution of disease and damage, and to extend life. Similar processes may be vital to enable repair in many other disease contexts.

The results of FIG. 22 were obtained based on an ex-vivo uptake study using the following methods: BALB/c mice (from Charles River laboratories) were acclimated for 7 days, anesthetized, and treated with either a VNS dosage (60 second pulse train, 10 Hz frequency, 250 uS pulse width, 0.75 mA) or a sham VNS. After 4 hours, the mice were euthanized by $CO_2$ asphyxiation and peritoneal macrophages extracted. The cell suspension of peritoneal macrophages was cultured on 24 well plates containing glass cover slips and incubated over night at 37° C. with 5% $CO_2$. The cells were washed with phosphate-buffered saline (PBS) and incubated with CFSE-labeled myelin (100 m) in complete RPMI medium for 10 minutes at 37° C. Cells were washed with PBS and fixed with 4% PFA for 10 minutes. Fixed cells were washed with PBS and stained with DAPI for 30 minutes. The stained cells were washed with PBS and the coverslips were mounted with ProLong anti-fade mounting medium and imaged using Zeiss ApoTome fluorescent microscope. Total macrophage numbers in the field of view were counted via DAPI staining. Myelin uptake was also quantified via CFSE-positive cells. The percentage of phagocytosing cells in the overall population was then calculated.

Example 7: EAE Model

Figure 23:
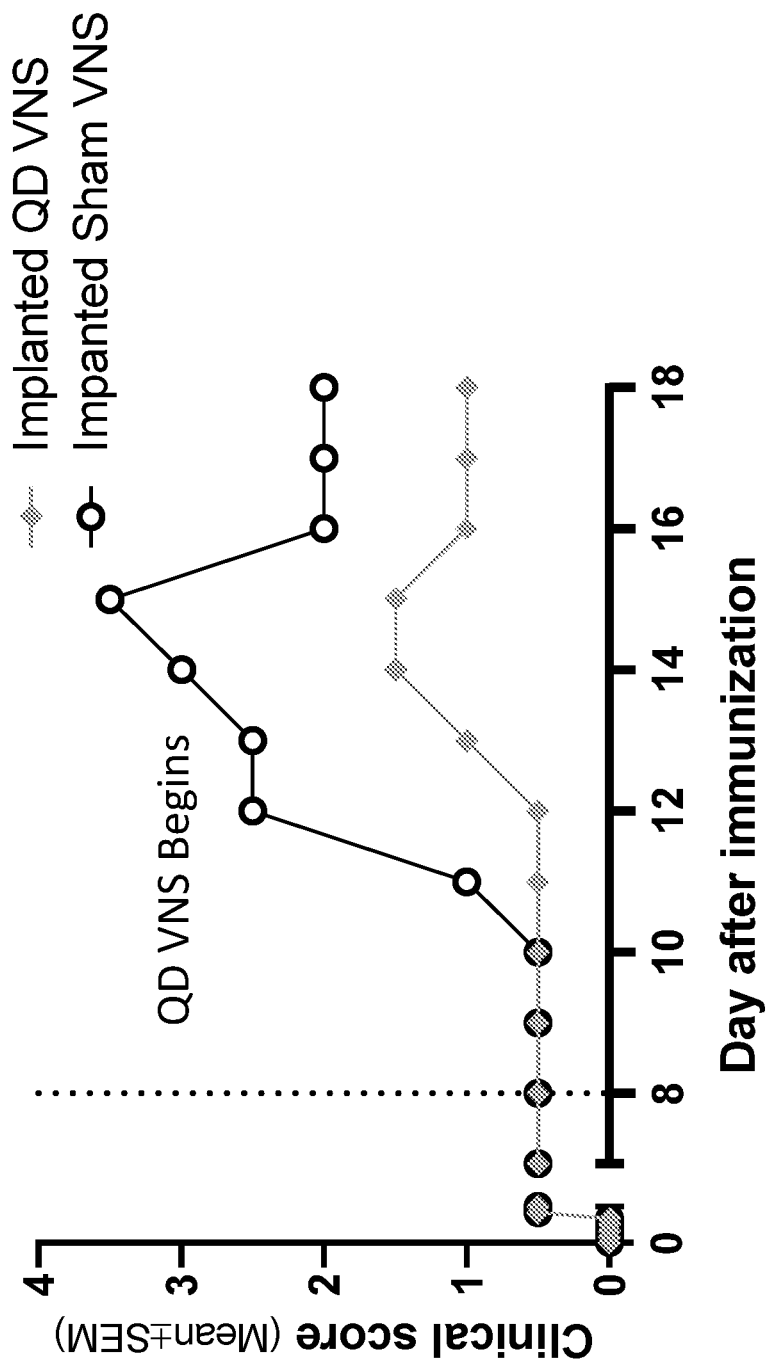
FIG. 23 is a graph comparing clinical scores of rats treated chronic low duty cycle VNS versus sham VNS, showing a reduction in clinical scores from implanted VNS vs. implanted sham treatment in an MS model.
Figures 24, 25:
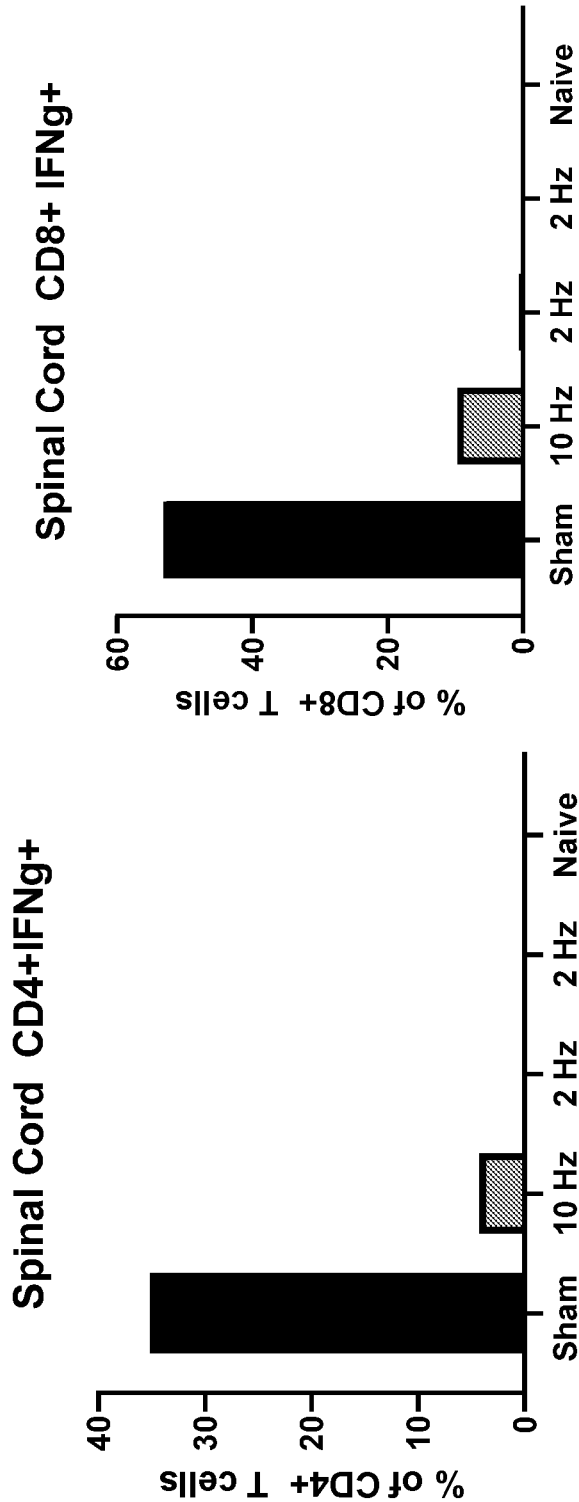
FIG. 24 shows the percent of CD4+ T cells in samples from rat spinal cord treated with VNS as compared to sham, showing the VNS reduces the pathogenic CD3+/CD4+/IFNg+TH1 cells in the spinal cord one to two days following VNS.
FIG. 25 shows the percent of CD8+ T cells in samples from rat spinal cord treated with VNS as compared to sham, showing the VNS reduces the pathogenic CD3+/CD8+/IFNg+TH1 cells in the spinal cord one to two days following VNS.

FIGS. 23-25 show results from experimental autoimmune encephalomyelitis (EAE) model studies comparing low duty cycle VNS treatment versus sham VNS. FIG. 23 compares clinical symptom scores of rats treated chronic low duty cycle VNS versus sham VNS. These results show that low duty cycle VNS can delay onset of significant disease symptoms and abrogate disease severity. FIGS. 24 and 25 compare % of CD4+ T cells or CD8+ T cells in samples from rats treated with acute VNS. The results show that a single dose of VNS at 2 Hz or at 10 Hz prevents the ingress of pathogenic CD4+ and CD8+ IFNg+ Th1 cells. In MS, the progression of disease is causally linked to infiltration of immunocytes, including T helper type 1 (Th1) cells. Therapies targeting infiltration of these cells have been found to be effective and clinically approved to treat MS (e.g. natalizumab). As demonstrated within this data, low duty cycle stimulation of the vagus nerve substantially blocks the infiltration of Th1 cells, both CD4+ and CD8+ IFNg-producing cells.

The results of FIG. 23 were obtained using the following methods: female Lewis rats (from Charles River laboratories) were acclimated for 7 days. Pulse generators (Rodent-MR, SetPoint Medical) were implanted into rats, with the cuff electrode positioned around the left cervical vagus nerve. EAE was induced by injecting 0.1 mL of gpMBP (69-88) antigen with CFA emulsion mix (Cat #EK-3110, Hook Laboratories, MA) subcutaneously on both sides of lower back. The rats were weighed and monitored for clinical score as per the Hooke laboratories EAE scoring guide. Daily 60 second VNS (0.3 mA, 10 Hz QD) or sham VNS began on Day 8 day post induction.

Figure 13:
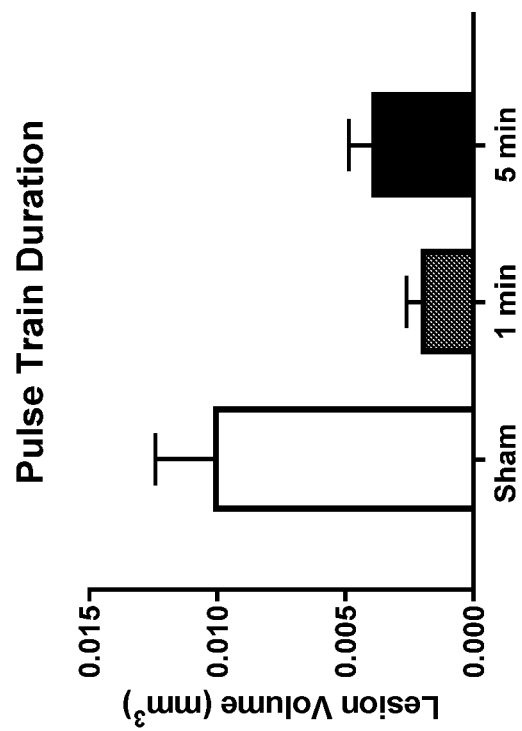
FIG. 13 illustrates significantly more lesion area remyelinated after stimulation at 1 or 5 minutes at 10 Hz, while in general, stimulation for less than 20 minutes (e.g., less than 15 minutes, less than 10 minutes, less than 9 minutes, less than 8 minutes, less than 7 minutes, less than 6 minutes, less than 5 minutes, etc.) was more effective than longer times.
Figure 12:
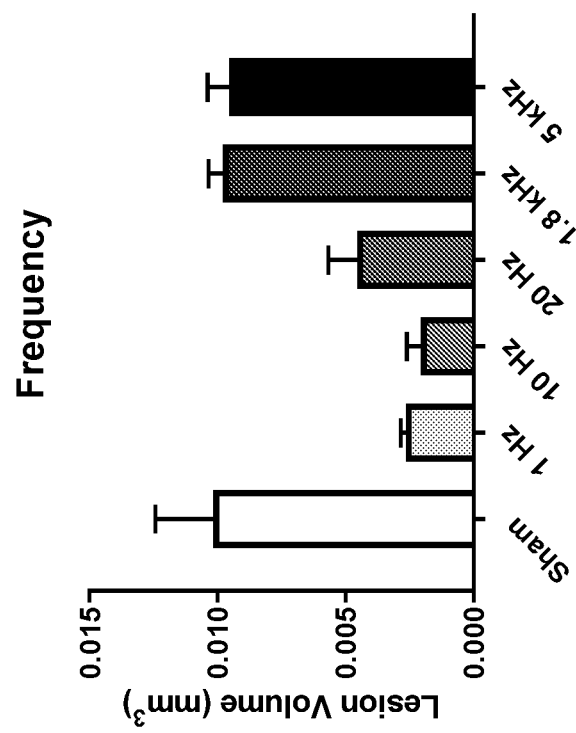
FIG. 12 illustrates VNS at a frequency of less than about 100 Hz (e.g., 75 Hz or less, 50 Hz or less, 40 Hz or less, 30 Hz or less, 25 Hz or less, etc.) more effective than higher frequencies, e.g., 1.8 kHz and above.

The results of FIGS. 24 and 25 were obtained using the following methods: Female Lewis rats (from Charles River laboratories) were acclimated for 7 days and EAE was induced by injecting 0.1 mL of gpMBP (69-88) antigen with CFA emulsion mix (Cat #EK-3110, Hook Laboratories, MA) subcutaneously on both sides of lower back. One rat was maintained naïve to induction and treatment. The rats were weighed and monitored daily for clinical score as per the Hooke laboratories EAE scoring guide. On day 9 post-induction, VNS (30 seconds, 0.3 mA, 2 Hz or 10 Hz) or Sham VNS was performed under anesthesia. After 24-48 hours, the rats were euthanized by $CO_2$ asphyxiation and the blood was collected directly by cardiac puncture. Spinal cord tissues were collected in ice cold hibernate medium. The tissues were rinsed with PBS (1×) and then digested with 1 μg/ml collagenase/dispase (Roche Life Science, Germany) in neurobasal medium (Gibco, Thermo Fisher Scientific, Waltham, MA, USA) for 1 hour at 37° C. on a rotator-shaker. Following digestion, spinal cord tissues were washed with HBSS (Gibco™ HBSS), triturated using fire-polished glass Pasteur pipettes (Fisher Scientific, Waltham, MA), and filtered through a 70-μm strainer. The cell suspension was layered onto 15% BSA in HBSS and centrifuged at ×129 g for 20 min without brake. The cell pellet containing the infiltrated cells were suspended in FACS buffer (1×PBS, 1% FBS in 0.5 mM EDTA) with CD32 Mouse anti-Rat (Fc block, 1:100) blocking antibody for 30 minutes on ice. The cells were stained for external surface staining with eFluor 455UV Fix viability dye; eBioscience (1:2000), CD45-PB; Biolegend (1:100), CD11b PE-Cy7 (1:100), CD3 APC-Cy7; Novus Biologicals (1:100), CD4 Alexa Fluor 488; Bio-Rad (1:100), CD8 BUV805; BD Biosciences (1:100), in FACS blocking buffer for 30 minutes on ice. The cells were washed with PBS and fixed using CYTO-PERM fixation buffer for 10 minutes on ice for intra cellular staining with IFN-gamma eFluor 660; Thermo Fisher Scientific (1:100), 30 minutes on ice. The cells were washed and rinsed with PBS (1×) and suspended in FACS buffer and transferred to FACS tube. The stained cells were analyzed using BD FACSymphony. Thus, stimulating the vagus nerve prevents infiltration of IFNg+ T cells into the central nervous system, delays disease symptoms, and abrogates disease severity in the EAE rodent model of MS.
Stimulation Protocol—Dosing Returning to FIGS. 12 and 13, these figures show animal (mouse) model data illustrating the range of dosing parameters applied. In FIGS. 12 and 13 mice were treated with LPC at precise vertebral regions and VNS was applied from an implanted electrode after demyelinating lesions were permitted to develop. For example, mice were anesthetized and stabilized into a stereotaxic frame, and a midline incision was made between the scapulae to access the spinous process of the T2-T5 vertebra; 0.5 uL of LPC was injected into the spinal cord at a rate of 0.250 uL/min for 2 min, and the incision site sutured closed. VNS was delivered on Day 4 post-induction with LPC (when peak lesion size is expected), using charge-balanced, biphasic, square pulses having a 200-250 μs pulse width at 10 Hz for 60 seconds, unless indicated otherwise. Lesions were quantified by area of myelin loss, as assessed on luxol blue stained serial sections with nuclear fast red counterstain.

As shown in FIG. 12, applying VNS at a frequency of less than about 100 Hz (e.g., 75 Hz or less, 50 Hz or less, 40 Hz or less, 30 Hz or less, 25 Hz or less, etc.) was more effective than higher frequencies, e.g., 1.8 kHz and above. In this exemplary graph, no current was delivered to the Sham animals. All other mice were stimulated at current of 0.75 mA, and pulse train duration of 60 s. The 5 kHz group was stimulated with 5 kHz sinusoidal pulse; all other mice were stimulated at a 0.25 ms biphasic-charge balanced pulse. As shown in FIG. 12, significantly more lesion area was remyelinated after stimulation at 1, 10, or 20 Hz, and high frequency stimulation did not modulation remyelination. In general, the frequency range of between 1-10 Hz stimulation was more effective at enhancing remyelination than 20 Hz and higher.

As shown in FIG. 13, significantly more lesion area was remyelinated after stimulation at 1 or 5 minutes at 10 Hz, while in general, stimulation for less than 20 minutes (e.g., less than 15 minutes, less than 10 minutes, less than 9 minutes, less than 8 minutes, less than 7 minutes, less than 6 minutes, less than 5 minutes, etc.) was more effective than longer times. Curiously, 1 minute of stimulation was more effective than 5 minutes of stimulation. In this example, no current was delivered to the sham animals; all other mice were stimulated with a current of 0.75 mA, 10 Hz, 0.25 ms biphasic-charge balanced pulse. The pulse train duration was varied as shown.

Based on preliminary work, similar trends are expected to be seen in human patients. For example, it is likely that relatively low-frequency stimulation (e.g., between 0.1 and 20 Hz) and lower pulse train duration (e.g., less than 5 minutes) are more effective than higher frequency stimulation at longer pulse train duration. This result is surprising and in conjunction with the findings regarding total charge per day, suggests that the total charge applied to the vagus nerve per day may be optimally between about 2.5 nC and 7.5 mC per day to modulate endothelial cells, microglia, and/or macrophage to increase clearance of cellular debris (such as myelin debris) and therefore reduce lesion volume in diseases and disorders of myelination, including MS.

The distribution of dose of VNS to be delivered may be all at once (e.g., once per day, once per every other day, once per every third day, once per ever fourth day, once per every fifth day, once per every sixth day, once per week, etc.) or distributed over each day or days (e.g., 2× per day, 3× per day, 4× per day, 5× per day, etc.). The total charge delivered per day may be less than about 7.5 mC (e.g., about 7 mC/day, about 6.5 mC/day, about 6 mC/day, about 5.5 mC/day, about 5 mC/day, etc., in some variations between about 2.5 nC/day and about 7.5 mC/day, between about 2.5 nC/day and about 7 mC/day, between about 5 nC/day and about 6.5 mC/day per day, etc.).

The dosing may be varied or adjusted. In particular, the dose may be adjusted based on the time since starting treatment. In variations in which the VNS is applied through an implanted device, the dose may be tapered over time. For example, the apparatus may reduce the number and/or intensity of VNS applied over time, e.g., from once per day to once every two or three days, to once every week, etc. In some variations the dose may be adjusted based on a concurrently delivered drug or therapy. The dose of VNS may be decreased when a drug to treat a disease or disorder of myelination is being concurrently taken.

As mentioned above, in some variations a dose may be frequency optimized around about 10 Hz (e.g., between 0.1 Hz and 20 Hz, between about 1 Hz and 15 Hz, between about 1 Hz and 12 Hz, etc.). In some cases, frequencies above 30 Hz are found to be substantially ineffectual. Preliminary data also suggests that a stimulation of 1 min or less may be sufficient to achieve a full remyelination effect per dose. Thus, in some variations the dose of VNS for treating diseases or disorders effecting myelination may be limited to between about 0.1 second and 120 seconds, e.g., less than about 120 seconds, less than 100 seconds, less than 90 seconds, less than 80 seconds, less than 70 seconds, less than 60 seconds, less than 50 seconds, less than 45 seconds, less than 40 seconds, less than 35 seconds, less than 30 seconds, etc. Any of the apparatuses described herein may be configured to limit stimulation within these effective ranges, which may prevent overshooting the effective range.

Animal data suggests that there may be a lower-bounding intensity of about 0.25 mA (in mice), below which VNS is ineffective. In humans this level may be lower or equivalent (e.g., 0.05 mA, 0.1 mA, 0.15 mA, 0.2 mA, 0.25 mA). In general, the effective range of VNS in order to achieve remyelination as described herein appears to be different from the range of VNS applied parameters to achieve other effects, including previously described modulation of inflammation. For example, the application of VNS to modulate myelination (remyelination/demyelination) appears to be more tightly bounded than anti-inflammatory effects. For example, dosing with applied energy outside of this range (e.g., less than the minimal levels, greater than the maximum levels) which may have a robust anti-inflammatory effect will have little or no effect on myelination (e.g., outside of between 2.5 nC and 7.5 mC per day).

Preliminary work in an animal model (e.g., dog) has shown that tapering the applied dose (e.g., from daily, gradually tapering to weekly) may be effective, as (surprisingly) the effects of stimulation within the effective parameter ranges may be longer lasting over time.

Multi-Modal Stimulation

As described herein, the VNS treatments described herein have been found to reduce demyelination and promote remyelination effective for treating various neurodegenerative and/or neuroinflammatory disorders such as multiple sclerosis. Although treatments for reducing demyelination may also promote remyelination and vice versa, the underlying mechanisms of demyelination and remyelination may differ. Furthermore, the optimal frequencies for VNS may be different, and may span different (and non-overlapping) ranges. Thus, the methods and apparatuses described herein may include applying different "doses" of VNS at different frequencies (e.g., different frequency ranges), to enhance either or both demyelination (e.g., clearance) and remyelination. In some variations the methods and apparatuses may adjust the duration of one frequency component over the other in order to enhance either demyelination or remyelination at different times in a patient's treatment. For example, in some variations, the method or apparatus may be configured to apply stimulation at a first frequency of between 1 and 20 Hz (e.g., between 1 and 10 Hz, between 1 and 7 Hz, between 1 and 5 Hz, etc.) to reduce or prevent demyelination, and a second dose of electrical stimulation to increase remyelination at a second frequency that is higher than the first frequency (e.g., between 10 and 30 Hz, between 15 and 30 Hz, etc.). In some variations the method or apparatus may be configured to apply the lower dose (lower frequency range to prevent or reduce demyelination) but may switch to applying either both the lower frequency range (the first frequency) and the higher frequency range (e.g., the second frequency) when a trigger event is detected. The trigger event may be triggered by the user (e.g., the patient and/or physician or other health care practitioner), e.g., in response to a demyelination event. In some variations the trigger event may be triggered by detecting one or more biomarkers for demyelination, as described herein.

With respect to MS in particular, the methods and apparatuses described herein may be used to specifically treat relapsing-remitting MS (RRMS). As described above, these methods and apparatuses may be used to prevent or reduce the effects of periods of active inflammation ("relapses") and/or during intervals between active inflammation. Alternatively, in some variations the apparatuses and methods described herein may be used in particular to treat primary-progressive MS (PPMS). The parameters (e.g., controller, feedback, etc., including in particular the frequencies used for treatment and/or the dosing schedule) may be adjusted based on the type of MS in addition or instead of patient-specific markers (e.g., biomarkers). These methods and apparatuses may also or alternatively be adapted for treatment of second-progressive MS (SPMS) and/or progressive-relapsing MS (PPMS).

Demyelination is generally associated with an immune response and proinflammatory mechanisms. Remyelination is regenerative process associated with immune resolution. As described herein some types of VNS stimulation (e.g., lower-frequency, such as between about 1-20 Hz, e.g., between about 1-10 Hz, between about 1-7 Hz, between about 1-5 Hz, etc.) are more preventative and may reduce the severity of demyelination, e.g., by preventing IFNg+ T-cell infiltration (e.g., by immunocytes, including Th1 cells) and myelin breakdown. Other types of VNS stimulation (e.g., higher frequency stimulation, e.g., between 10-30 Hz, e.g., between 12-30 Hz, between 15-30 Hz, between 20-30 Hz, etc.) may enhance remyelination. Thus, as mentioned above, a VNS treatment regimen can be optimized to include different stimulation modes based on whether the stimulation parameters are more effective/efficient at reducing demyelination or promoting remyelination. For example, a first stimulation mode can be optimized to target reduction of demyelination and a second stimulation mode can optimized to target increase of remyelination. In some implementations, a VNS treatment regimen includes a combination of first mode and second mode stimulations. In other implementations, a VNS treatment regimen includes only first mode stimulation(s) or only second mode stimulation(s). Any of these systems and methods may be configured to toggle between the first mode and the second mode based on feedback (user and/or biomarker feedback), either manually, semi-automatically or automatically. In some variations the amount of first mode stimulation and second mode stimulation may be adjusted, e.g., by increasing the percentage of the total simulation, which may be limited, as described herein to a total daily amount of charge transferred (e.g., between 2.5 nC and 7.5 mC), and/or a total daily stimulation time (e.g., between 1 minute and 5 minutes per day, etc.). The percent of stimulation in the first mode and the second mode may be approximately equal (e.g., about half of the stimulation at the first mode frequency and about half of the stimulation at the second mode frequency, i.e., 50%/50%, or about 40%/60%, about 30%/70%, about 20%/80%, about 10%/90%, about 60%/40%, about 70%/30%, about 80%/20%, about 80%/10%, etc.).

In some cases, a treatment regimen includes a series of separately applied stimulations that include both first mode stimulations (targeting reduction in demyelination) and second mode stimulations (targeting increasing remyelination). For example, each first mode stimulation may be directly followed by a second mode stimulation. Alternatively, as set of multiple first mode stimulations (e.g., 2, 3, 4, 5, 6, 10, or 20) may be applied, followed by a set of multiple second mode stimulations (e.g., 2, 3, 4, 5, 6, 10, or 20). In some cases, a first set of multiple first mode stimulations (e.g., 2, 3, 4, 5, 6, 10, or 20) may be applied, followed by a single second mode stimulation, followed by a second set of multiple first mode stimulations (e.g., 2, 3, 4, 5, 6, 10, or 20). In some cases, a first set of multiple second mode stimulations (e.g., 2, 3, 4, 5, 6, 10, or 20) may be applied, followed by a single first mode stimulation, followed by a second set of multiple second mode stimulations (e.g., 2, 3, 4, 5, 6, 10, or 20). The number of stimulations and/or the total stimulation time using a particular mode can be chosen based on whether a patient's condition warrants an emphasis on demyelination reduction or remyelination promotion.

In some cases, the treatment regimen is chosen based on symptoms of the patient. For example, in some variations, one or more first mode simulations (targeting reduction in demyelination) may be administered if the patient is experiencing a flare-up in symptoms to counteract inflammation processes. Once inflammation has subsided to a sufficient extent, one or more second mode simulations (targeting increasing remyelination) may be administered to promote restorative cellular processes an immune resolution.

In some cases, the VNS treatment regimen is based on a particular neurodegenerative and/or neuroinflammatory condition or disease. For instance, a treatment regimen that includes a greater degree of first mode simulations targeting reduction in demyelination may be administered to patients whose conditions are associated with higher levels of inflammatory or pro-inflammatory cellular processes. A treatment regimen that includes a greater degree of second mode simulations targeting increasing remyelination may be administered to patients whose conditions are associated with lower levels of inflammation in order to promote healing.

In some variations, the treatment regimen is modulated based on biomarker feedback. For example, the stimulation regimen may be modified to include a greater degree of (or solely) first mode simulations targeting reduction in demyelination in response to the presence of biomarker(s) indicating demyelination. Likewise, the stimulation regimen may be modified to include a greater degree of (or solely) second mode simulations targeting remyelination in response to the presence of biomarker(s) indicating lower levels of demyelination. In some cases, the degree of the first and second mode stimulations is based on threshold levels of one or more biomarkers.

In some implementations, the stimulation parameters for reducing demyelination (first mode stimulation) includes lower frequencies compared to stimulation parameters for promoting remyelination (second mode stimulation). In some embodiments, the demyelination-reducing (first mode) frequencies are less about 10 Hz (e.g., <10 Hz, <8 Hz, <6 Hz, <4 Hz, <3 Hz, or <2 Hz). In some embodiments, the demyelination-reducing (first mode) frequencies range from about 1 Hz to about 9 Hz (e.g., 1 Hz-9 Hz, 1 Hz-8 Hz, 1 Hz-6 Hz, 1 Hz-5 Hz, 1 Hz-3 Hz, 2 Hz-9 Hz, 2 Hz-6 Hz, 2 Hz-4 Hz, or 2 Hz-3 Hz). In some embodiments, the remyelination-promoting (second mode) frequencies are about 10 Hz or greater (e.g., 10 Hz or greater, 11 Hz or greater, 15 Hz or greater, 20 Hz or greater, or 25 Hz or greater). In some embodiments, the remyelination-promoting (second mode) frequencies range from about 10 Hz to about 30 Hz (e.g., 10 Hz-30 Hz, 10 Hz-25 Hz, 11 Hz-20 Hz, 10 Hz-15 Hz, 15 Hz-30 Hz, 15 Hz-2 Hz, or 20 Hz-30 Hz).

Any of the demyelination-reducing (first mode) and remyelination-promoting (second mode) stimulations may be characterized as having low current and/or low duty-cycle stimulation characteristics described herein. In some implementations, the demyelination-reducing (first mode) and remyelination-promoting (second mode) stimulations are characterized as having a current ranging from about 0.1 mA to about 5 mA (e.g., 0.1-4 mA, 0.1-3 mA, 0.1-2 mA, 0.1-1 mA, 0.25-1 mA, 0.1-0.75 mA, 0.25-0.75 mA, etc.), a stimulation duration ranging from about 1 second to about 5 minutes (e.g., 1 sec-5 min, 1 sec-3 min, 1 sec-2 min, 1 sec-1 min, 30 sec-1 min, or 30 sec-2 min, 30 sec-5 min, 30 sec-4 min, 30 sec-3 min, etc.), and/or have an off time between simulation ranging from about 10 minutes to about 24 hours (e.g., 10 min-24 hrs, 10 min-6 hrs, 30 min-6 hrs, 6 hrs-24 hrs, or 30 min-24 hrs).

Combination with Drugs

The methods and apparatuses described herein may be combined or used concurrently with (e.g., in conjunction with) one or more drugs, including drugs to treat a disease or disorder of myelination.

It is well known that it may be difficult to combine or use multiple drugs for treating diseases or disorders of myelination such as multiple sclerosis (MS), because such drugs may interact in undesirable and potentially dangerous ways. The methods and apparatuses described herein may be used in conjunction with one or more drugs without negative interactions between the VNS methods and apparatuses described herein and other, pharmaceutically-based therapies. The VNS methods and apparatuses described herein to treat a disease or disorder of myelination may be used in conjunction with one or more of: Avonex (interferon beta-1a), Betaseron (interferon beta-1b), Copaxone (glatiramer acetate), Extavia (interferon beta-1b), Glatiramer Acetate Injection (glatiramer acetate-generic equivalent of Copaxone 20 mg and 40 mg doses), Glatopa (glatiramer acetate—generic equivalent of Copaxone 20 mg and 40 mg doses), Plegridy (peginterferon beta-1a), Rebif (interferon beta-1a), Aubagio (teriflunomide), Gilenya (fingolimod), Tecfidera (dimethyl fumarate), Mayzent (siponimod), Mavenclad (cladribine), Lemtrada (alemtuzumab), Novantrone (mitoxantrone), Ocrevus (ocrelizumab), Tysabri (natalizumab), Solu-Medrol (methylprednisolone), Deltasone (prednisone), H. P. Acthar Gel (ACTH), and Ampyra (dalfampridine).

The methods and apparatuses described herein for applying VNS may therefore be combined with a pharmacological treatment with low risk of additional side effects, possibly because the VNS results in an enhancement of native response, such as the increase in microglia and/or macrophage activity, often a different pathway than the pharmacological agent.

In particular, the VNS methods and apparatuses described herein may be used with one or more drugs that enhance remyelination. For example, the methods and apparatuses described herein may be used with a receptor muscarinic type 3 (M3R) modulating drug. The VNS methods and apparatuses described herein may alternatively or additionally be used with a B-cell targeting drug (e.g., drugs that target cell-surface markers on B-cells and T-cells, such as cladribineand Alemtuzumab).

The immune cell modulating effects of VNS can be enhanced by, or can be used to enhance the effect of, additional drugs to treat patients with neuroinflammatory disorders such as multiple sclerosis (MS).

In some cases, the VNS treatments described herein can be used in combination with Interferon β drugs and generics, glatiramer acetate and generics, and daclizumab. Modes of action targeting interferon β-1a and 1b receptors and T-cell activation can be complimentary and additive to VNS. These combinations may reduce central nervous system inflammation and demyelination.

In some cases, the VNS treatments described herein can be used in combination with fingolimod, teriflunomide, and dimethyl fumarate. Modes of action targeting lymphocyte migration or activation can be additive to VNS. These combinations may reduce central nervous system inflammation and demyelination.

In some cases, the VNS treatments described herein can be used in combination with mitoxantrone, alemtuzumab, ocrelizumab, and natalizumab. Modes of action targeting induce DNA breakage, CD52 to induce cell lysis, B-cell CD20 antigen for depletion, and/or integrin receptors to alter leukocyte migration can be complimentary and can be additive to VNS. These combinations should reduce central nervous system inflammation and demyelination.

In some cases, the VNS treatments described herein can be used in combination with clemastine, a Selective Estrogen Receptor Modulator (SERM) such as bazedoxifene, and other drugs targeting oligodentrocyte progenitor cells to enhance maturation into myelin-producing oligodendrocytes. Mode of action targeting enhanced maturation of myelin-producing oligodendrocytes can be complementary to VNS effects on phagocytosis and can be additive. These combinations should enhance remyelination and clinical recovery from central nervous system damage.

In some variations, the therapy may include implanting an internal VNS stimulator, and after the patient is stable and healed, giving the patient a drug, and maintaining the VNS indefinitely. The use of VNS alone or in combination with other, e.g., drug, therapies may be used to reduce demyelination and/or increase remyelination. In some variation the use of VNS alone or in combination with other, e.g., drug, therapies may delay the onset of MS, prevent the decline and in some cases reverse the decline in MS patients. In some cases, patients that do not respond to traditional therapies may respond to VNS therapy to treat a disease or disorder of myelination.

When the VNS as described herein is used in conjunction with a pharmaceutical (e.g., drug) therapy, the drug used may be adjusted, e.g., to reduce the dose of the pharmaceutical, thus the dosing of the additional MS drug may be reduced substantially compared to the dose without VNS. In some variations a method of treatment may include titrating the dose of the drug therapy when used in conjunction with the VNS as described herein.

VNS Implant Location

When the VNS therapy described herein include an implanted (e.g., surgically implanted) microstimulator device, in some variations the implanted device may be attached or implanted on or adjacent to the vagus nerve at a region of the neck (cervical placement). Alternatively, the microstimulator device may be implanted in a subdiaphragmatic location, on the subdiaphragmatic vagus nerve, the splenic nerve, etc.

Transcutaneous Stimulation

Alternatively, in some variations the VNS is applied externally by one or more transcutaneous electrical stimulators. Energy may be applied externally on one or more locations such as the neck (including the sides of the neck, beneath the ears), chest (e.g., midline of chest), abdomen, ear, etc. Non-invasive (e.g., external) stimulation may be configured so that the stimulation received by the vagus nerve is within the parameters described for implantable systems as described herein. For example, a handheld or worn application may be applied to the patient's neck or other region on the skin overlying a vagus nerve region and electrical energy applied within the 0.1-30 Hz (e.g., 1-10 Hz)

range, at power settings configured so that the total charge received by the vagus nerve is between 2.5 nC and 7.5 mC per day.

Feedback from MS Biomarkers

Any of the apparatuses and methods described herein may also be modulated by the use of one or more markers, and specifically, markers for myelination (including myelination fragments, myelination clearance, etc.) and/or markers for microglial and/or other macrophage activity. For example, markers may include microglia markers such as antibody markers (e.g., antibodies to fractalkine receptor (Cx3cr1), TMEM119, CD11b and CD45, ionized calcium binding adaptor molecule 1 (Iba1), CX3CR1 is the fractalkine receptor, F4/80, CD68, CD40, etc. In addition, markers may look specifically for myelin, including antibodies direct to myelin.

For example, makers may include qualitative and quantitative measurement of elevated immunoglobulins (IgG) in the CSF and/or blood. Isoelectric focusing (IEF) is one qualitative method for detection of oligoclonal bands (OCBs) used to track MS, and has been shown to have a sensitivity higher than 95% in MS15 and a specificity generally considered to be more than 86%. Any of the methods and apparatuses described herein may track the OCBs within an individual patient and adjust the therapy (e.g., applied VNS and/or VNS plus drug) based on changes in this marker. Other similar markers may include the detection of oligoclonal IgM bands, which may be predictive for a more severe disease course with a shorter time period to the next relapse.

Alternatively or additionally, antibodies directed against myelin-oligodendrocyte-glycoprotein (MOG), which is typically localized on the surface of myelin sheaths and oligodendrocytes, and/or myelin basic protein (MBP), which constitutes 30% of total central myelin protein, may be measured/or tracked to adjust the VNS therapy as described herein.

Any of the markers described herein may be specific to the disorder or disease of myelination to be treated. For example, Neuromyelitis optica (NMO) is an inflammatory demyelinating disorder that selectively affects the spinal cord and optic nerves. The presence of NMO-specific autoantibodies, NMO IgG may be used as a marker. Further, Aquaporin-4, a water channel located in astrocyte foot processes at the blood—brain barrier is a target antigen.

Other markers may include Interferon-β (IFN-β). Interferon-β, including neutralizing antibodies (NAb) to IFN-β, levels may track the progression or state of a disorder of myelination and may be used to modulate the VNS therapy. Increases (or high normalized levels) in NAb titres may indicate an increase in the dose of VNS.

Natalizumab is a humanized monoclonal antibody that binds to very late activation antigen 4 (VLA-4), an α4β1 integrin, and thereby prevents the migration of leukocytes through the blood-brain barrier. Thus, natalizumab (and/or NAb to natalizumab) may be used as a marker for modulating VNS treatment in patients.

Markers may be tested by sampling a fluid (e.g., blood, spinal fluid, etc.) either acutely periodically (during medical visits) and/or directly by an implant using one or more sensors within the device. In some variations the markers may be sampled noninvasively, by looking at, for example, retinal markers, optic nerve markers, etc.

As mentioned above any of the systems described herein can be configured to modulate stimulation based on the onset of a flare-up, in which the patient experiences the onset or worsening of symptoms (e.g., pain, muscular cramping or stiffness and/or fatigue). In some variations, the patient provides input indicating the onset of a flare-up, for example, via a portable (e.g., wearable) electronic device. In some variations, the measurement of one or more of the biomarkers can indicate whether the patient is experiencing, or about to experience, a flare-up. Treatment can then be prescribed based on whether a flare-up is occurring, about to occur, and in some cases, based on a severity of the flare-up. In some implementations, an increase in one or more biomarkers associated with demyelination and/or inflammation may indicate the onset of a flare-up, and the stimulation parameters may be modulated specifically to counteract the demyelination and/or inflammation. For example, the stimulation parameters may be modulated to those found to reduce demyelination (e.g., frequency less than 10 Hz, less than 8 Hz, less than 5 Hz, or less than 3 Hz).

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A system for reducing demyelination and/or increasing remyelination by stimulation of a vagus nerve, the system comprising:
    a vagus nerve stimulator configured to be implanted over or adjacent to a vagus nerve;
    one or more electrodes on the vagus nerve stimulator configured to apply electrical stimulation to the vagus nerve; and
    a controller coupled to the vagus nerve stimulator and configured to apply electrical stimulation to the vagus nerve from the one or more electrodes to reduce demyelination and/or increase remyelination in central nervous system nerves and/or peripheral nervous system (PNS) nerves within a patient, wherein the controller is constrained to limit a total charge per day to between 2.5 nC and 7.5 mC to reduce demyelination and/or increase remyelination within the patient by increasing clearance of neuronal cellular debris by phagocytosis and efferocytosis,
    further wherein the controller is configured to limit a frequency of the electrical stimulation to less than a maximum of 30 Hz.

2. The system of claim 1, further comprising an input configured to receive one or more marker level indicators, wherein the controller is configured to adjust an applied charge based on the one or more marker level indicators.

3. The system of claim 2, further comprising a biosensor configured to detect a marker from the patient's blood and/or cerebrospinal fluid and to determine the one or more marker level indicators from the marker.

4. The system of claim 1, wherein the controller is configured to deliver the electrical stimulation during one or more dose sessions of 5 or fewer minutes.

5. The system of claim 1, wherein the controller is configured to apply a charge per day at a frequency between 1 and 20 Hz.

6. The system of claim 5, wherein the controller is configured to apply the charge per day at a frequency between 1 and 12 Hz.

7. The system of claim 1, wherein the system is configured to be implanted.

8. The system of claim 1, further comprising a nerve cuff configured to secure the vagus nerve stimulator to the vagus nerve.

9. The system of claim 1, wherein the controller is configured to apply a charge per day at two distinct frequencies between 1 and 20 Hz.

10. The system of claim 1, wherein the controller is configured to apply a first dose of the electrical stimulation to reduce demyelination at a first frequency between 1 and 20 Hz, and a second dose of electrical stimulation to increase remyelination within the patient at a second frequency that is higher than the first frequency.

11. The system of claim 10, wherein the first dose of electrical stimulation has a frequency less than 10 Hz, and the second dose of electrical stimulation has a frequency ranging from 10 Hz to 30 Hz.

12. The system of claim 10, wherein the first dose of electrical stimulation has a frequency ranging from 1 Hz to 5 Hz, and the second dose of electrical stimulation has a frequency ranging from 5 Hz to 30 Hz.

13. A system for reducing demyelination and/or increasing remyelination by stimulation of a vagus nerve, the system comprising:
- a vagus nerve stimulator configured to be implanted over or adjacent to a vagus nerve;
- one or more electrodes on the vagus nerve stimulator configured to apply electrical stimulation to the vagus nerve; and
- a controller coupled to the vagus nerve stimulator and configured to apply electrical stimulation to the vagus nerve from the one or more electrodes to reduce demyelination and/or increase remyelination in central nervous system nerves within a patient, wherein the controller is constrained to limit a total charge per day to between 2.5 nC and 7.5 mC to reduce demyelination and/or increase remyelination within the patient by increasing clearance of neuronal cellular debris by phagocytosis and efferocytosis,
- further wherein the controller is configured to limit a frequency of the electrical stimulation to less than a maximum of 30 Hz.

* * * * *